United States Patent [19]

Schaub et al.

[11] 4,017,534

[45] Apr. 12, 1977

[54] 16-FLUORO-11-DEOXY-13-DIHYDRO-PROSTAGLANDIN

[75] Inventors: Robert Eugene Schaub, Upper Saddle River, N.J.; Middleton Brawner Floyd, Jr., Suffern, N.Y.; Martin Joseph Weiss, Oradell, N.J.

[73] Assignee: American Cyanamid Company, Stamford, Conn.

[22] Filed: Oct. 14, 1975

[21] Appl. No.: 621,919

Related U.S. Application Data

[60] Division of Ser. No. 475,479, June 3, 1974, Pat. No. 3,932,463, which is a continuation-in-part of Ser. No. 263,036, June 15, 1972, abandoned, which is a continuation-in-part of Ser. No. 95,911, Dec. 7, 1970, abandoned.

[52] U.S. Cl. .................. 260/468 D; 260/488 R; 260/514 D

[51] Int. Cl.² ..................................... C07C 177/00
[58] Field of Search ........ 260/468 D, 514 D, 488 R

[56] References Cited

UNITED STATES PATENTS

| 3,707,548 | 12/1972 | Bagli et al. | 260/468 |
| 3,884,942 | 5/1975 | Caton et al. | 260/348 |

FOREIGN PATENTS OR APPLICATIONS

| 7,305,817 | 10/1973 | Netherlands | 260/468 |

*Primary Examiner*—Robert Gerstl
*Attorney, Agent, or Firm*—Edward A. Conroy, Jr.

[57] ABSTRACT

This disclosure describes novel 11-deoxy-13,14-dihydro-prostaglandin-9-ketals useful as bronchodilators and as gastric acid secretion inhibitors.

13 Claims, No Drawings

16-FLUORO-11-DEOXY-13-DIHYDRO-PROSTA-GLANDIN

CROSS REFERENCE TO RELATED APPLICATIONS

This is a division of application Ser. No. 475,479, filed June 3, 1974, now U.S. Pat. No. 3,932,463, which is a continuation-in-part of our copending application Ser. No. 263,036, filed June 15, 1972, which in turn is a continuation-in-part of our application Ser. No. 95,911, filed Dec. 7, 1970, both now abandoned.

BRIEF SUMMARY OF THE INVENTION

This invention relates to the novel 9-ketal derivatives of the prostanoic acids and esters. More specifically the compounds of this invention are all the optical antipodes, racemates, diastereoisomers, enantiomers, racemic mixtures and diastereomeric mixtures of the following general formulae:

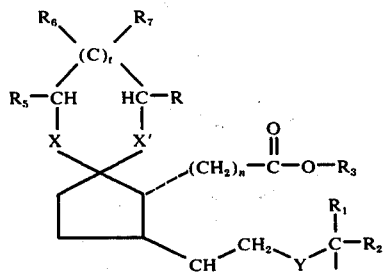

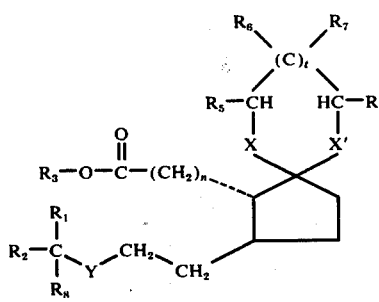

wherein X is an oxygen or sulfur atom; X' is an oxygen or sulfur atom; Y is a divalent moiety of the formulae

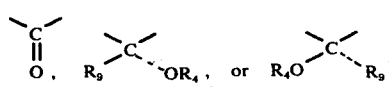

wherein $R_4$ is hydrogen or alkanoyl and $R_9$ is hydrogen or lower alkyl with the proviso that when $R_9$ is lower alkyl then $R_4$ must be hydrogen; R is hydrogen, lower alkyl, or halo substituted lower alkyl; $R_1$ is hydrogen, fluorine, or lower alkyl; $R_2$ is alkyl having from two to seven carbon atoms; $R_3$ is hydrogen or alkyl having from one to 12 carbon atoms; $R_5$ is hydrogen, lower alkyl, or halo substituted lower alkyl; $R_6$ is hydrogen or lower alkyl; $R_7$ is hydrogen or lower alkyl; $R_8$ is hydrogen, fluorine, or lower alkyl; $n$ is an integer from 4 to 8, inclusive; $t$ is zero or 1 with the understanding that cyclic ketals are contemplated in all instances except that the moiety

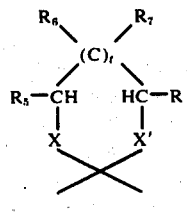

may also be a moiety of the formula:

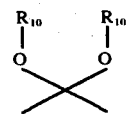

wherein $R_{10}$ is lower alkyl, aralkyl, or $\beta, \beta, \beta$-trihaloethyl.

Suitable lower alkyl and halo substituted lower alkyl groups contemplated by the present invention are those having up to four carbon atoms. Suitable alkanoyl groups are those having from two to 15 carbon atoms. Suitable aralkyl groups are benzyl, $\alpha$-phenethyl, $\beta$-phenethyl, and the like, whereas halo is exemplified by fluoro, chloro and bromo.

A preferred embodiment of this invention are all the optical antipodes, racemates, diastereoisomers, enantiomers, racemic mixtures and diastereomeric mixtures of the following general formulae:

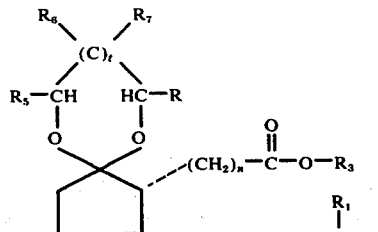

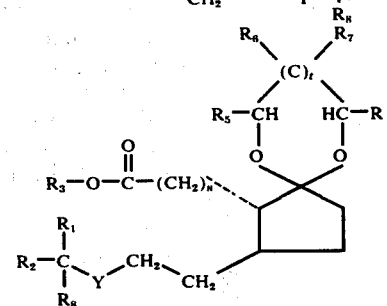

wherein R, $R_1, R_2, R_3, R_5, R_6, R_7, R_8, n, t,$ and Y are all as defined hereinabove.

DETAILED DESCRIPTION OF THE INVENTION

Also embraced within the scope of the present invention are the non-toxic, pharmaceutically acceptable salts of the novel compounds of the present invention when $R_3$ is hydrogen. The cations comprised in these salts include, for example, the non-toxic metal cations such as the sodium ion, potassium ion, calcium ion, and magnesium ion as well as the organic amine cations such as the tri(lower alkyl)amine cations (e.g., triethylamine, triethanolamine, procaine, and the like).

The prostaglandins are a family of closely related compounds which have been obtained from various animal tissues, and which stimulate smooth muscle, lower arterial blood pressure, antagonize epinephrine-induced mobilization of free fatty acids and have other pharmacological and autopharmacological effects in mammals. See Bergstrom et al., J. Biol. Chem., 238, 355 (1963); Horton, Experientia, 21, 113 (1965); and "The Prostaglandins" Vol. 1, ed. P. W. Ramwell, Plenum Press, New York, 1973, and references cited therein. All of the so called natural prostaglandins are derivatives of prostanoic acid:

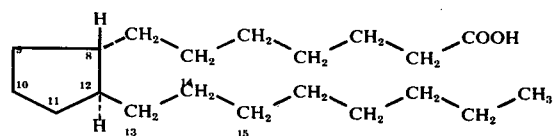

The hydrogen atoms attached to C–8 and C–12 are in trans-configuration. Substitution of $C_{15}$ with an oxy function creates a new assymetric center. In the natural mammalian prostaglandins this carbon atom is in the (S) configuration and is formulated as A, the (R) configuration being formulated as B.

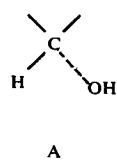 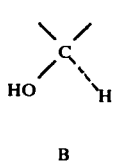

A            B

The natural prostaglandins represent only one of the possible optical isomers. The compounds of this invention include all possible optical isomers.

The novel compounds of this invention can be prepared from the corresponding 9-oxo-prostanoic acids or esters (I) by the usual techniques of ketalization involving treatment of the ketone with an excess of the requisite diol, dithiol, hydroxythiol (II) or alcohol in the presence of an acid catalyst. The preparation of the non-cyclic ketals can also be accomplished by treatment with the appropriate tri-alkyl or tri-aralkyl orthoformate in the presence of an acid catalyst. Introduction of a 15-alkyl group is accomplished by oxidation of the 15-hydroxy function in (in III, $R_4$=hydrogen) and subsequent treatment with an alkyl Grignard or alkyl lithium reagent to give (V).

Saponification of esters represented by (III) or (V) by the usual technique provides the corresponding 15-hydroxy carboxylic acids. Conversely, it is possible to esterify the 15-hydroxy group in the usual manner, for example by treatment with an alkanoic acid anhydride in pyridine. The carboxylic acid function can be esterified by treatment with the appropriate diazoalkane, or by other methods well-known to the art.

In Flowsheet A which follows the formation of certain of the novel compounds of this invention is illustrated. In the Flowsheet R, $R_1,R_2,R_3,R_4,R_5,R_6,R_7,R_8,R_9,X,X',n$ and $t$ are as defined above.

FLOWSHEET A

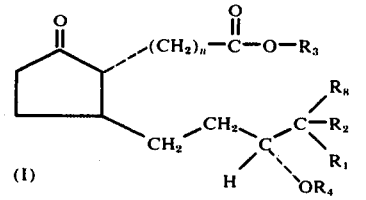

(I)

+

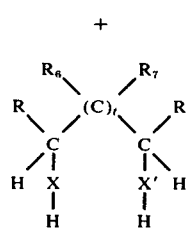

(II)

↓

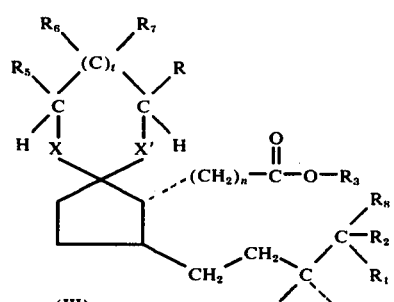

(III)

↓ $R_4$ = hydrogen

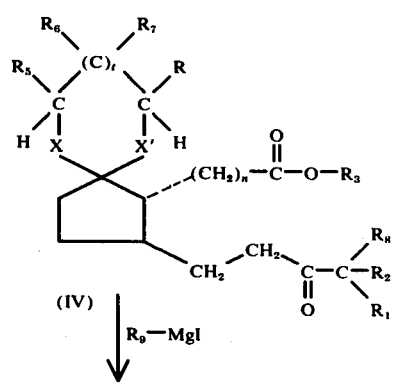

(IV) ↓ $R_9$—MgI

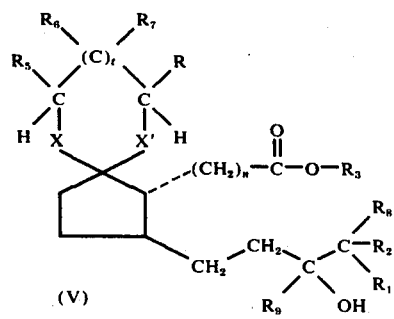

(V)

The 16-fluoro and 16,16-difluoro 9-oxo-intermediates described herein above novel compounds and are useful as intermediates for the preparation of certain of the ketals of this invention. They as well as the corresponding 9-hydroxy derivatives have intrinsic utility as gastric acid secretion inhibitors, bronchodilators, and hypotensive agents and accordingly may be useful for the treatment of peptic ulcers, gastric hyperacidity, gastric erosion, bronchial asthma and hypertension. These novel optically active compounds have the following general formula and are to be considered as embraced within this invention.

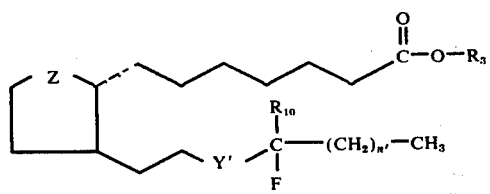

wherein $R_3$ is as defined hereinabove; $Y'$ is a divalent moiety selected from the group consisting of

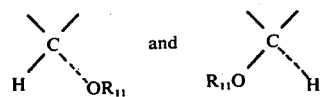

wherein $R_{11}$ is hydrogen or a lower alkanoyl radical; $R_{10}$ is either hydrogen or fluorine; $n'$ is an integer from 2 to 5, inclusive; and Z is a divalent moiety from the group consisting of

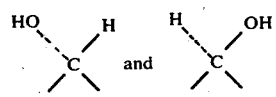

The novel compounds of the above general formula can be prepared by catalytic hydrogenation of the corresponding $\Delta^{10(11)}$-9-oxo derivatives, for example (V).

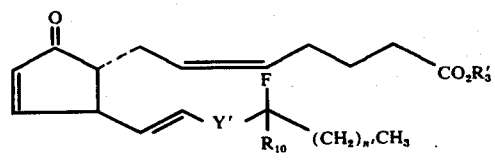

(V)

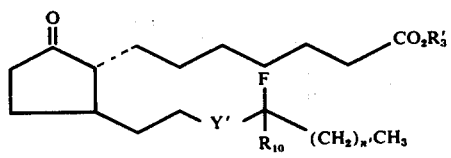

(VI)

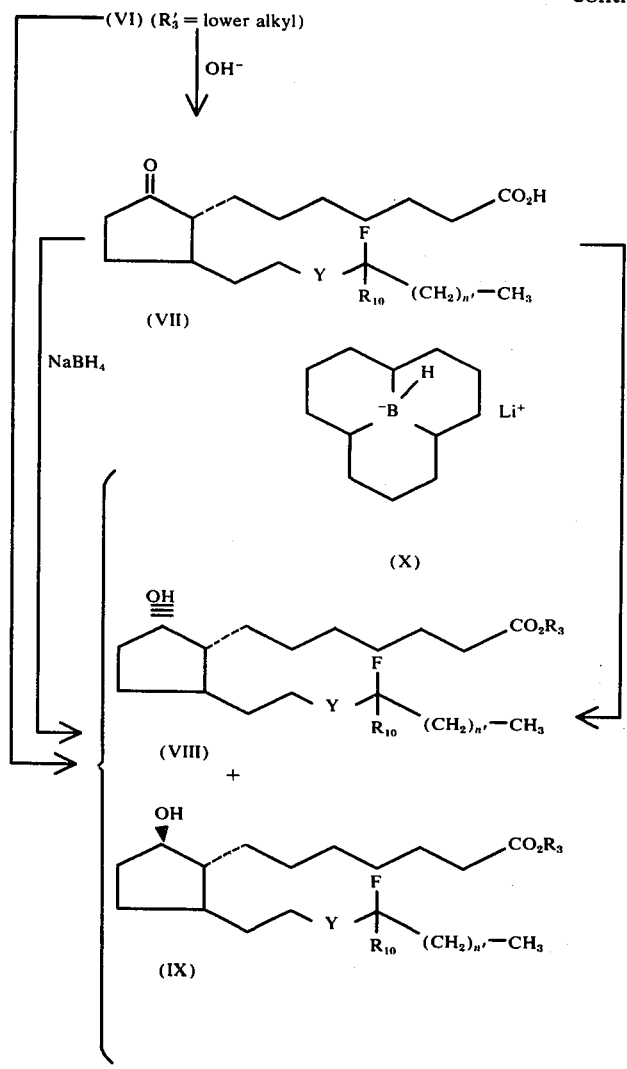

In the above synthetic sequence Y', $R_3$, $n_1$ and $R_{10}$ as hereinabove defined; $R'_3$ is an alkyl group of one to 12 carbon atoms. Hydrogenation of (V) is carried out in the usual fashion; rhodium-on-carbon is a useful catalyst. Saponification of the product (VI) to the prostenoic acid (VII) is usually effected where $R'_3$ is lower alkyl, preferably methyl. Sodium borohydride reduction of (VI) or (VII) provides a mixture of the $9\alpha$- and $9\beta$-hydroxy derivatives, (VIII) and (IX), respectively. The diols are separable by the usual procedures of column chromatography. A more stereo-selective reduction of the $9\alpha$-ol (VIII) is possible with lithium perhydro-9b-boraphenalyl hydride (X) [H. C. Brown and W. C. Dickason, Journ. Amer. Chem. Soc., 92, 709 (1970)], or with lithium tri-sec-butylborahydride. The various esters and acids are obtainable by the usual methods of esterification, for example, with diazoalkanes, or saponification. The 15-O-alkanoyl derivatives are available by the usual techniques of hydroxy group acylation, e.g., treatment with acyl chloride in pyridine.

The novel compounds of the present invention are usually obtainable as oils having characteristic absorption spectra. They are relatively soluble in common organic solvents such as ethanol, ethyl acetate, dimethylformamide, and the like. The cationic salts of the compounds when $R_3$ is hydrogen are, in general, white to yellow crystalline solids having characteristic melting points and absorption spectra. They are relatively soluble in water, methanol, and ethanol but are relatively insoluble in benzene, diethyl ether, and petroleum ether.

The compounds of this invention can be isolated and purified by conventional methods. Isolation can be accomplished, for example, by dilution of the reaction mixture with water, extraction with a water-immiscible solvent such as methylene chloride, ethyl acetate, benzene, cyclohexane, ether, toluene and the like, chromatography, adsorption on ion-exchange resins, distillation, or a combination of these. Purification of the compounds of this invention can be accomplished by means known in the art for the purification of prostaglandins and lipids, fatty acids, and fatty esters. For example, reverse phase partition chromatography, countercurrent distribution, adsorption chromatography on acid washed Florisil (synthetic magnesium silicate), preparative paper chromatography, and combinations thereof can be used effectively to purify the compounds produced by the processes of this invention.

The racemic products and intermediates of this invention can be resolved into their optically active components by a number of methods of resolution well known in the art. For example, those compounds which are obtainable as free acids can be treated with an optically active base such as cinchonine, quinine, brucine, d- or l-α-phenylethylamine and the like to produce diastereoisomeric salts which can be separated by crystallization. Alternatively, the acid may be esterified with an optically active alcohol, e.g., d- or l-methanol, estradiol 3-acetate, etc., and the diastereoisomeric esters then resolved. Also, the 15-hydroxy function the examples which follow. Also, compounds in which $C_{15}$ is substituted by hydroxy and hydrogen and is in either the S or R configuration can be converted to the opposite configuration by transforming the hydroxy function to a methanesulfonylate or p-toluenesulfonylate or the like, treating with a relatively non-basic oxy nucleophile, e.g., potassium acetate or sodium benzoate, and saponifying the thus-formed ester. Inversion of configuration takes plate on reaction with the oxy-nucleophile which procedes by an $SN_2$ displacement (Walden inversion). This transformation is illustrated in the following sequence.

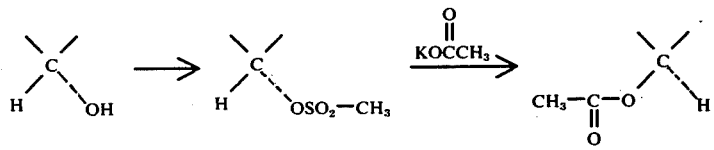

may be esterified with an optically active acid (e.g., d- or l-α-methoxy-α-trifluoromethylphenylacetic acid) and the resulting diastereoisomeric esters then separated by the usual techniques of fractional crystallization or chromatography. In more difficult instances it may be necessary to apply the technique of high speed liquid chromatography involving, if necessary, recycling techniques. [See G. Fallick, American Laboratory, 19–27 (August, 1973) as well as references cited therein. Additional information concerning high speed liquid chromatography and the instruments necessary for its application is available from Waters Associates, Inc., Maple Street, Milford, Mass.]. Another procedure would involve esterifying the 15-hydroxy function with a dibasic acid, such as phthalic acid, and treating the resulting phthalate acid-ester with an optically active base and separating the thus-formed diastereoisomeric salts by the usual procedures of fractional crystallization.

The resolution of the diastereoisomers or racemic mixtures of this invention can also be accomplished by reverse phase and absorption chromatography on an optically active support and adsorbent and by selective transformation of one isomer by microbiological or enzymatic means known to the art. Such transformations can be carried out by incubation or perfusion using methods well established in the art, followed by isolation and recovery of the isomer resistant to the metabolic transforamtion applied.

Individual diastereoisomers or racemates are also available by preparation from the corresponding resolved intermediates as illustrated in greater detail by Certain of the novel ketals of this invention are also useful for the preparation of other novel ketals of this invention as well as the novel 9-oxo-15 lower alkyl-15-hydroxy compounds that can be readily obtained from them by acid hydrolysis of the parent ketal. The ketal function then serves as a blocking group to allow the transformation of the secondary 15-hydroxy group to a tertiary hydroxy group via oxidation of the 15-ol followed by reaction with a lower alkyl magnesium halide.

The compounds of this invention are useful as bronchodilators for the treatment of asthma and chronic bronchitis. Bronchodilator activity is determined in guinea pigs against bronchospasms elicited by intravenous injections of 5-hydroxytryptamine, histamine or acetylcholine by the Konzett procedure. [See J. Lulling, P. Lievens, F. El Sayed and J. Prignot, Arzneimittel-Forschung, 18, 995 (1968).]

In Table A which follows bronchodilator activity for representative compounds of this invention against one or more of three spasmogenic agents is expressed as an $ED_{50}$ determined from the results obtained with three logarithmic cumulative intravenous doses.

TABLE A

| | Bronchodilator Activity (Konzett Assays) $ED_{50}$, mg./kg. | | |
|---|---|---|---|
| | Spasmogenic Agent | | |
| Compound | 5-hydroxytryptamine | histamine | acetylcholine |
| l-9,9-ethylenedioxy-15(S)-hydroxy-prostanoic acid | $2.53 \times 10^{-3}$ | $376 \times 10^{-6}$ | $27.4 \times 10^{-3}$ |
| l-9,9-(1-methylethyl-enedioxy)-15(S)-hydroxyprostanoic acid | $104 \times 10^{-6}$ | $50 \times 10^{-6}$ | $644 \times 10^{-6}$ |

In Table A' which follows bronchodilator activity for representative compounds of this invention against one or more of three spasmogenic agents is reported. In this assay candidate compounds are suspended in 10% gum arabic solution and the suspension is administered by the intraduodenal route. The activity of the compound at any one dose is then investigated throughout the following hour (see above-cited reference, J. Lulling et al.). Potency is then reported as 0, +, ++, +++, or ++++, wherein 0 represents no activity, + minimal activity and ++++ maximum activity.

TABLE A'

| Compound | Intraduodenal Dose mg./kg. | Spasmogenic Agent | | |
|---|---|---|---|---|
| | | 5-Hydroxy tryptamine | Histamine | Acetyl-choline |
| l 9,9-(2,2-di-methyl-1,3-propylenedioxy)-15(S)-hydroxy-prostanoic acid | 10 | + | + | +++ |
| l methyl 9,9-ethylenedioxy-15(S)-hydroxy-prostanoate | 10 | ++ | ++ | ++ |
| l 9,9-ethylene-oxythia-15(S)-hydroxyprostanoic acid | 10 | ++ | + | ++ |
| l 9,9-(1,3-propylenedioxy-15(S)-hydroxy-prostanoic acid | 3.2 | + | +++ | + |
| l methyl 9,9-(1,3-propylenedioxy)-15(S)-acetoxy-prostanoate | 10 | ++ | + | +++ |
| l methyl 9,9-(1,2-dimethylethylene-dioxy)-15(S)-acetoxyprostanoate | 10 | ++ | ++ | ++ |
| l methyl-9,9-(1-chloromethyl-ethylenedioxy)-15(S)-acetoxy-prostanoate | 10 | +++ | + | ++ |
| l 9,9-(1,2-dimethylethylene-dioxy)-15(S)-hydroxyprostanoic acid | 10 | ++ | + | +++ |
| l 9,9-(1-chloromethylethylene-dioxy)-15(S)-hydroxyprostanoic acid | 10<br>3.2 | +++<br>++++ | +++<br>++ | ++<br>++ |
| l methyl 9,9-(1-methylethylene-dioxy)-15(S)-acetoxyprostanoate | 10 | + | ++ | ++ |

The novel ketals of this invention also show bronchodilator activity when administered by aerosol to dogs wherein bronchoconstriction was induced by administration of pilocarpine. In this assay, l 9,9-ethylenedioxy-15(S)-hydroxyprostanoic acid, a representative ketal of this invention, shows important advantages over the corresponding ketone, l 9-oxo-15(S)-hydroxyprostanoic acid. Thus at an aerosol concentration (0.032%) at which the activity of the ketone is very weak, the activity of the ketal is fully-present-indicating that the ketal is at least 10 times as potent as the ketone. In human ketal aerosol does not induce cough, although ketone aerosol does. This is very important since coughing is one of the damaging side effects reported in the literature when prostaglandin aerosols are administered to human subjects. [See Y. Kawakami et al., *European Journal Clinical Pharmacology*, 6, 127 (1973); M. F. Cuthbert, *Brit. Med. Journ.* 723 (Dec. 20, 1969); H. Herxheimer and I. Roetscher, *European Journal Clinical Pharmacology*, 3, 123 (1971).]

The compounds of this invention are also useful as inhibitors of gastric acid secretion and peptic ulcer formation and may be used for the treatment of gastric hyperacidity, gastric erosion, and peptic ulcer. Inhibition of basal gastric acid secretion can be determined by the following procedure.

Female Sprague-Dawley rats weighting 140–160 grams are fasted in individual cages for 18–24 hours. The rats are then lightly anesthetized with ether and their front teeth extracted to avoid destruction of the plastic cannula. A midline incision is then made and the stomach and duodenum exposed. A flanged polyvinyl tube is inserted into the fundic portion of the stomach and secured with a purse string suture line using 4–O Mersilene. The rat is then dosed by injection of the compound into the duodenum (1.0 ml. per 100 gram body weight). After dosing, the abdominal wall and skin are closed using metal wound clips. The rate is replaced in a cage containing a longitudinal slit to allow the polyvinyl tube to hang freely. An 8 ml. plastic collecting tube is attached to the flanged cannula and hangs freely below the cage. The first 30 minute sample is discarded designating this time as zero. The collecting tube is attached again and samples removed at the end of 60 and 120 minutes. These samples are referred to as "A" and "B" in the table. The hourly samples are then transferred to a 15 ml. centrifuge and centrifuged for 5-10 minutes. Total and sediment volume are then recorded with the supernatent volume being used as volume of secretion. A 1 ml. or less aliquot is then removed and placed in a 50 ml. beaker containing 10 ml. of distilled water. This sample is then titrated using 0.01N NaOH to pH 7.0 using a Beckman zeromatic pH meter. Volume, titratable acidity (meg.L) and total acid output ($\mu$eg/hour) are recorded. Percent inhibition is determined by comparison with the appropriate control. Groups of three rats were used for preliminary testing, and groups of six rats were used for dose-response evaluations. All compounds are administered in a vehicle consisting of 0.5% methocel, 0.4% tween 80, and saline at a constant volume of 1 ml./100 gram rat. Samples are dispersed by sonification. Percent inhibition is calculated on basis of concurrent vehicle control.

In Table B which follows is given the effect on total acid output after 120 minutes of a 10 mg./kg. dose of representative ketals of this invention. For comparison the result obtained with the corresponding 9-oxo derivative, 1 9-oxo-15(S)-hydroxyprostanoic acid is included. It is to be noted that it is significantly less potent than the ketals.

TABLE B

Inhibition of Total Acid Output in the Acute Gastric Fistula Rat

| Compound (10 mg./kg., intraduodenal route) | %-Inhibition of Total Acid Output After 120 Minutes |
|---|---|
| 1 9-oxo-15(S)-hydroxyprostanoic acid (12.5 mg./kg. dose) | 27 |
| 1 9,9-ethylenedioxy-15(S)-hydroxyprostanoic acid | 63 |
| 1 9,9-(1-methylethylenedioxy)-15(S)-hydroxy prostanoic acid | 61 |
| 1 9,9-(1,2-dimethylethylenedioxy)-15(S)-hydroxy-prostanoic acid | 57 |
| 1 methyl 9,9-(1,2-dimethylethylenedioxy)-15(S)-acetoxyprostanoate | 74 |
| 1 methyl 9,9-(1-chloromethylethylenedioxy)-15(S)-acetoxyprostanoate | 26 |
| 1 9,9-(1-chloromethylethylenedioxy)-15(S)-hydroxyprostanoic acid | 99 |
| 1 methyl 9,9-propylenedioxy-15(S)-acetoxy prostenoate | 60 |
| 1 9,9-(2,2-dimethyl-1,3-propylenedioxy)-15(S) hydroxyprostenoic acid | 32 |
| 1 methyl 9,9-(2,2-dimethyl-1,3-propylenedioxy)-15(S)-acetoxy-prostenoate | 27 |
| 1 9,9-ethyleneoxythia-15(S)-hydroxyprostanoic acid | 39 |
| 1 methyl 9,9-ethylenedithia-15(S)-acetoxy-prostanoate | 32 |
| 1 methyl 9,9-ethylenedioxy-15(S)-acetoxy-prostanoate | 100 ($ED_{50}$ = 3.0 mg./kg.) |

Dose response evaluation in the acute gastric fistual rat assay further illustrates the pronounced advantage of the novel ketals of this invention as gastric acid secretion inhibitors relative to the corresponding 9-oxo derivative. This is illustrated in Table C below wherein the ketals are as much as 17 times more potent then the ketone.

TABLE C

Inhibition of Total Acid Output in the Acute Gastric Fistula Rat

| | $ED_{50}$ (mg./kg., intraduodenal route of administration) | | Ileal-Ligated Rat Assay | |
|---|---|---|---|---|
| | 1 hr. collection (A) | 2 hr. collection (B) | Intraduodenal Dose mg./kg. | Increase in weight of intestine. |
| 1 9-oxo-15(S)-hydroxyprostanoic acid | 18 | >25 | 10.0 / 5.0 | 1.02 / 0.1 |
| 1 9,9-ethylenedioxy-15(S)-hydroxyprostanoic acid | 1 | 2.3 | 10.0 / 5.0 | 0.46 / 0.03 |
| 1 9,9-(1,2-dimethylethylenedioxy-15(S)-hydroxy prostanoic acid | <8 | 8 | 10.0 / 20.0 | 0.65 / −0.4 |
| 1 methyl 9,9-(1,2-dimethylethylenedioxy)-15(S)-acetoxy-prostanoate | 7 | 7 | 10.0 / 20.0 | 0.2 / 0.87 |
| 1 9,9-(1-chloromethylethylenedioxy)-15(S)-hydroxy-prostanoic acid | 6 | 6 | 10.0 / 20.0 | 0.33 / −0.26 |
| 1 methyl 9,9-(1,3-propylenedioxy)-15(S)-acetoxy-prostanoate | 6 | 6 | | |
| 1 methyl 9,9-ethylenedioxy-15(S)-acetoxy-prostanoate | | 3.0 | | |

An important consideration in the use of prostaglandin like substances for the inhibition of gastric acid secretion and the treatment of ulcers, etc. is that they do not at the same time induce diarrhea, a common phenomonen observed on administration of the prostaglandins. It is therefore unexpected and novel that in general, the compounds of this invention are not diarrheagenic at dose levels at which they are effective gastric acid secretion inhibitors. One measure of diarrheagenic potential is the ileal ligated rat assay, a description of which follows directly.

Female Sprague-Dawley rats (Charles River Laboratories) weighing less than 100 grams are fasted in individual cages for at least 18 hours. They are then anesthetized with ether and a midline incision made. The duodenum is exposed and the test drug or control injected intraduodenally. The ileocecal junction is then exposed and the terminal ileum is ligated using 3–0 silk thread just proximal to the junction. The incision is then closed using wound clips. Rats are placed back in individual cages without food or water for 4 hours. After this time the rats were sacrificed, the stomach and small intestine carefully removed, and cleaned of adherent mesentery. The removed portion of gut is then weighed to the nearest 0.1 gram. Compounds inducing diarrhea such as prostaglandins, cholera toxin, etc. produce an increase in weight of the ligated intestine. This increase from control is noted in Table C, as change in weight in grams after standardizing weights of gut to grams/100 gram rat.

When compound by this assay at effective gastric acid secretion inhibiting doses, as determined by the acute rat fistula assay, the novel ketals of Table C are non-diarrheagenic, whereas the corresponding ketone is diarrheagenic at 10 mg./kgg. dose, substantially lower than its $ED_{50}$ for inhibition of gastric acid secretion, see Table C.

Gastric acid secretion inhibition can also be observed in an assay wherein acid secretion is stimulated as in the well-known "Shay-rat" procedure, which is carried out in the following manner.

The rats (male, CFE strain) were starved for 48 hours (water was given ad libitum) to permit evacuation of stomach contents. On the morning of the experiment, under ether anesthesia, the abdominal region was shaved and a midline incision (1–1½ inch) was made with a scapel. With the help of a closed curved hemostat the duodenum was picked up. Upon getting the duodenum into view, fingers were used to pull the stomach through the opening, the stomach was then gently manipulated with fingers to rid stomach of air and residual matter which were pushed through the pylorus. Two 5-inch sutures were drawn under the pyloric-duodenal puncture. A ligature, at the juncture, was formed with one of the threads. The second ligature was also formed but not tightened.

The test compound or the vehicle, usually 1 ml./100 g. body weight, were injected into the duodenum as close as possible to the first ligature. After injection the second ligature was tightened below the injection site to minimize leakage. The stomach was placed back through the opening into the abdominal cavity, the area of incision was washed with saline and the incision was closed with autoclips. (Occasionally, instead of an intraduodenal injection, animals were dosed by the oral or subcutaneous route. In the latter case, dosing was done 30 to 60 minutes before the operation.)

Three hours later, the rats were decapitated and exanguinated, taking care that blood did not drain into the esophagus. The abdominal cavity was exposed by cutting with scissors and the esophagus close to the stomach was clamped off with a hemostat, the stomach was removed by cutting above the hemostat (the esophagus was cut) and between the two sutures. Extraneous tissue was removed, the stomach washed with saline and blotted on gauze. A slit was carefully made in the stomach which was held over a funnel and the contents were collected in a centrifuge tube. The stomach was further cut along the outside edge and turned inside out. Two ml. distilled $H_2O$ were used to wash the stomach contents into the respective centrifuge tube. The combined stomach contents and wash were then centrifuged out for 10 minutes in the International Size 2 Centrifuge (setting at 30). The supernatant was collected, volume measured and recorded, 2 drops of a phenolphthalein indicator (1% in 95% ethanol) were added and the solution was tritrated with 0.02N NaOH (or with 0.04N NaOH when large volumes of stomach contents were encountered) to pH 8.4 (because of usual coloring of the stomach contents, phenolphthalein was only used to permit visual indication that the end point was near) and the amount of acid present was calculated.

Compouns inducing inhibition of gastric acid secretion of 20% or more were considered active. In a representative operation, and merely by way of illustration, the results obtained with this assay with a typical compound of the present invention are given in Table D below.

TABLE D

| Compound | Intraduodenal Dose; mg./kg. of body weight | Percent Inhibition |
| --- | --- | --- |
| 9,9-ethylenedioxy-15-hydroxyprostanoic acid | 100 | 56 |

This invention will be described in greater detail in conjunction with the following specific examples.

EXAMPLE 1

Preparation of 2-carbalkoxy(methyl/ethyl)-2-(4-carbethoxybutyl)-cyclopentan-1-one To a stirred solution of the sodium cyclopentanone carboxylate enolate in dimethoxyethane, prepared from 187 g. (1.248 moles) of 2-cyclopentanone carboxylate (mixed methyl and ethyl esters), 52.4 g. (1.248 moles) sodium hydride (57.2% in mineral oil) and 1.6 l. of dimethoxyethane, is added dropwise 309 g. (1.212 moles) of ethyl 5-iodovalerate. The reaction mixture is stirred and heated at reflux for 18 hours. The mixture is cooled and filtered. The solvent is removed from the filtrate by evaportion and the residue is poured into dilute hydrochloric acid and extracted with ether. The combined extracts are washed with water and saline, dried over magnesium sulfate and evaporated to give an oil. The oil is distilled under reduced pressure to give 274 g. of a light yellow oil, b.p. 140°–143° C. (0.17 mm).

EXAMPLE 2

Preparation of 2-(4-carboxybutyl)cyclopentan-1-one

A stirred mixture of 274 g. of 2-carbalkoxy(mixed methyl and ethyl esters)-2-(4-carbethoxybutyl)cyclopentan-1-one (Example 1), 600 ml. of 20% hydrochloric acid and 325 ml. of acetic acid is heated at reflux for 20 hours. Solution occurs in approximately ½ hour. The solution is cooled and diluted with water and extracted with ether. The combined extracts are washed with saline and dried over magnesium sulfate and evaporated. The residue is evaporated twice with toluent to give 144 g. of an oil.

EXAMPLE 3

Preparation of 2-(4-carbethoxybutyl)cyclopentan-1-one

A stirred solution of 124 g. (0.673 mole) of 2-(4-carboxybutyl)cyclopentan-1-one (Example 2), 800 ml. of ethanol and 1 g. of p-toluenesulfonic acid monohydrate is heated at reflux for 18 hours. The solvent is evaporated and the residue is dissolved in ether. The ether solution is washed with saline, dilute sodium bicarbonate solution and again with saline, dried over magnesium sulfate and evaporated. The oil is distilled under reduced pressure to give 149 g. of a colorless oil, b.p. 106°–109° C. (0.23 mm).

EXAMPLE 4

Preparation of 2-carbalkoxy(methyl/ethyl)-2-(3-carbethoxypropyl)-cyclopentan-1-one In the manner described in Example 1, treatment of 2-cyclopentanone carboxylate (mixed methyl and ethyl esters) with sodium hydride in dimethoxyethane followed by ethyl 4-iodobutyrate gives a yellow oil, b.p. 136°–137° C (0.16 mm).

EXAMPLE 5

Preparation of 2-(3-carboxypropyl)cyclopentan-1-one

In the manner described in Example 2, treatment of 2-carbalkoxy(mixed methyl and ethyl esters)-2-(3-carbethoxypropyl)cyclopentan-1-one (Example 4) with a 20% hydrochloric acid and acetic acid mixture gives a yellow oil.

EXAMPLE 6

Preparation of 2-(3-carbethoxypropylcyclopentan-1-one

In the manner described in Example 3, treatment of 2-(3-carboxypropyl)cyclopentan-1-one (Example 5) with p-toluene-sulfonic acid monohydrate in ethanol gives a colorless oil, b.p. 93° C (0.10 mm).

EXAMPLE 7

Preparation of ethyl and methyl 2-(6-carbethoxyhexyl)-1-cyclopentanon-2-carboxylate In the manner described in Example 1, ethyl and methyl 2-cyclopentanone carboxylate is reacted with ethyl 7-bromoheptanoate to furnish the subject product, b.p. 147° C. (0.09 mm).

EXAMPLE 8

Preparation of 2-(6-carboxyhexyl)cyclopentan-1-one

In the manner described in Example 2, ethyl and methyl 2-(6-carbethoxyhexyl)-1-cyclopentanone-2-carboxylate (Example 7) is hydrolyzed to furnish the subject product, b.p. 143° C. (0.05 mm).

EXAMPLE 9

Preparation of 2-(6-carbethoxyhexyl)cyclopentan-1-one

In the manner described in Example 3, 2-(6-carboxyhexyl)cyclopentan-1-one (Example 8) is esterified to furnish the subject product, b.p. 110° C. (0.03 mm).

EXAMPLE 10

Preparation of 1-acetoxy-2-(6-carbethoxyhexyl)cyclopent-1-one

A stirred solution of 100 g. of 2-(6-carbethoxyhexyl)-cyclopentan-1-one (Example 9) in 250 ml. of acetic anhydride containing 0.940 g. of p-toluenesulfonic acid monohydrate is heated to boiling under partial reflux allowing distillate at 118° C. or less (i.e., acetic acid) to escape through a Vigreaux column equipped with a conductor to collect the distillate. After 16 hours, during which period acetic anhydride is added in portions in order to keep the solvent level at at least 100 ml., the solution is cooled and poured cautiously into a stirred cold mixture of saturated sodium bicarbonate solution (400 ml.) and hexane (250 ml.). The resulting mixture is stirred for an additional 30 minutes during which period solid sodium bicarbonate is added periodically to insure a basic solution. The hexane layer is separated and washed with saturated sodium chloride solution, dried with anhydrous magnesium sulfate and taken to dryness. Distillation of the residual oil gives 102 g. (87%) of pale yellow oil, b.p. 118° C. (0.07 mm).

EXAMPLE 11

Preparation of 1-acetoxy-2-(3-carbethoxypropyl)cyclopent-1-one

In the manner described in Example 10, treatment of 2-(3-carbethoxypropyl)cyclopentan-1-one (Example 6) with acetic anhydride and p-toluenesulfonic acid monohydrate gives a yellow oil, b.p. 98°–103° C. (0.35 mm).

EXAMPLE 12

Preparation of 1-acetoxy-2-(4-carbethoxybutyl)cyclopent-1-one

In the manner described in Example 10, treatment of 2-(4-carbethoxybutyl)cyclopentan-1-one (Example 3) with acetic anhydride and p-toluenesulfonic acid monohydrate gives a yellow oil, b.p. 109°–110° C. (0.37 mm).

EXAMPLE 13

Preparation of 2-(6-carbethoxyhexyl)cyclopent-2-en-1-one

To a rapidly stirred mixture of 50 g. of 1-acetoxy-2-(6-carboethoxyhexyl)cyclopent-1-one (Example 10) in 150 ml. of chloroform, 200 ml. of water and 18.8 g. of calcium carbonate, cooled in an ice bath, is added dropwise over a period of about 30 minutes, a solution of 30 g. of bromine in 50 ml. of carbon tetrachloride. After stirring for an additional 45 minutes the chloroform layer is separated and washed successively with dilute sodium thiosulfate solution, saturated sodium chloride solution, dried with anhydrous magnesium sulfate and taken to dryness under reduced pressure.

The residual oil is dissolved in 50 ml. of N,N-dimethylformamide and added to a mixture of 33 g. of lithium bromide and 32 g. of lithium carbonate in 375 ml. of N,N-dimethylformamide, previously dried by refluxing with 375 ml. of benzene under a Dean-Stark apparatus followed by distillation of the benzene. The mixture is stirred at the reflux temperature for 30 minutes, then cooled and poured into 850 ml. of ice-cold water. The resulting mixture is acidified (cautiously) with 4N hydrochloric acid and extracted with ether three times.

The combined ether extracts are washed with saturated sodium chloride solution, dried with anhydrous magnesium sulfate and taken to dryness under reduced pressure to afford 41.5 g. of an amber oil. In order to convert any isomeric material to the desired product, 41.5 g. of the above material is treated with 0.500 g. of p-toluenesulfonic acid monohydrate in 450 ml. of absolute alcohol at the reflux temperature for 18 hours. The solution is taken to dryness under reduced pressure. The resulting gum is dissolved in ether and washed with saturated sodium bicarbonate solution, saturated sodium chloride solution, dried with anhydrous magnesium sulfate and taken to dryness under reduced pressure. The residual oil is distilled to give 30.2 g. of product; b.p. 118° C. (0.05 mm); $\lambda_{max}^{McOH}$ 229 m$\mu$ ($\epsilon$9950); $\lambda_{max}$ 5.75, 5.85, 6.15, 8.45 $\mu$; vapor phase chromatography shows 99% product, containing 1% 2-(6-carbethoxyhexyl)cyclopentan-1-one.

This product can be purified by the following procedure. A mixture of 120 g. of 2-(6-carbethoxyhexyl)-2-cyclopentenone, containing approximately 5% of the saturated analogue, and 7.67 g. (10 mole percent) of p-carboxyphenylhydrazine in 400 ml. of absolute ethanol is stirred at ambient temperatures for 18 hours and is then refluxed for 1 hour. The mixture is cooled, the solvent is evaporated, and the residue is taken up into 150 ml. of chloroform and passed through a column of 450 g. of aluminum oxide (Merck). The filtrate is evaporated to yield a colorless oil containing <0.5% of the saturated impurity.

EXAMPLE 14

Preparation of
2-(3-carbethoxypropyl)cyclopent-2-en-1-one

In the manner described in Example 13, bromination of 1-acetoxy-2-(3-carbethoxypropyl)cyclopent-1-one (Example 11) followed by dehydrobromination with lithium bromide and lithium carbonate is productive of the subject compound.

EXAMPLE 15

Preparation of
2-(4-carbethoxybutyl)cyclopent-2-en-1-one

In the manner described in Example 13, treatment of 1-acetoxy-2-(4-carbethoxybutyl)cyclopent-1-one (Example 12) with bromine and subsequent treatment of the brominated product with a mixture of lithium bromide and lithium carbonate in N,N-dimethylformamide is productive of the subject compound. Treatment of this product with p-carboxyphenylhydrazine by the procedure of Example 13 furnishes a product which contains less than 0.5% of the corresponding saturated ketone.

EXAMPLE 16

Preparation of
1-methoximino-2-(6-carbethoxyhexyl)-2-cyclopentene

To a mixture of 35.97 g. (0.151 mole) of 2-(6-carbethoxyhexyl)-2-cyclopentenone (Example 13) and 15.0 g. (0.180 mole) of methoxyamine hydrochloride in 300 ml. of absolute ethanol is added 25 ml. of pyridine and the resulting solution is stirred for 20 hours at ambient temperatures. The solvent is evaporated and the residue is partitioned between water and diethyl ether. The organic phase is washed with water and saturated brine, dried ($Na_2SO_4$), and the solvent is evaporated to yield an oil. Distillation yields 38.7 g. of a colorless oil, b.p. 115°–118° C. (0.075 mm). IR (film); 1740, 1627, 1053, 890 cm$^{-1}$. $\lambda$ max (MeOH) 243 (13,000). NMR$\delta$(CDCl$_3$): 3.89.

EXAMPLE 17

Preparation of
1-methoximino-2-(7-hydroxyheptyl)-2-cyclopentene

To an ice cooled solution of 34.10 g. (0.128 mole) of 1-methoximino-2-(6-carbethoxyhexyl)-2-cyclopentene (Example 16) in 200 ml. of benzene under nitrogen is added dropwise 225 ml. of a 25% solution of diisobutyl aluminum hydride in hexane. The resulting solution is stirred for 2 hours at 0°–5° C., poured onto ice and dilute hydrochloric acid, and the aqueous phase is saturated with sodium chloride. The organic phase is separated, washed with saturated brine, dried ($Na_2SO_4$), and evaporated to yield an oil. The latter is dissolved in 100 ml. of hot hexane and cooled to yield 24.3 g. of crystals, m.p. 62°–64° C. IR (KBr) 3260, 1630, 1059, 893 cm$^{-1}$. $\lambda_{max}$ 243 (14,200). NMR (CDCl$_3$) $\delta$: 2.37.

EXAMPLE 18

Preparation of
1-methoximino-2-(7-p-toluenesulfonyloxyheptyl)-2-cyclopentene

To a solution of 5.00 g. (0.0222 mole) of 1-methoximino-2-(7-hydroxyheptyl)-2-cyclopentene (Example 17) in 50 ml. of dry pyridine at 0° C. is added 8.45 g. (0.0444 mole) of p-toluene-sulfonyl chloride and the resulting solution is chilled at 5° C. overnight. The mixture is partitioned between 300 ml. of ice water and diethyl ether. The organic phase is washed with 1:1 ice cold hydrochloric acid, cold water, and cold saturated brine, dried (NaSO$_4$/K$_2$COhd 3), and evaporated under reduced pressure at room temperature to yield an oil. The latter is dissolved in 600 ml. of hexane, treated with 0.5 g. of Darco, filtered and evaporated to yield 7.7 g. of a colorless oil. IR (film) 1600, 1192, 1182, 1053, 890 cm$^{-1}$. $\lambda_{max}$ (MeOH) 228 and 243.

EXAMPLE 19

Preparation of
1-methoximino-2-(8,8-dicarbethoxyoctyl)-2-cyclopentene

To an alcoholic solution of sodiodiethyl malonate, prepared from 0.847 g. (0.0368 g. atoms) of sodium, 100 ml. of absolute ethanol, and 7.05 g. (0.0440 mole) of diethyl malonate is added 7.7 g. of the tosylate of Example 18 and the mixture is refluxed for 2 hours under a nitrogen atmosphere. The mixture is partitioned between cold dilute hydrochloric acid and diethyl ether, and the organic phase is washed with water and saturated brine, dried ($Na_2SO_4$), and evaporated to yield an oil. The excess diethyl malonate is distilled off under reduced pressure to yield 6.45 g. of a yellowish oil. IR (film) 1755, 1728, 1625, 1054, 890 cm$^{-1}$.

EXAMPLE 20

Preparation of
1-methoximine-2-(8,8-dicarboxyoctyl)-2-cyclopentene

A mixture of 6.45 g. of the diester of example 19 and 6.72 g. of potassium hydroxide in 150 ml. of 1:1 aqueous methanol is refluxed for 1 hour, cooled, and is partitioned between water and diethyl ether. The aqueous phase is acidified with hydrochloric acid, extracted with ether, and the organic phase is washed with water and saturated brine, dried ($Na_2SO_4$) and evaporated to yield a solid. The solid is crystallized from benzene to yield 4.15 g. of tan crystals, m.p. 135°–137° C. (—$CO_2$).

EXAMPLE 21

Preparation of
1-methoximino-2-(8carboxyoctyl)-2-cyclopentene

A solution of 3.926 g.(0.0126 mole) of the diacid of Example 20 in 20 ml. of xylene is refluxed for 1.5 hours, cooled, and evaporated to yield a tan solid. IR (KBr) 1720, 1618, 1179, 1050, 986 cm$^{-1}$.

EXAMPLE 22

Preparation of 2-(8-carboxyoctyl)cycopent-2-en-1-one

The acid methoxime from Example 21 is refluxed for 5hours with 55 ml. of acetone and 20 ml. of 2N hydrochloric acid. The mixture is cooled, the solvent is evaporated, and the residue is partitioned between water and diethyl ether. The organic phase is washed with water and saturated brine, dried ($Na_2SO_4$), and evaporated to yield a tan solid. IR (KBr) 1745, 1665 cm$^{-1}$. $\lambda_{max}$ (MeOH) 228 (12,600).

EXAMPLE 23

Preparation of
2-(8-carbethoxyoctyl)cyclopent-2-en-1-one

The acid ketone from Example 22 is Fisher esterified with 100 ml. of absolute ethanol, 100 ml. of benzene, and 20 mg. of p-toluenesulfonic acid for 6 hours, cooled, and the solvent is evaporated. The resulting oil is dissolved in 3:1 benzene-ether and the solution is passed through a column of 100 g. of Florisil. The filtrate is evaporated and the residue is distilled to yield 2.97 g. of a colorless oil, b.p. 137°–139° C. (0.05 Torr).

EXAMPLE 24

Preparation of
1-methoximine-2-(5-cyanopentyl)-2-cyclopentene

A mixture of 2.75 g. (0.01 mole of 1-methoximino-2-(5-methanesulfonyloxypentyl)-2-cyclopentene (Example 23) and 1.47 g. (0.03 mole) of sodium cyanide in 20 ml. of dry N,N-dimethylformamide is heated at 65°–70° C. for 3 hours. The cooled reaction mixture is poured into water and extracted with diethyl ether. The organic phase is washed with water and saturated saline solution, dried ($MgSO_4$), and evaporated to give 1.89 g. of a light yellow oil.

EXAMPLE 25

Preparation of
1-methoximine-2-(5-carboxypentyl)-2-cyclopentene

A mixture of 1.89 g. (0.0092 mole) of 1-methoximino

A mixture of 1.89 g. (0.0092 mole) of 1-methoximino-2-(5-cyanopentyl)-2-cyclopentene (Example 24) and 1 g. (0.025 mole) of sodium hydroxide in 50 ml. of 1:1 aqueous-ethanol is refluxed for 48 hours, cooled, and partitioned between water and diethyl ether. The aqueous phase is acidified with hydrochloric acid, extracted with diethyl ether, and the organic phase is washed with water and saturated saline solution, dried ($MgSO_4$), and evaporated to give 1.86 g. of a yellow oil.

EXAMPLE 26

Preparation of 2-(5-carboxypentyl)-2-cyclopentenone

A solution of 1.86 g. (0.00825 mole) 1-methoximino-2-(5-carboxypentyl)-2-cyclopentene (Example 25) in 44 ml. of acetone and 13.1 ml. of 2N hydrochloric acid is refluxed for 5 hours. The solvent is partially evaporated and a solid precipitates and is collected. The residue is extracted with diethyl ether and the organic phase is washed with saturated saline solution, dried ($MgSO_4$), and evaporated to yield additional solid. The combined solid material is crystallized from ether/pet ether (30°–60°C°) to yield crystalline material, m.p. 70°–72° C.

EXAMPLE 27

Preparation 2-(5-carbethoxypentyl)-2-cyclopentenone

A solution of 1.309 g. (0.00668 mole) of 2-(5-carboxypentyl)-2-cyclopentenone (Example 26) and 90 mg. of p-toluensulfonic acid in 150 ml. of ethanol is refluxed for 18 hours. The solvent is evaporated and the residue is dissolved in ether. The organic phase is washed with water, sodium bicarbonate solution, and saturated saline solution, dried ($MgSO_4$), and evaporated to give 1.371 g. of a light yellow oil.

EXAMPLE 28

Preparation of
2-(5-acetoxypentyl)-2-carbomethoxy/carbethoxy-cyclopentanone

A mixture of sodiocyclopentanone carboxylate, prepared from 1200 g. (8.0 mole) of cyclopentanone carboxylate (methyl and ethyl esters) and 200 g. (8.3 moles) of mineral oil free sodium hydride in 10 l. of 1,2-dimethoxyethane, 1320 g. (8.0 moles) of 5-chloro-1-amyl acetate [M.E. Synerholm, *Journ. Amer. Chem. Soc.*, 69, 2681 (1947)], and 1200 g. (8.0 moles) of sodium iodide is refluxed under nitrogen for 18 hours. The mixture is cooled, concentrated to 4 l. and partitioned between dilute hydrochloric acid and diethyl ether. The organic phase is washed with water and saturated brine, dried ($MgSO_4$), and evaporated to yield 1920 g. of an oil.

EXAMPLE 29

Preparation of
2-(5-hydroxypentyl)cyclopentanone/2-(5-acetoxypentyl)-cyclopentanone A mixture of 4,500 g. (16.2 moles) of 2-(5-acetoxypentyl)-2-carbomethoxy/carboethoxy-cyclopentanone (Example 28, 2.2 l. glacial acetic acid, 1 l. of concentrated hydrochloric acid, and 1 l. of water is refluxed for 18 hours, cooled, and partitioned between saturated brine and benzene. The organic phase is washed with saturated brine, dried ($MgSO_4$), and evaporated in vacuo to yield 3155 g. of an oil.

EXAMPLE 30

Preparation of
1-acetoxy-2-(5-acetoxypentyl)-1-cyclopentene

A solution of 400 g. (2.04 moles) of a mixture of 2-(5-hydroxypentyl)cyclopentanone and 2-(5-acetoxypentyl)cyclopentanone (Example 29) and 4.0 g. of p-toluenesulfonic acid monohydrate in 1 l. of acetic anhydride is refluxed at a rate to maintain a steady distillation of acetic acid from the reaction through a helix-packed fractionation column. The reaction is continued with the addition of acetic anhydride to maintain a constant volume until complete conversion of starting materials to product is evident. The mixture is cooled and partitioned between 2 l. of hexane and 3 l. of cold water containing solid sodium bicarbonate to maintain a neutral pH. The organic phase is washed with saturated brine, dried (MgSO$_4$), and evaporated to yield 452 g. of an oil.

EXAMPLE 31

Preparation of 2-(5-acetoxypentyl)-2-cyclopentenone

To a well stirred mixture of 405 g. (4.05 moles) of calcium carbonate, 3 l. of water, and 2.5 l. of chloroform cooled to 5° C. is added simultaneously 1016 g. (4.0 moles) of 1-acetoxy-2-(5-acetoxy-pentyl)-1-cyclopentene (Example 30) and a solution of 648 g. (4.05 moles) of bromine in 500 ml. of carbon tetrachloride at a rate to maintain a temperature below 10° C. The mixture is stirred for half an hour after addition of the reagents and the phases are then separated. The organic phase is washed with 2% sodium thiosulfate solution, water, and saturated brine, dried (MgSO$_4$), and evaporated in vacuo to an oil. The oil is immediately added to a refluxing slurry of 500 g. (5.0 moles) of calcium carbonate in 2.5 l of N,N-dimethylacetamide under nitrogen and the mixture is then refluxed for 30 minutes. The mixture is cooled, filtered, partitioned between water and diethyl ether. The organic phase is washed with water and saturated brine, dried (MgSO$_4$), and evaporated to yield 757 g. of an oil, b.p. 116°–118° C. (0.25 mm.).

EXAMPLE 32

Preparation of 1-methoximino-2-(5-acetoxypentyl)-2-cyclopentene

In the manner described for Example 16, 2-(5-acetoxypentyl)-2-cyclopentenone (Example 31) is treated with methoxyamine hydrochloride in pyridine and ethanol to yield the subject compound, b.p. 101°–103° C. (0.20 mm.).

EXAMPLE 33

Preparation of 1-methoximino-2-(5-hydroxypentyl)-2-cyclopentene

A mixture of 74 g. (0.22 mole) of 1-methoximino-2-(5-acetoxypentyl)-2-cyclopentene (Example 32) and 56 g. (1.0 mole) of potassium hydroxide in 300 ml. of 1:1 aqueous methanol is refluxed for 2 hours and then cooled. The solvent is partially removed in vacuo and the residue is partitioned between saturated brine and diethyl ether. The organic phase is washed with saturated brine, dried (MgSO$_4$), and evaporated to yield an oil which crystallized, m.p. 35°–36° C.

EXAMPLE 34

Preparation of 1-methoximine-2-(5-methanesulfonyloxypentyl)-2-cyclopentene

To a cold solution of 9.85 g. (0.05 mole) of 1-methoximino-2(5-hydroxypentyl)-2-cyclopentene Example 33) and 7.6 g. (0.075 mole) of triethylamine in 100 ml. of methylene chloride at −10° C. is added 6.3 g. (0.055 mole) of methanesulfonyl chloride at a rate to maintain a temperature of −10° to 0° C. The mixture is then stirred for 15 minutes and then poured into ice water. The organic phase is washed with cold 10% hydrochloric acid, cold saturated sodium bicarbonate solution, and cold saturated brine, dried (MgSO$_4$), and evaporated to yield a solid, m.p. 78°–80° C.

EXAMPLE 35

Preparation of 1-methoximino-2-(6,6-dicarbethoxyhexyl)-2-cyclopentene

To a suspension of sodiodiethylmalonate in 1,2-dimethoxyethane, prepared from 248 g. (1.55 moles) of diethyl malonate and 17.2 g. (0.95 mole) of mineral oil free sodium hydride in 1 l. of 1,2-dimethoxyethane under nitrogen, is added 170 g. (0.62 mole) of 1-methoximino-2-(5-methanesulfonyloxypentyl)-2-cyclopentene (Example 34) in 1.5 l. of 1,2-dimethoxyethane and the mixture is refluxed for 5 hours. The mixture is cooled, filtered, and the solvent is evaporated. The residue is partitioned between cold dilute hydrochloric acid and water, and the organic phase is washed with saturated brine, dried (MgSO$_4$), and evaporated to remove solvent and excess diethyl malonate to yield 209 g. of an oil.

EXAMPLE 36

Preparation of 1-methoximino-2-(6,6-dicarboxyhexyl)-2-cyclopentene

In the manner described in Example 20, 1-methoximino-2-(6,6-dicarbethoxyhexyl)-2-cyclopentene is treated with potassium hydroxide in 1:1 aqueous methanol and then hydrochloric acid to yield the desired compound as crystals from diethyl ether, m.p. 110°–115° C.

EXAMPLE 37

Preparation of 1-methoximino-2-(6-carboxyhexyl)-2-cyclopentene

A solution of 141 g. (0.50 mole) of 1-methoximino-2-(6,6-dicarboxyhexyl)-2-cyclopentene in 500 ml. of bis-(2-methoxyethyl) ether is refluxed for 2 hours, cooled, and evaporated to yield an oil. The latter is crystallized from hexane to yield 92 g. of solid, m.p. 70°–72° C.

EXAMPLE 38

Preparation of 2-(6-carboxyhexyl)-2-cyclopentenone

In the manner described in Example 22, treatment of 1-methoximino-2-(6-carboxyhexyl)-2-cyclopentene (Example 37) with acetone and 2N hydrochloric acid at reflux provides the subject compound.

EXAMPLE 39

Preparation of 2-(6-carbethoxyhexyl)-2-cyclopentenone

Fischer estification of 2-(6-carboxyhexyl)-2-cyclopentenone (Example 38) in the manner of Example 23 provides the subject compound.

EXAMPLE 40

Preparation of 2-(7-cyanoheptyl)-1-methoximino-2-cyclopentene

Treatment of 1-methoximino-2-(7-p-toluenesulfonyloxy)-2-cyclopentene (Example 18) with sodium cyanide in the manner of Example 24 is productive of the subject compound.

EXAMPLE 41

Preparation of 2-(7-carboxyheptyl)-1-methoximino-2-cyclopentene

Alkaline hydrolysis of 2-(7-cyanoheptyl)-1-methoximino-2-cyclopentene (Example 40) by the procedure of Example 25 is productive of the subject compound.

EXAMPLE 42

Preparation of 2-(7-carboxyheptyl)-2-cyclopenten-1-one

Hydrolysis of the methoxime of Example 41 with acetone-hydrochloric acid by the procedure of Example 26 is productive of the subject compound.

EXAMPLE 43

Preparation of 2-(7-carbethoxyheptyl)-2-cyclopenten-1-one

Fisher estification of the carboxylic acid of Example 42 by the procedure of Example 27 is productive of the subject compound.

EXAMPLE 44

Preparation of 2-(6-carbo-n-butoxyhexyl)cyclopent-2-en-1-one

A solution of 50 g. of 2-(6-carboxyhexyl)cyclopent-2-en-1-one [Bagli et al., Tetrahedron Letters, No. 5, 465 (1966)] in 1400 ml. of n-butanol containing 2.7 g. of p-toluenesulfonic acid monohydrate is allowed to stand at room temperature in a stoppered flask for about 24 hours. The solution is taken to dryness. The residue is taken up in ether and the ethereal solution is washed several times with saline solution, dried with anhydrous magnesium sulfate, and taken to dryness to afford the subject butyl ester.

EXAMPLES 45–47

Treatment of 2-(6-carboxyhexyl)cyclopent-2-en-1-one by the procedure of Example 44 with the appropriate alcohol affords the esters of the following table.

sulfate and evaporated to dryness. Distillation gave 13.9 g. (68%) of product, b.p. 59° C. (0.008 mm).

EXAMPLE 49

Preparation of 15-(tert-butoxy)-9-oxoprostanoic acid, ethyl ester

To a Grignard solution, prepared from 5.05 g. of magnesium and 65.8 g. of 3-(tert-butoxy)-1-iodooctane in 150 ml. of diethyl ether under nitrogen atmosphere, is added 4.0 g. of copper iodide-tri-n-butylphosphine complex followed by dropwise addition of 49 g. of 2-(6-cabethoxyhexyl)cyclopent-2-en-1-one [Hardegger et al., Helv. Chim. Acta 50, 2501 (1967)] and the resulting mixture is stirred for 18 hours. Saturated ammonium chloride (110 ml.) is added followed by 100 ml. of water and 100 ml. of diethyl ether. Unreacted magnesium is removed by filtration. The ethereal layer is washed successively with aqueous sodium thiosulfate solution, ammonium chloride solution, and water, dried over magnesium sulfate and taken to dryness to give an oil. Distillation at 0.05 mm. (bath 100°–185° C.) gives 45.4 g of material containing unreacted starting material and 30 g. (85% yield based on non-recovered starting material; see below) of residue which contains the desired product. This material is chromatographed on silica gel. The product is eluted with diethyl ether to give 25.2 g. (71% based on recovered starting material) of a syrup; this material has no significant ultraviolet absorption; $\lambda_{max}^{KBr}$ 5.74, 7.20, 7.35, 8.35 $\mu$; nmr 2H quartet $\delta$ 4.09 (OCH$_2$ of ester), 1,H broad singlet 3.57 (carbinolic proton), 5H overlapping multiplets 2.0–2.4 (protons next to C=O). 3H triplet 1.22 (CH$_3$ of ethyl), 9H singlet 1.17 (CH$_3$'s to t-butyl) and 3H triplet 0.9 (terminal methyl); mass spectrum: m/e 424

EXAMPLE 50

Preparation of 15-hydroxy-9-oxoprostanoic acid, ethyl ester

A solution of 25 g. of 15-(tert-butoxy)-9-oxoprostanoic acid, ethyl ester (Example 19) in 100 ml. of trifluoroacetic acid is stirred in an ice bath for 1 hour and is then poured into 500 ml. of ice water and extracted several times with chloroform. The combined

TABLE I

| Example | Alcohol | Product Ester |
|---|---|---|
| 45 | isopropanol | 2-(6-carboisopropoxyhexyl)cyclopent-2-en-1-one |
| 46 | methanol | 2-(6-carbomethoxyhexyl)cyclopent-2-en-1-one |
| 47 | 1-hydroxy-n-decane | 2-(6-carbo-n-decyloxyhexyl)cyclopent-2-en-1-one |

EXAMPLE 48

Preparation of 3-(tert-butoxy)-1-iodooctane

Into a solution of 16.7 g. of 1-iodo-3-octanol [Shriner et al., J. Org. Chem. 4, 103 (1939)] in 250 ml. of methylene chloride is bubbled isobutylene at a fast rate until the solution is saturated. The solution is cooled and 2 ml. of concentrated sulfuric acid is added. The solution is stoppered and allowed to stand at room temperature for 3 days. After the solution is poured into 300 ml. of 5% sodium carbonate, the organic phase is separated, washed with brine, dried with anhydrous magnesium chloroform extracts are washed with saturated sodium bicarbonate solution, saturated sodium chloride solution, dried with anhydrous magnesium sulfate, and taken to dryness. The resulting oil is dissolved in 200 ml. of 1N ammonium hydroxide in ethanol, kept at ambient temperature for 15 minutes, then taken to dryness. The residual oil is dissolved in chloroform and washed with 1N hydrochloric acid, saturated sodium chloride solution, dried and taken to dryness to give 21.7 g. (100%) of product as a yellow syrup. There is essentially no uv absorption; $\lambda_{max}^{KBr}$ 2.90, 5.75, 8.45 $\mu$; mnr 2H quartet $\delta$ 4.13 (OCH$_2$ of ester), 1H broad singlet 3.63 (carbinolic proton), 3H triplet (CH$_3$ of ester and 3H distorted triplet 0.92 (terminal methyl); mass spectrum: m/e 368.

EXAMPLE 51

Preparation of 15-hydroxy-9-oxoprostanoic acid

A suspension of 15 g. of 15-hydroxy-9-oxoprostanoic acid, ethyl ester (Example 50) in 230 ml. of aqueous methanol (1:1) containing 6.45 g. of potassium hydroxide is stirred at 50° C. for 1 hour and then at room temperature for 18 hours. The resulting solution is acidified with 1N hydrochloric acid, saturated with sodium chloride, and extracted several times wth diethyl ether. The combined ether extracts are washed twice with saturated sodium chloride solution, dried with anhydrous magnesium sulfate, and taken to dryness to give 13.1 g. (94%) of products as an oil. There is essentially no uv absorption; $[\alpha_D^{25}$ 0° (1.0% in $CHCl_3$); $\lambda_{max}^{KBr}$ 2.80–3.70 (broad), 5.75, 5.87 $\mu$; nmr 2H singlet δ6.65 (hydroxyl and carboxyl protons), 1H broad singlet 3.63 (carbinolic proton), and 3H distorted triplet 0.93 (terminal methyl); mass spectrum: m/e 340.

EXAMPLE 52

Preparation of methyl 1-15 (S)-acetoxy-9-oxo-prostanoate

A solution of 2.5 g. of methyl 15(S)-acetoxy-9-oxo-5-cis, 10,13-trans-prostatrienoate [W.P. Schneider, R.D. Hamilton, L. E. Rhuland, *Journ. Amer. Chem. Soc.*, 94, 2122 (1972)] in 150 ml. of ethyl acetate is hydrogenated using 5% rhodium-on-carbon catalyst. Removal of the catalyst by filtration followed by evaporation of the solvent gives 2.26 g. of subject compound as an oil; λ max 5.80 (carbonyl groups).

EXAMPLE 53

Preparation of methyl 1-15 (S)-hydroxy-9-oxo-prostanoate

A solution of 2.26 g. of methyl 15(S)-acetoxy-9-oxo-prostanoate (Example 52) in 300 ml. of absolute alcohol containing 790 mg. of potassium carbonate is stired at ambient temperature for 72 hours then concentrated to near dryness under reduced pressure. The resulting mixture is extracted with ether. The combined extracts are washed with saturated sodium chloride solution, dried with anhydrous magnesium sulfate and taken to dryness to give 1.83 g. of an oil. Purfication by silica gel chromatography affords the suject compound as an oil; λ max. 2.92 (hydroxyl group), 5.74 $\mu$ (carbonyl groups); $[\alpha_D^{25}$ −23° C. (0.2% in $CHCl_3$).

EXAMPLE 54

Preparation of 1-15(S)-hydroxy-9-oxo-prostanoic acid

A solution of 930 mg. of methyl 15(S)-hydroxy-9-oxo-prostanoate (Example 53) in 16 ml. of methanol-water (1:1) containing 410 mg. of potassium hydroxide is stirred at ambient temperature for 18 hours. The solution is acidified with 1N hydrochloric acid and extracted with ether. The ether extract is washed with saturated sodium chloride solution, dried with anhydrous magnesium sulfate and evaporated to dryness in vacuo to give 797 mg. of viscous oil; λ max 2.94–4.00 (broad) (hydroxyl and carboxyl groups), 5.80 (ketone carbonyl group), and 5.87 $\mu$ (acid carbonyl group); $[\alpha]_D^{25}$−23° C. (0.6% in $CHCL_3$).

EXAMPLE 55

Preparation of ethyl 9-ethylenedioxy-15-hydroxy-prostanoate

A solution of 3.4 g. of ethyl 15-hydroxy-9-oxo-prostanoate (Example 50) in 85 ml. of benzene containing 30 mg. of p-toluensulfonic acid monohydrate and 2 ml. of ethylene glycol is stirred at the reflux temperature for 18 hours. The water formed is removed by means of a Dean-Stark distilling receiver. The cooled solution is washed with 5% aqueous sodium carbonate solution, saturated sodium chloride solution, dried with anhydrous sodium sulfate and evaporated to dryness under reduced pressure to give 3.78 g. (99%) of oil; λ max. 2.93 (hydroxy group) and 5.77 β (ester carbonyl group).

EXAMPLE 56

Preparation of ethyl 9-ethylenedioxy-15-oxo-prostanoate

A solution of 8.7 g. of dry pyridine in 140 ml. of dry methylene chloride, stirred in a tap water bath is treated with 5.5 g. of dry chromium trioxide. The resulting deep red suspension is stirred at ambient temperature for 15 minutes. A solution of 3.78 g. of ethyl-9-ethylenedioxy-15-hydroxy-prostanoate (Example 55) in 15 ml. of methylene chloride is added, all at once, to the suspension. A black, tarry deposit is formed immediately. After stirring for 15 minutes at ambient temperature, the methylene chloride solution is decanted from the tarry deposit which is triturated with several portions of ether. The combined organic phases are washed with 5% aqueous sodium hydroxide, water, ice-cold 5% aqueous hydrochloric acid, saturated sodium bicarbonate solution, and saturated sodium chloride solution, dried with anhydrous magnesium sulfate and taken to dryness to give 3.29 g. (88%) of a viscous oil; λ max 5.78 and 5.86 $\mu$ (carbonyl groups).

EXAMPLE 57

Preparation of ethyl 9-ethylenedioxy-15-hydroxy-15-methyl-prostanoate

To a Grignard solution prepared from 207 mg. of magnesium and 1.3 g. of methyl iodide in 10 ml. of ether under nitrogen atmosphere is added a solution of 1.77 g. of ethyl 9-ethylenedioxy-15-oxo-prostanoate (Example 56) in 10 ml. of ether and the resulting mixture is stirred at room temperature for 18 hours. Saturated ammonium chloride (20 ml.) is added followed by 10 ml. of water and 50 ml. of ether. The ethereal solution is washed with saturated sodium chloride solution, dried with anhydrous magnesium sulfate and taken to dryness to give 1.77 g. (94%) of viscous oil; λ max. 2.94 (hydroxyl group) and 5.77 $\mu$ (carbonyl group).

EXAMPLE 58

Preparation of 9-ethylenedioxy-15-hydroxy-15-methyl-prostanoic acid

A solution of 1.33 g. of ethyl 9-ethylenedioxy-15-hydroxy-15-methyl prostanoate (Example 57) in 20 ml. of methanol-water (1:1) containing 500 mg. of potassium hydroxide is stirred at room temperature for 18 hours. The solution is neutralized with 30% aqueous sodium phosphate monobasic and extracted with ether. The ether extract is washed with saturated sodium chloride solution, dried with anhydrous magnesium sulfate and taken to dryness to give 1.23 g. (99%) of viscous oil; λ max. 2.94–4.00 (broad) (hydroxyl and carboxyl groups) and 5.85 μ (acid carbonyl group).

EXAMPLE 59

Preparation of 3-(tert-butoxy-1iodohexane

A mixture of 23.4 g. of 1-chloro-3-hexanol [Fourneau, et al., *Bull. Soc. Chem. France*, 25, 367 (1919)] in 300 ml. of 2-butanone containing 30 g. of sodium iodide is stirred at the reflux temperature for 18 hours. The cooled solution is filtered and the mother liquor is taken to dryness. Distillation of the residue affords 32.9 g. (84%) of 1-iodo-3-hexanol, b.p. 105° C. (10 mm). Treatment of this material in 500 ml. of methylene chloride, containing 4 ml. of concentrated sulfuric acid, with isobutylene according to the procedure described in Example 48 gives 27 g. of crude material. Chromatography on florisil affords 16 g. of product; λ max. 7.22 and 7.37 μ (tert-butyl group).

EXAMPLE 60–78

Treatment of the various cyclopentenone esters listed in Table II below with the 3-t-butoxyalkyl magnesium iodide, also listed in the table, in the presence of tributylphosphine cuprous iodide complex all in the manner described in Example 49 above is productive of the 15-(tert-butoxy)-9-oxo-prostanoates of the table.

TABLE 2

| Example | Starting cyclopentenone of Example | Grignard Reagent | Product 15-(tert-butoxy)-9-oxo-prostanoates |
|---|---|---|---|
| 60 | | 3-t-butoxyhexyl magnesium iodide | Ethyl 9-oxo-15-t-butoxy-19,20-dinor-prostanoate |
| 61 | 14 | '' | Ethyl 9-oxo-15-t-butoxy-5,6,7,19,20-pentanor-prostanoate |
| 62 | 15 | '' | Ethyl 9-oxo-15-t-butoxy-6,7,19,20-tetranor-prostanoate |
| 63 | 23 | '' | Ethyl 9-oxo-15-t-butoxy-7a,7b-bishomo-19,20-dinor-prostanoate |
| 64 | 27 | '' | Ethyl 9-oxo-15-t-butoxy-7,19,20-trinor-prostanoate |
| 65 | 43 | '' | Ethyl 9-oxo-15-t-butoxy-7a-homo-19,20-dinor-prostanoate |
| 66 | 44 | '' | Butyl 9-oxo-15-t-butoxy-19,20-dinor-prostanoate |
| 67 | 45 | '' | Isopropyl 9-oxo-15-t-butoxy-19,20-dinor-prostanoate |
| 68 | 46 | 3-t-butoxyhexyl magnesium iodide | Methyl 9-oxo-15-t-butoxy-19,20-dinor-prostanoate |
| 69 | 47 | '' | Decyl 9-oxo-15-t-butoxy-19,20-dinor-prostanoate |
| 70 | 14 | 3-t-butoxyoctyl magnesium iodide | Ethyl 9-oxo-15-t-butoxy-5,6,7-trinor-prostanoate |
| 71 | 15 | '' | Ethyl 9-oxo-15-t-butoxy-6,7-dinor-prostanoate |
| 72 | 23 | '' | Ethyl 9-oxo-15-t-butoxy-7a,7b-bishomo-prostanoate |
| 73 | 27 | '' | Ethyl 9-oxo-15-t-butoxy-7-nor-prostanoate |
| 74 | 43 | '' | Ethyl 9-oxo-15-t-butoxy-7a-homo-prostanoate |
| 75 | 44 | '' | Butyl 9-oxo-15-t-butoxy-prostanoate |
| 76 | 45 | '' | Isopropyl 9-oxo-15-t-butoxy-prostanoate |
| 77 | 46 | '' | methyl 9-oxo-15-t-butoxy-prostanoate |
| 78 | 47 | '' | decyl 9-oxo-15-t-butoxy-prostanoate |

EXAMPLES 79–97

Treatment of the various 15-tert-butoxyprostanoates of Table 3 below with trifluoroacetic acid in the manner of Example 50 above is productive of the corresponding 15-hydroxyprostanoates of the table.

TABLE 3

| Example | Starting 15-tert-butoxyprostanoates of example | Product 15-hydroxy-9-oxo-prostanoates |
|---|---|---|
| 79 | 52 | Ethyl 9-oxo-15-hydroxy-19,20-dinor-prostanoate |
| 80 | 53 | Ethyl 9-oxo-5-hydroxy-5,6,7,19,20-pentanor-prostanoate |
| 81 | 54 | Ethyl 9-oxo-15-hydroxy-6,7,19,20-tetranor-prostanoate |
| 82 | 55 | Ethyl 9-oxo-15-hydroxy-7a,7b-bishomo-19,20-dinor-prostanoate |
| 83 | 56 | Ethyl 9-oxo-15-hydroxy-7,19,20-trinor-prostanoate |
| 84 | 57 | Ethyl 9-oxo-15-hydroxy-7a-homo-19,20-dinor-prostanoate |
| 85 | 58 | Butyl 9-oxo-15-hydroxy-19,20-dinor-prostanoate |
| 86 | 59 | Isopropyl 9-oxo-15-hydroxy-19,20-dinor-prostanoate |
| 87 | 60 | Methyl 9-oxo-15-hydroxy-19,20-dinor-prostanoate |
| 88 | 61 | Decyl 9-oxo-15-hydroxy-19,20-dinor-prostanoate |

TABLE 3-continued

| Example | Starting 15-tert-butoxyprostanoates of example | Product 15-hydroxy-9-oxo-prostanoates |
|---------|---|---|
| 89 | 62 | Ethyl 9-oxo-15-hydroxy-5,6,7-trinor-prostanoate |
| 90 | 63 | Ethyl 9-oxo-15-hydroxy-6,7-dinor-prostanoate |
| 91 | 64 | Ethyl 9-oxo-15-hydroxy-7a,7b-bishomo-prostanoate |
| 92 | 65 | Ethyl 9-oxo-15-hydroxy-7-nor-prostanoate |
| 93 | 66 | Ethyl 9-oxo-15-hydroxy-7a-homo-prostanoate |
| 94 | 67 | Butyl 9-oxo-15-hydroxy-prostanoate |
| 95 | 68 | Isopropyl 9-oxo-15-hydroxy-prostanoate |
| 96 | 69 | Methyl 9-oxo-15-hydroxy-prostanoate |
| 97 | 70 | Decyl 9-oxo-15-hydroxy-prostanoate |

EXAMPLE 98

Preparation of l 20-ethyl-(15(S)-hydroxy-9-oxo-5-cis,10,13-trans-prostatrienoic acid A solution of l 20-ethyl-9-oxo-11α,15(S)-bis-(tetrahydropyran-2-yloxy)-5-cis-13-trans-prostadienoic acid [Pat. No. 2,150,361 (West Germany, 1972)] in tetrahydrofuran containing 1.5 N hydrochloric acid is kept at ambient temperature for 70 hours. The solution is flooded with saturated sodium chloride and extracted several times with ether. The combined extracts are washed with water, dried with anhydrous magnesium sulfate and taken to dryness to afford the subject compound.

EXAMPLE 99

Preparation of l-methyl-15(S)-hydroxy-16(R)-methyl-9-oxo-5-cis,10,13-trans-prostatrienoate An etheral solution containing a molar excess of diazomethane is added to a solution of l-15(S)-hydroxy-16(R)-methyl-9-oxo-5-cis,10,13-trans-prostatrienoic acid [M. Hayashi, et al., *Jour. Org. Chem.*, 38, 1250 (1973)] in ether (or acetone). After 2 to 4 hours, the solution is carefully evaporated under reduced pressure and the material is purified in the usual way by chromatography on silica gel to afford the subject compound.

EXAMPLE 100

Preparation of ent-methyl-15-hydroxy-9-oxo-prostanoate

In the manner described in Example 99, treatment of ent-15-hydroxy-9-oxo-prostanoic acid [Bagli, J.F., et al., Tetrahedron *Setters*, No. 35, 3329 (1973)] with diazomethane provides the subject compound.

EXAMPLES 101–106

Treatment of an etheral solution of the various prostatrienoic acids listed in Table 5 below with etheral diazomethane in the usual manner is productive of the corresponding methyl prostatrienoates of the table.

TABLE 5

| Example | Starting prostatrienoic acids | Product Methyl prostatrienoate |
|---|---|---|
| 101 | 15(S)-hydroxy-16-(R)-methyl-9-oxo-5-cis,10,13-trans-prostatrienoic acid[1] | Methyl l-15(S)-hydroxy-16(R)-methyl-9-oxo-5-cis,10,13-trans-prostatrienoate |
| 102 | 15(S)-hydroxy-16-(S)-methyl-9-oxo-5-cis,10,13-trans-prostatrienoic acid[1] | Methyl l-15(S)-hydroxy-16(S)-methyl-9-oxo-5-cis,10,13-trans-prostatrienoate |
| 103 | 15(R)-hydroxy-16-(S)-methyl-9-oxo-5-cis,10,13-trans-prostatrienoic acid[1] | Methyl l-15(R)-hydroxy-16(S)-methyl-9-oxo-5-cis,10,13-trans-prostatrienoate |
| 104 | 15(R)-hydroxy-16-(R)-methyl-9-oxo-5-cis,10,13-trans-prostatrienoic acid[1] | Methyl l-15(R)-hydroxy-16(R)-methyl-9-oxo-5-cis,10,13-trans-prostatrienoate |
| 105 | 15(S)-hydroxy-16,16-dimethyl-9-oxo-5-cis,10,13-trans-prostatrienoic acid[2] | Methyl l-15(S)-hydroxy-16,16-dimethyl-9-oxo-5-cis,10,13-trans-prostatrienoate |
| 106 | l-20-Ethyl-15(S)-hydroxy-9-oxo-5-cis,10,13-trans-prostatrienoic acid (Example 98) | Methyl l-20-ethyl-15(S)-hydroxy-9-oxo-5-cis,-10,13-trans-prostatrienoate |

[1] M. Hayashi, et al., Jour. Org. Chem., 38, 1250 (1973).
[2] Belgium Patent No. 782,822.

EXAMPLES 107–112

Hydrogenation of the various prostenoic acid methyl esters listed in Table 6 below using 5% rhodium-on-carbon catalyst in ethyl acetate all in the manner described in Example 52 above is productive of the prostanoic acid methyl esters of the table.

TABLE 6

| Example | Starting prostenoic acid methyl esters of Example | Product Prostanoic acid methyl esters |
|---|---|---|
| 107 | 101 | Methyl l-15(S)-hydroxy-16(R)-methyl-9-oxo-prostanoate |
| 108 | 102 | Methyl l-15(S)-hydroxy-16(S)-methyl-9-oxo-prostenoate |
| 109 | 103 | Methyl l-15(R)-hydroxy-16(S)-methyl-9-oxo-prostanoate |

TABLE 6-continued

| Example | Starting prostenoic acid methyl esters of Example | Product Prostanoic acid methyl esters |
|---|---|---|
| 110 | 104 | Methyl l-15(R)-hydroxy-16(R)-methyl-9-oxo-prostanoate |
| 111 | 105 | Methyl l-15(S)-hydroxy-16,16-dimethyl-9-oxo-prostanoate |
| 112 | 106 | Methyl l-20-ethyl-15(S)-hydroxy-9-oxo-prostanoate |
| 112A | dl-methyl 15-hydroxy-9-oxo-13-trans-prostenoate[1] | dl-methyl 15-hydroxy-9-oxo-prostanoate |
| 112B | dl-methyl-15-epi-hydroxy-9-oxo-13-trans-prostenoate[1] | dl-methyl 15-epi-hydroxy-9-oxoprostanoate |

[1] K.F. Bernady and M.J. Weiss, Prostaglandins, 3, 505 (1973).

EXAMPLES 113–272

Treatment of the various 9-oxo-prostanoates listed in Table 7 below with the indicated reagent, by the method described in Example 55 above, is productive of the ketals of the Table.

TABLE 7

| Example | Starting 9-oxo-prostanoates of Example | Ketalizing reagent | Product Prostanoate Ketals |
|---|---|---|---|
| 113 | 79 | Ethylene glycol | Ethyl 9,9-(ethylenedioxy)-15-hydroxy-19,20-dinor-prostanoate |
| 114 | 80 | Ethylene glycol | Ethyl 9,9-(ethylenedioxy)-15-hydroxy-5,6,7-19,20-Pentanor-prostanoate |
| 115 | 81 | Ethylene glycol | Ethyl 9,9-(ethylenedioxy)-15-hydroxy-6,7,19,20-tetranor-prostanoate |
| 116 | 82 | Ethylene glycol | Ethyl 9,9-(ethylenedioxy)-15-hydroxy-7a,7b-bishomo-19,20-dinor-prostanoate |
| 117 | 83 | Ethylene glycol | Ethyl 9,9-(ethylenedioxy)-15-hydroxy-7,19,20-trinor-prostanoate |
| 118 | 84 | Ethylene glycol | Ethyl 9,9-(ethylenedioxy)-15-hydroxy-7a-homo-19,20-dinor-prostanoate |
| 119 | 85 | Ethylene glycol | Butyl 9,9-(ethylenedioxy)-15-hydroxy-19,20-dinor-prostanoate |
| 120 | 86 | Ethylene glycol | Isopropyl 9,9-(ethylenedioxy)-15-hydroxy-19,20-dinor-prostenoate |
| 121 | 87 | Ethylene glycol | Methyl 9,9-(ethylenedioxy)-15-hydroxy-19,20-dinor-prostanoate |
| 122 | 88 | Ethylene glycol | Decyl 9,9-(ethylenedioxy)-15-hydroxy-19,20-dinor-prostanoate |
| 123 | 89 | Ethylene glycol | Ethyl 9,9-(ethylenedioxy)-15-hydroxy-5,6,7-trinor-prostanoate |
| 124 | 90 | Ethylene glycol | Ethyl 9,9-(ethylenedioxy)-15-hydroxy-6,7,-dinor-prostonate |
| 125 | 91 | Ethylene glycol | Ethyl 9,9-(ethylenedioxy)-15-hydroxy-7a,7b-bishomo-prostanoate |
| 126 | 92 | Ethylene glycol | Ethyl 9,9-(ethylenedioxy)-15-hydroxy-7-nor-prostanoate |
| 127 | 93 | Ethylene glycol | Ethyl 9,9-(ethylenedioxy)-15-hydroxy-7a-homo-prostanoate |
| 128 | 94 | Ethylene glycol | Butyl 9,9-(ethylenedioxy)-15-hydroxy-prostanoate |
| 129 | 95 | Ethylene glycol | Isopropyl 9,9-(ethylenedioxy)-15-hydroxy-prostanoate |
| 130 | 96 | Ethylene glycol | Methyl 9,9-(ethylenedioxy)-15-hydroxy-prostonate |
| 131 | 97 | Ethylene glycol | Decyl 9,9-(ethylenedioxy)-15-hydroxy-prostanoate |
| 132 | 50 | Ethylene glycol | Ethyl 9,9-(ethylenedioxy)-15-hydroxy-prostanoate |
| 133 | Methyl l-15(R)-hydroxy-9-oxo-prostanoate [R.L. Spraggins, U. of Oklahoma, Dissertation abs. 31, 3934B (1971)] | Ethylene glycol | Methyl l-9,9-(ethylenedioxy)-15(R)-hydroxy-prostanoate |
| 134 | 53 | Ethylene glycol | Methyl l-9,9-(ethylenedioxy)-15(S)-hydroxy-prostanoate |
| 135 | 101 | Ethylene glycol | Methyl l-9,9-(ethylenedioxy)-15(S)-hydroxy-16(R)-methyl-prostanoate |
| 136 | 102 | Ethylene glycol | Methyl l-9,9-(ethylenedioxy)-15(S)-hydroxy-16(S)-methyl-prostanoate |
| 137 | 103 | Ethylene glycol | Methyl l-9,9-(ethylenedioxy)-15(R)-hydroxy-16(S)-methyl- |

(Table 6-continued, right column:)

| Example | Starting prostenoic acid methyl esters of Example | Product Prostanoic acid methyl esters |
|---|---|---|
| | epi-hydroxy-9-oxo-13-trans-prostenoate[1] | 9-oxoprostanoate |

TABLE 7-continued

| Example | Starting 9-oxo-prostanoates of Example | Ketalizing reagent | Product Prostanoate Ketals |
|---|---|---|---|
| | | | prostanoate |
| 138 | 104 | Ethylene glycol | Methyl l-9,9-(ethylenedioxy)-15(R)-hydroxy-16(R)-methyl-prostanoate |
| 139 | 105 | Ethylene glycol | Methyl l-9,9(ethylenedioxy)-15(S)-hydroxy-16,16-dimethylprostanoate |
| 140 | 106 | Ethylene glycol | Methyl l-20-ethyl-9,9-(ethylenedioxy)-15(S)-hydroxyprostanoate |
| 141 | 100 | Ethylene glycol | ent-Methyl 9,9-(ethylenedioxy)-15-hydroxyprostanoate |
| 142 | 79 | 1,2-Propanediol | Ethyl 15-hydroxy-9,9(1-methylethylenedioxy)-19,20-dinor-prostanoate |
| 143 | 80 | 1,2-Propanediol | Ethyl 15-hydroxy-9,9-(1-methylethylenedioxy)-5,6,7-19,20-pentanor-prostanoate |
| 144 | 81 | 1,2-Propanediol | Ethyl 15-hydroxy-9,9-(1-methylethylenedioxy)-6,7,19,20-tetranor-prostanoate |
| 145 | 82 | 1,2-Propanediol | Ethyl 15-hydroxy-9,9-(1-methylethylenedioxy)-7a,7b-bishomo-19,20-dinor-prostanoate |
| 146 | 83 | 1,2-Propanediol | Ethyl 15-hydroxy-9,9-(1-methylethylenedioxy)-7,19,20-trinor-prostanoate |
| 147 | 84 | 1,2-Propanediol | Ethyl 15-hydroxy-9,9-(1-methylethylenedioxy)-7a-homo-19,20-dinor-prostanoate |
| 148 | 53 | 1,2-Propanediol | Methyl l-15(S)-hydroxy-9,9-(1-methylethylendioxy)-prostanoate |
| 149 | 101 | 1,2-Propanediol | Methyl l-15(S)-hydroxy-16(R)-methyl-9,9-(1-methylethylenedioxy)prostanoate. |
| 150 | 102 | 1,2-Propanediol | Methyl l-15(S)-hydroxy-16(S)-methyl-9,9-(1-methylethylenedioxy)prostanoate |
| 151 | 105 | 1,2-diol | Methyl l-15(S)-hydroxy-16,16-dioxy)prostanoate |
| 152 | 85 | 2,3-Butanediol | Butyl 9,9-(1,2-dimethylethylenedioxy)-15-Hydroxy-19,20-dinor-prostanoate |
| 153 | 86 | 2,3-Butanediol | Isopropyl 9,9-(1,2-dimethylethylenedioxy)-15-hydroxy-19,20-dinor-prostanoate |
| 154 | 87 | 2,3-Butanediol | Methyl 9,9-(1,2-dimethylethylenedioxy)-15-hydroxy-19,20-dinor-prostanoate |
| 155 | 88 | 2,3-Butanediol | Decyl 9,9-(1,2-dimethylethylenedioxy)-15-hydroxy-19,20-dinor-prostanoate |
| 156 | 89 | 2,3-Butanediol | Ethyl 9,9-(1,2-dimethylethylenedioxy)-15-hydroxy-5,6,7-trinor-prostanoate |
| 157 | 90 | 2,3-Butanediol | Ethyl 9,9-(1,2-dimethylethylenedioxy)-15-hydroxy-6,7-dinor-prostanoate |
| 158 | 53 | 2,3-Butanediol | Methyl l-9,9-(1,2-dimethylethylenedioxy)-15(S)-hydroxyprostanoate |
| 159 | 101 | 2,3-Butanediol | Methyl l-9,9-(1,2-dimethylethylenedioxy)-15(S)-hydroxy-16(R)-methyl-prostanoate |
| 160 | 102 | 2,3-Butanediol | Methyl l-9,9-(1,2-dimethylethylenedioxy)-15(S)-hydroxy-16(S)-methyl-prostanoate |
| 161 | 105 | 2,3-Butanediol | Methyl l-9,9-(1,2-dimethylethylenedioxy)-15(S)-hydroxy-16,16-dimethyl-prostanoate |
| 162 | 91 | 1-chloro-2,3-propanediol | Ethyl-9,9-(1-chloromethylethylenedioxy)-15-hydroxy-7a,7b-bishomo-prostanoate |
| 163 | 92 | 1-chloro-2,3-propanediol | Ethyl-9,9-(1-chloromethylethylenedioxy)-15-hydroxy-7-nor-prostanoate |
| 164 | 93 | 1-chloro-2,3-propanediol | Ethyl 9,9-(1-chloromethylethylenedioxy)-15-hydroxy-7a-homo-prostanoate |
| 165 | 94 | 1-chloro-2,3-propanediol | Butyl 9,9-(1-chloromethylethylenedioxy)-15-hydroxy-prostanoate |
| 166 | 95 | 1-chloro-2,3-propanediol | Isopropyl-9,9-(1-chloromethylethylenedioxy)-15-hydroxy-prostanoate |
| 167 | 96 | 1-chloro- | Methyl-9,9-(1-chloromethyl- |

TABLE 7-continued

| Example | Starting 9-oxo-prostanoates of Example | Ketalizing reagent | Product Prostanoate Ketals |
|---|---|---|---|
| | | 2,3-propane-diol | ethylenedioxy)-15-hydroxy-prostanoate |
| 168 | 97 | 1-chloro-2,3-propane-diol | Decyl 9,9-(1-chloromethylethyl-enedioxy)-15-hydroxy-prostanoate |
| 169 | 53 | 1-chloro-2,3-propane-diol | Methyl l-9,9-(1-chloromethyl-ethylenedioxy)-15(S)-hydroxy-prostanoate |
| 170 | 101 | 1-chloro-2,3-propane-diol | Methyl l-9,9-(1-chloro-methylethylenedioxy)-15(S)-hydroxy-16(R)-methyl-prostanoate |
| 171 | 102 | 1-chloro-2,3-propane-diol | Methyl l-9,9-(1-chloromethyl-ethylenedioxy)-15(S)-hydroxy-16(S)-methyl-prostanoate |
| 172 | 105 | 1-chloro-2,3-propane-diol | Methyl l-9,9-(1-chloromethyl-ethylenedioxy)15(S)-hydroxy-16,16-dimethyl-prostanoate |
| 173 | 79 | 1,3-propane-diol | Ethyl 15-hydroxy-9,9-(propyl-enedioxy)-19,20-dionor-prostanoate |
| 174 | 80 | 1,3-propane-diol | Ethyl 15-hydroxy-9,9-(propyl-enedioxy)-5,6,7,19,20-pentanor-prostanoate |
| 175 | 81 | 1,3-propane-diol | Ethyl 16-hydroxy-9,9-(propyl-enedioxy)-6,7,19,20-tetranor-prostanoate |
| 176 | 82 | 1,3-propane-diol | Ethyl 15-hydroxy-9,9-(propyl-enedioxy)-7a,7b-bishomo-19,20-dinor-prostanoate |
| 177 | 83 | 1,3-propane-diol | Ethyl 15-hydroxy-9,9-(propyl-enedioxy)-7,19,20-trinor-prostanoate |
| 178 | 84 | 1,3-propane-diol | Ethyl 15-hydroxy-9,9-(propyl-enedioxy)-7a-homo-19,20-dinor-prostanoate |
| 179 | 85 | 1,3-propane-diol | Butyl 15-hydroxy-9,9-(propyl-enedioxy)-19,20-dinor-prostanoate |
| 180 | 86 | 1,3-propane-diol | Isopropyl 15-hydroxy-9,9-(propylenedioxy)-19,20-dinor-prostanoate |
| 181 | 87 | 1,3-propane-diol | Methyl 15-hydroxy-9,9-(propylenedioxy)-19,20-dinor-prostanoate |
| 182 | 88 | 1,3-propane-diol | Decyl 15-hydroxy-9,9-(propylene-dioxy)-19,20-dinor-prostanoate |
| 183 | 89 | 1,3-propane-diol | Ethyl 15-hydroxy-9,9-(propylene-dioxy)-5,6,7-trinor-prostanoate |
| 184 | 90 | 1,3-propane-diol | Ethyl 15-hydroxy-9,9-(propylene-dioxy)-6,7-dinor-prostanoate |
| 185 | 91 | 1,3-propane-diol | Ethyl 15-hydroxy-9,9-(propylene-dioxy)-7a,7b-bishomo-prostanoate |
| 186 | 92 | 1,3-propane-diol | Ethyl 15-hydroxy-9,9-(propylene-dioxy)-7-nor-prostanoate |
| 187 | 93 | 1,3-propane-diol | Ethyl 15-hydroxy-9,9-(propylene-dioxy)-7a-homo-prostanoate |
| 188 | 94 | 1,3-propane-diol | Butyl 15-hydroxy-9,9-(propylene-dioxy)-prostanoate |
| 189 | 95 | 1,3-propane-diol | Isopropyl 15-hydroxy-9,9-(propylene-dioxy)-prostanoate |
| 190 | 96 | 1,3-propane-diol | Methyl 15-hydroxy-9,9-(propyl-enedioxy)-prostanoate |
| 191 | 97 | 1,3-propane-diol | Decyl 15-hydroxy-9,9-(propylene-dioxy)-prostanoate |
| 192 | 50 | 1,3-propane-diol | Ethyl 15-hydroxy-9,9-(propylene-dioxy)-prostanoate |
| 193 | Methyl l-15(R)-hydroxy-9-oxo-prostanoate | 1,3-propane-diol | Methyl l-15(R)-hydroxy-9,9-(propylenedioxy)-prostanoate |
| 194 | 53 | 1,3-propane-diol | Methyl l-15(S)-hydroxy-9,9-(propylenedioxy)-prostanoate |
| 195 | 101 | 1,3-propane- | Methyl l-15(S)-hydroxy-16(R)-methyl-9,9-(propylenedioxy)- |

TABLE 7-continued

| Example | Starting 9-oxo-prostanoates of Example | Ketalizing reagent | Product Prostanoate Ketals |
|---|---|---|---|
| 196 | 102 | 1,3-propane-diol | Methyl l-15(S)-hydroxy-16(S)-methyl-9,9-(propylenedioxy)-prostanoate |
| 197 | 103 | 1,3-propane-diol | Methyl l-15(R)-hydroxy-16(S)-methyl-9,9-(propylenedioxy)-prostanoate |
| 198 | 104 | 1,3-propane-diol | Methyl l-15(R)-hydroxy-16(R)-methyl-9,9-(propylenedioxy)-prostanoate |
| 199 | 105 | 1,3-propane-diol | Methyl l-15(S)-hydroxy-16,16-dimethyl-9,9-(propylenedioxy)-prostanoate |
| 200 | 106 | 1,3-propane-diol | Methyl l-20-ethyl-15(S)-hydroxy-9,9-(propylenedioxy)-prostanoate |
| 201 | 100 | 1,3-propane-diol | ent-Methyl 15-hydroxy-9,9-(propylenedioxy)-prostanoate |
| 202 | 79 | 2,2-dimethyl-1,3-pro-panediol | Ethyl 9,9-(2,2-dimethyl-propylenedioxy)-15-hydroxy-19,20-dinor-prostanoate |
| 203 | 81 | 2,2-dimethyl-1,3-pro-panediol | Ethyl 9,9-(2,2-dimethyl-propylenedioxy)-15-hydroxy-6,7,19,20-tetranor-prostanoate |
| 204 | 88 | 2,2-dimethyl-1,3-pro-panediol | Decyl 9,9-(2,2-dimethylpropyl-enedioxy)-15-hydroxy-19,20-dinor-prostanoate |
| 205 | 89 | 2,2-dimethyl-1,3-pro-panediol | Ethyl 9,9-(2,2-dimethylpropyl-enedioxy)-15-hydroxy-5,6,7-trinor-prostanoate |
| 206 | 90 | 2,2-dimethyl-1,3-pro-panediol | Ethyl 9,9-(2,2-dimethylpropyl-enedioxy)-15-hydroxy-6,7-dinor-prostanoate |
| 207 | 91 | 2,2-dimethyl-1,3-pro-panediol | Ethyl 9,9-(2,2-dimethylpropyl-enedioxy)-15-hydroxy-7a,7b-bishomo-prostanoate |
| 208 | 92 | 2,2-dimethyl-1,3-pro-panediol | Ethyl 9,9-(2,2-dimethylpropyl-enedioxy)-15-hydroxy-7-nor-prostanoate |
| 209 | 93 | 2,2-dimethyl-1,3-pro-panediol | Ethyl 9,9-(2,2-dimethylpropyl-enedioxy)-15-hydroxy-7a-homo-prostanoate |
| 210 | 94 | 2,2-dimethyl-1,3-pro-panediol | Butyl 9,9-(2,2-dimethylpropyl-enedioxy)-15-hydroxy-prostanoate |
| 211 | 97 | 2,2-dimethyl-1,3-pro-panediol | Decyl 9,9-(2,2-dimethylpropyl-enedioxy)-15-hydroxy-prostanoate |
| 212 | 53 | 2,2-dimethyl-1,3-pro-panediol | Methyl l-9,9-(2,2-dimethyl-propylenedioxy)-15(S)-hydroxy-prostanoate |
| 213 | 101 | 2,2-dimethyl-1,3-pro-panediol | Methyl l-9,9-(2,2-dimethyl-propylenedioxy)-15(S)-hydroxy-16-(R)-methyl-prostanoate |
| 214 | 105 | 2,2-dimethyl-1,3-pro-panediol | Methyl l-9,9-(2,2-dimethyl-propylenedioxy)-15(S)-hydroxy-16,16-dimethyl-prostanoate |
| 215 | 79 | 1,2-Ethane-dithiol | Ethyl 9,9-(ethylenedithia)-15-hydroxy-19,20-dinor-prostanoate |
| 216 | 80 | 1,2-Ethane-dithiol | Ethyl 9,9-(ethylenedithia)-15-hydroxy-5,6,7,19,20-pentanor-prostanoate |
| 217 | 81 | 1,2-Ethane-dithiol | Ethyl 9,9-(ethylenedithia)-15-hydroxy-6,7,19,20-tetranor-prostanoate |
| 218 | 82 | 1,2-Ethane-dithiol | Ethyl 9,9-(ethylenedithia)-15-hydroxy-7a,7b-bishomo-19,20-dinor-prostanoate |
| 219 | 83 | 1,2-Ethane-dithiol | Ethyl 9,9-(ethylenedithia)-15-hydroxy-7,19,20-trinor-prostanoate |
| 220 | 84 | 1,2-Ethane-dithiol | Ethyl 9,9-(ethylenedithia)-15-hydroxy-7a-homo-19,20-dinor-prostanoate |
| 221 | 85 | 1,2-Ethane-dithiol | Butyl 9,9-(ethylenedithia)-15-hydroxy-19,20-dinor-prostanoate |

TABLE 7-continued

| Example | Starting 9-oxo-prostanoates of Example | Ketalizing reagent | Product Prostanoate Ketals |
|---|---|---|---|
| 222 | 86 | 1,2-Ethane-dithiol | Isopropyl 9,9-(ethylenedithia)-15-hydroxy-19,20-dinor-prostanoate |
| 223 | 87 | 1,2-Ethane-dithiol | Methyl 9,9-(ethylenedithia)-15-hydroxy-19,20-dinor-prostanoate |
| 224 | 88 | 1,2-Ethane-dithiol | Decyl 9,9-(ethylenedithia)-15-hydroxy-19,20-dinor-prostanoate |
| 225 | 89 | 1,2-Ethane-dithiol | Ethyl 9,9-(ethylenedithia)-15-hydroxy-5,6,7-trinor-prostanoate |
| 226 | 90 | 1,2-Ethane-dithiol | Ethyl 9,9-(ethylenedithia)-15-hydroxy-6,7-dinor-prostanoate |
| 227 | 91 | 1,2-Ethane-dithiol | Ethyl 9,9-(ethylenedithia)-15-hydroxy-7a,7b-bishomo-prostanoate |
| 228 | 92 | 1,2-Ethane-dithiol | Ethyl 9,9-(ethylenedithia)-15-hydroxy-7-nor-prostanoate |
| 229 | 93 | 1,2-Ethane-dithiol | Ethyl 9,9-(ethylenedithia)-15-hydroxy-7a-homo-prostanoate |
| 230 | 94 | 1,2-Ethane-dithiol | Butyl 9,9-(ethylenedithia)-15-hydroxy-prostanoate |
| 231 | 95 | 1,2-Ethane-dithiol | Isopropyl 9,9-(ethylenedithia)-15-hydroxy-prostanoate |
| 232 | 96 | 1,2-Ethane-dithiol | Methyl 9,9-(ethylenedithia)-15-hydroxy-prostanoate |
| 233 | 97 | 1,2-Ethane-dithiol | Decyl 9,9-(ethylenedithia)-15-hydroxy-prostanoate |
| 234 | 50 | 1,2-Ethane-dithiol | Ethyl 9,9-(ethylenedithia)-15-hydroxy-prostanoate |
| 235 | Methyl l-15(R)-hydroxy-9-oxo-prostanoate | 1,2-Ethane-dithiol | Methyl l-9,9-(ethylenedithia)-15(R)-hydroxy-prostanoate |
| 236 | 53 | 1,2-Ethane-dithiol | Methyl l,9,9-(ethylenedithia)-15(S)-hydroxy-prostanoate |
| 237 | 101 | 1,2-Ethane-dithiol | Methyl l-9,9-(ethylenedithia)-15(S)-hydroxy-16(R)-methyl-prostanoate |
| 238 | 102 | 1,2-Ethane-dithiol | Methyl l-9,9-(ethylenedithia)-15(S)-hydroxy-16(S)-methyl-prostanoate |
| 239 | 103 | 1,2-Ethane-dithiol | Methyl l-9,9-(ethylenedithia)-15(R)-hydroxy-16(S)-methyl-prostanoate |
| 240 | 104 | 1,2-Ethane-dithiol | Methyl l-9,9-(ethylenedithia)-15(R)-hydroxy-16(R)-methyl-prostanoate |
| 241 | 105 | 1,2-Ethane-dithiol | Methyl l-9,9-(ethylenedithia)-15(S)-hydroxy-16,16-dimethyl-prostanoate |
| 242 | 106 | 1,2-Ethane-dithiol | Methyl l-20-ethyl-(9,9-ethylenedithia)-15-hydroxyprostanoate |
| 243 | 100 | 1,2-Ethane-dithiol | ent-Methyl 9,9-(ethylenedithia)-15-hydroxy-prostanoate |
| 244 | 79 | 2-Mercapto-ethanol | Ethyl 9,9-(ethyleneoxythia)-15-hydroxy-19,20-dinor-prostanoate |
| 245 | 80 | 2-Mercapto-ethanol | Ethyl 9,9-(ethyleneoxythia)-15-5,6,7,19,20-pentanor-prostanoate |
| 246 | 81 | 2-Mercapto-ethanol | Ethyl 9,9-(ethyleneoxythia)-15-hydroxy-6,7,19,20-tetranor-prostanoate |
| 247 | 82 | 2-Mercapto-ethanol | Ethyl 9,9-(ethylenoxythia)-15-hydroxy-7a,7b-bishomo-19,20-dinor-prostanoate |
| 248 | 83 | 2-Mercapto-ethanol | Ethyl 9,9-(ethyleneoxythia)-15-hydroxy-7,19,20-trinor-prostanoate |
| 249 | 84 | 2-Mercapto-ethanol | Ethyl 9,9-(ethyleneoxythia)-15-hydroxy-7a-homo-19,20-dinor-prostanoate |
| 250 | 85 | 2-Mercapto-ethanol | Butyl 9,9-(ethyleneoxythia)-15-hydroxy-19,20-dinor-prostonate |
| 251 | 86 | 2-Mercapto-ethanol | Isopropyl 9,9-(ethyleneoxythia)-15-hydroxy-19,20-dinor-prostanoate |
| 252 | 87 | 2-Mercapto-ethanol | Methyl 9,9-(ethyleneoxythia)-15-hydroxy-19,20-dinor-prostanoate |
| 253 | 88 | 2-Mercapto-ethanol | Decyl 9,9-(ethyleneoxythia)-15-hydroxy-19,20-dinor-prostanoate |
| 254 | 89 | 2-Mercapto-ethanol | Ethyl 9,9-(ethyleneoxythia)-15-hydroxy-5,6,7-trinor-prostanoate |
| 255 | 90 | 2-Mercapto-ethanol | Ethyl 9,9-(ethyleneoxythia)-15-hydroxy-6,7-dinor-prostanoate |
| 256 | 91 | 2-Mercapto- | Ethyl 9,9-(ethyleneoxythia)- |

TABLE 7-continued

| Example | Starting 9-oxo-prostanoates of Example | Ketalizing reagent | Product Prostanoate Ketals |
|---|---|---|---|
| | | ethanol | 15-hydroxy-7a,7b-bishomo-prostanoate |
| 257 | 92 | 2-Mercapto-ethanol | Ethyl 9,9-(ethyleneoxythia)-15-hydroxy-7-nor-prostanoate |
| 258 | 93 | 2-Mercapto-ethanol | Ethyl 9,9-(ethyleneoxythia)-15-hydroxy-7a-homo-prostanoate |
| 259 | 94 | 2-Mercapto-ethanol | Butyl 9,9-(ethyleneoxythia)-15-hydroxy-prostanoate |
| 260 | 95 | 2-Mercapto-ethanol | Isopropyl 9,9-(ethyleneoxythia)-15-hydroxy-prostanoate |
| 261 | 96 | 2-Mercapto-ethanol | Methyl 9,9-(ethyleneoxythia)-15-hydroxy-prostanoate |
| 262 | 97 | 2-Mercapto-ethanol | Decyl 9,9-(ethyleneoxythia)-15-hydroxy-prostanoate |
| 263 | 50 | 2-Mercapto-ethanol | Ethyl 9,9-(ethyleneoxythia)-15-hydroxyprostanoate |
| 264 | Methyl l-15(R)-hydroxy-9-oxo-prostanoate | 2-Mercapto-ethanol | Methyl l-9,9-(ethyleneoxythia)-15(R)-hydroxy-prostanoate |
| 265 | 53 | 2-Mercapto-ethanol | Methyl l-9,9-(ethyleneoxythia)-15(S)-hydroxy-prostanoate |
| 266 | 101 | 2-Mercapto-ethanol | Methyl l-9,9-(ethyleneoxythia)-15(S)-hydroxy-16(R)-methyl-prostanoate |
| 267 | 102 | 2-Mercapto-ethanol | Methyl l-9,9-ethyleneoxythia)-15(S)-hydroxy-16(S)-methyl-prostanoate |
| 268 | 103 | 2-Mercapto-ethanol | Methyl l-9,9-(ethyleneoxythia)-15(R)-hydroxy-16(S)-methyl-prostanoate |
| 269 | 104 | 2-Mercapto-ethanol | Methyl l-9,9-(ethyleneoxythia)-15-(R)-hydroxy-16(R)-methyl-prostanoate |
| 270 | 105 | 2-Mercapto-ethanol | Methyl l-9,9-(ethyleneoxythia)-15(S)-hydroxy-16,16-dimethyl-prostanoate |
| 271 | 106 | 2-Mercapto-ethanol | Methyl 20-ethyl-9,9-(ethyleneoxythia)-15(S)-hydroxy-prostanoate |
| 272 | 100 | 2-Mercapto-ethanol | ent-Methyl 9,9-(ethyleneoxythia)-15-hydroxyprostanoate |
| 272A | 112A | Ethylene-glycol | dl-methyl 9,9-(ethylenedioxy)-15-hydroxyprostanoate |
| 272B | 112A | 1,2-Pro-panediol | dl-methyl 15-hydroxy-9,9-(1-methyl-ethylenedioxy)prostanoate |
| 272C | 112A | 1-Chloro-2,3-pro-panediol | dl-methyl 9,9-(1-chloromethylethyl-enedioxy)-15-hydroxyprostanoate |
| 272D | 112A | 2,3-Butane-diol | dl-methyl 9,9-(1,2-dimethylethylene-dioxyl)-15-hydroxyprostanoate |
| 272E | 112A | 1,3-Pro-panediol | dl-methyl 15-hydroxy-9,9-(propylene-dioxy)prostanoate |
| 272F | 112B | Ethylene-glycol | dl-methyl 9,9-(ethylenedioxy)-15-epi-hydroxyprostanoate |
| 272G | 112B | 1,2-Pro-panediol | dl-methyl 15-epi-hydroxy-9,9-(1-methyl-ethylenedioxy)prostanoate |
| 272H | 112B | 1-Chloro-2,3-pro-panediol | dl-methyl 9,9-(1-chloromethylethylene-dioxy)-15-epi-hydroxyprostanoate |
| 272I | 112B | 2,3-Butane-diol | dl-methyl 9,9-(1,2-dimethylethylene-dioxy)-15-epi-hydroxyprostanoate |
| 272J | 112B | 1,3-Propane-diol | dl-methyl 15-epi-hydroxy-9,9-(propylene-dioxy)prostanoate |

EXAMPLES 273–291

Treatment of the various 15-hydroxy-prostanate ketals of Table 8 below chromium trioxide in the manner of Example 56 above is productive of the corresponding 15-oxo-prostanoate ketals of the Table.

TABLE 8

| Example | Starting 15-hydroxyprostanoate ketals of example | Product 15-oxo-prostanoate ketals |
|---|---|---|
| 273 | 113 | Ethyl 9,9-(ethylene-dioxy)-15-oxo-19,20-dinor-prostanoate |
| 274 | 114 | Ethyl 9,9-(ethylene-dioxy)-15-oxo-5,6,7,19,20-pentanor-prostanoate |
| 275 | 115 | Ethyl 9,9-(ethylene-dioxy)-15-oxo-6,7,-19,20-tetranor-prostanoate |
| 276 | 145 | Ethyl 9,9-(1-methyl ethylenedioxy)-15-oxo-7a,7b-bishomo-19,20-dinor-prostanoate |
| 277 | 146 | Ethyl 9,9-(1-methyl-ethylenedioxy)-15-oxo-7,19,20-tri-nor-prostanoate |
| 278 | 147 | Ethyl 9,9-(1-methyl-ethylenedioxy)-15-oxo-7a-homo-19,20-dinor-prostanoate |
| 279 | 152 | Butyl 9,9-(1,2-di-methylethylenedi-oxy)-15-oxo-19,20-dinor-prostanoate |
| 280 | 180 | Isopropyl 15-oxo-9,9-(propylenedi-oxy)-19,20-dinor-prostanoate |
| 281 | 181 | Methyl 15-oxo-9,9- |

TABLE 8-continued

| Example | Starting 15-hy-droxyprostanoate ketals of example | Product 15-oxo-prostanoate ketals |
|---|---|---|
| 282 | 182 | Decyl 15-oxo-9,9-(propylenedioxy)-19,20-dinor-prostanoate |
| 283 | 205 | Ethyl 9,9-(2,2-dimethylpropylenedioxy)-15-oxo-5,6,7-trinor-prostanoate |
| 284 | 206 | Ethyl 9,9-(2,2-dimethylpropylenedioxy)-15-oxo-6,7-dinor-prostanoate |
| 285 | 227 | Ethyl 9,9-(ethylenedithia)-15-oxo-7a,7b-bishomo prostanoate |
| 286 | 228 | Ethyl 9,9-(ethylenedithia)-15-oxo-7-nor-prostanoate |
| 287 | 258 | Ethyl 9,9-(ethyleneoxythia)-15-oxo-7a-homo-prostanoate |
| 288 | 259 | Butyl 9,9-(ethyleneoxythia)-15-oxo-prostanoate |
| 289 | 260 | Isopropyl 9,9-(ethyleneoxythia)-15-oxo-prostanoate |
| 290 | 261 | Methyl 9,9-(ethyleneoxythia)-15-oxo-prostanoate |
| 291 | 262 | Decyl 9,9-(ethyleneoxythia)-15-oxo-prostanoate |

EXAMPLES 292–310

Treatment of the various 15-oxo-prostanoate ketals of Table 9 below with methyl magnesium indole in the manner of Example 57 is productive of the corresponding 15-hydroxy-15-methyl-prostanoate ketals of the Table.

TABLE 9

| Example | Starting 15-oxo-prostanoate ketals of Example | Product 15-hydroxy-15-methyl-prostanoate ketals |
|---|---|---|
| 292 | 273 | Ethyl 9,9-(ethylenedioxy)-15-hydroxy-15-methyl-19,20-dinor-prostanoate |
| 293 | 274 | Ethyl 9,9-(ethylenedioxy)-15-hydroxy-15-methyl-5,6,7,19,20-pentanor-prostanoate |
| 294 | 275 | Ethyl 9,9-(ethylenedioxy)-15-hydroxy-15-methyl-6,7,19,20-tetranor-prostanoate |
| 295 | 276 | Ethyl 15-hydroxy-15-methyl-9,9-(1-methylethylenedioxy)-7a,7b-bishomo-19,20-dinor-prostanoate |
| 296 | 277 | Ethyl 15-hydroxy-15-methyl-9,9-(1-methylethylenedioxy)-7,19,20-trinor-prostanoate |
| 297 | 278 | Ethyl 15-hydroxy-15-methyl-9,9-(1-methylethylenedioxy)-7a-homo-19,20-dinor-prostanoate |
| 298 | 279 | Butyl 9,9-(1,2-dimethylethylenedioxy)-15-hydroxy-15-methyl-19,20-dinor-prostanoate |
| 299 | 280 | Isopropyl 15-hydroxy-15-methyl-9,9-(propylenedioxy)-19,20-dinor-prostanoate |
| 300 | 281 | Methyl 15-hydroxy-15-methyl-9,9-(propylenedioxy)-19,20-dinor-prostanoate |
| 301 | 282 | Decyl 15-hydroxy-15-methyl-9,9-(propylenedioxy)-19,20-dinor-prostanoate |
| 302 | 283 | Ethyl 9,9-(2,2-dimethylpropylenedioxy)-15-hydroxy-15-methyl-5,6,7-trinor-prostanoate |
| 303 | 284 | Ethyl 9,9-(2,2-dimethylpropylenedioxy)-15-hydroxy-15-methyl-6,7-dinor-prostanoate |
| 304 | 285 | Ethyl 9,9-(ethylenedithia)-15-hydroxy-15-methyl-7a,7b-bishomo-prostanoate |
| 305 | 286 | Ethyl 9,9-(ethylenedithia)-15-hydroxy-15-methyl-7-nor-prostanoate |
| 306 | 287 | Ethyl 9,9-(ethyleneoxythia)-15-hydroxy-15-methyl-7a-homo-prostanoate |
| 307 | 288 | Butyl 9,9-(ethyleneoxythia)-15-hydroxy-15-methyl-prostanoate |
| 308 | 289 | Isopropyl 9,9-(ethyleneoxythia)-15-hydroxy-15-methyl-prostanoate |
| 309 | 290 | Methyl 9,9-(ethyleneoxythia)-15-hydroxy-15-methyl-prostanoate |
| 310 | 291 | Decyl 9,9-(ethyleneoxythia)-15-hydroxy-15-methyl-prostanoate |

EXAMPLES 311–430

Saponification of the various prostanoate ketals of Table 10 below in the manner of Example 58 above is productive of the prostanoic acid ketals of the Table.

TABLE 10

| Example | Starting prostanoate ketals of example | Product Prostanoic acid ketals |
|---|---|---|
| 311 | 113 | 9,9-(ethylenedioxy)-15-hydroxy-19,20-dinor-prostanoic acid |
| 312 | 114 | 9,9-(ethylenedioxy)-15-hydroxy-5,6,7,19,20-pentanor-prostanoic acid |
| 313 | 115 | 9,9-(ethylenedioxy)-15-hydroxy-6,7,19,20-tetranor-prostanoic acid |
| 314 | 116 | 9,9-(ethylenedioxy)-15-hydroxy-7a,7b-bis- |

TABLE 10-continued

| Example | Starting prostanoate ketals of example | Product Prostanoic acid ketals |
|---|---|---|
| 315 | 117 | 9,9-(ethylenedioxy)-15-hydroxy-7,19,20-trinor-prostanoic acid |
| 316 | 118 | 9,9-(ethylenedioxy)-15-hydroxy-7a-homo-19,20-dinor-prostanoic acid |
| 317 | 123 | 9,9-(ethylenedioxy)-15-hydroxy-5,6,7-trinor-prostanoic acid |
| 318 | 124 | 9,9-(ethylenedioxy)-15-hydroxy-6,7-dinor-prostanoic acid |
| 319 | 125 | 9,9-(ethylenedioxy)-15-hydroxy-7a,7b-bis-homo-prostanoic acid |
| 320 | 126 | 9,9-(ethylenedioxy)-15-hydroxy-7-nor-prostanoic acid |
| 321 | 127 | 9,9-(ethylenedioxy)-15-hydroxy-7a-homo-prostanoic acid |
| 322 | 132 | 9,9-(ethylenedioxy)-15-hydroxy-prostanoic acid |
| 323 | 133 | l-9,9-(ethylenedioxy)-15(R)-hydroxy-prostanoic acid |
| 324 | 134 | l-9,9-(ethylenedioxy)-15(S)-hydroxy-prostanoic acid |
| 325 | 135 | l-9,9-(ethylenedioxy)-15(S)-hydroxy-16(R)-methyl-prostanoic acid |
| 326 | 136 | l-9,9-(ethylenedioxy)-15(S)-hydroxy-16(S)-methyl-prostanoic acid |
| 327 | 137 | l-9,9-(ethylenedioxy)-15(R)-hydroxy-16(S)-methyl-prostanoic acid |
| 328 | 138 | l-9,9-(ethylenedioxy)-15(R)-hydroxy-16(R)-methyl-prostanoic acid |
| 329 | 139 | l-9,9-(ethylenedioxy)-15(S)-hydroxy-16,16-dimethyl-prostanoic acid |
| 330 | 140 | l-20-ethyl-9,9-(ethylenedioxy)-15(S)-hydroxy-prostanoic acid |
| 331 | 141 | ent-9,9-(ethylenedioxy)-15-hydroxy-prostanoic acid |
| 332 | 142 | 15-hydroxy-9,9-(1-methylethylenedioxy)-19,20-dinor-prostanoic acid |
| 333 | 143 | 15-hydroxy-9,9-(1-methylethylenedioxy)-5,6,7,19,20-pentanor-prostanoic acid |
| 334 | 144 | 15-hydroxy-9,9-(1-methylethylenedioxy)-6,7-19,20-tetranor-prostanoic acid |
| 335 | 145 | 15-hydroxy-9,9-(1-methylethylenedioxy)-7a,7b-bishomo-19,20-dinor-prostanoic acid |
| 336 | 146 | 15-hydroxy-9,9-(1-methylethylenedioxy)-7,19,20-trinor-prostanoic acid |
| 337 | 147 | 15-hydroxy-9,9-(1-methylethylenedioxy)-7a-homo-19,20-dinor-prostanoic acid |
| 338 | 148 | l-15(S)-hydroxy-9,9-(1-methylethylenedioxy)-prostanoic acid |
| 339 | 149 | l-15(S)-hydroxy-16(R)-methyl-9,9-(1-methylethylenedioxy)-prostanoic acid |
| 340 | 150 | l-15(S)-hydroxy-16(S)-methyl-9,9-(1-methylethylenedioxy)-prostanoic acid |
| 341 | 151 | l-15(S)-hydroxy-16,16-dimethyl-9,9-(1-methylethylenedioxy)-prostanoic acid |
| 342 | 152 | 9,9-(1,2-dimethylethylenedioxy)-15-hydroxy-19,20-dinor-prostanoic acid |
| 343 | 156 | 9,9-(1,2-dimethylethylenedioxy)-15-hydroxy-5,6,7-trinor-prostanoic acid |
| 344 | 157 | 9,9-(1,2-dimethylethylenedioxy)-15-hydroxy-6,7-dinor-prostanoic acid |
| 345 | 158 | l-9,9-(1,2-dimethylethylenedioxy)-15(S)-hydroxy-prostanoic acid |
| 346 | 159 | l-9,9-(1,2-dimethylethylenedioxy)-15(S)-hydroxy-16(R)-methyl-prostanoic acid |
| 347 | 160 | l-9,9-(1,2-dimethylethylenedioxy)-15(S)-hydroxy-16(S)-methyl-prostanoic acid |
| 348 | 161 | l-9,9-(1,2-dimethylethylenedioxy)-15(S)-hydroxy-16,16-dimethyl-prostanoic acid |
| 349 | 162 | 9,9-(1-chloromethylethylenedioxy)-15-hydroxy-7a,7b-bis-homo-prostanoic acid |
| 350 | 163 | 9,9-(1-chloromethylethylenedioxy)-15-hydroxy-7-nor-prostanoic acid |
| 351 | 164 | 9,9-(1-chloromethylethylenedioxy)-15-hydroxy-7a-homo-prostanoic acid |
| 352 | 165 | 9,9-(1-chloromethylethylenedioxy)-15-hydroxy-prostanoic acid |
| 353 | 169 | l-9,9-(1-chloromethylethylenedioxy)-15(S)-hydroxy-prostanoic acid |
| 354 | 170 | l-9,9-(1-chloromethylethylenedioxy)-15(S)-hydroxy-16(R)-methyl-prostanoic acid |
| 355 | 171 | l-9,9-(1-chloromethylethylenedioxy)-15(S)-hydroxy-16(S)-methyl-prostanoic acid |
| 356 | 172 | l-9,9-(1-chloromethylethylenedioxy)-15(S)-hydroxy-16,16-dimethyl-prostanoic acid |
| 357 | 173 | 15-hydroxy-9,9-(propylenedioxy)-19,20-dinor-prostanoic acid |
| 358 | 174 | 15-hydroxy-9,9-(propylenedioxy)-5,6,7,19,20-pentanor-prostanoic acid |
| 359 | 175 | 15-hydroxy-9,9-(propylenedioxy)-6,7,19,20-tetranor-prostanoate |
| 360 | 176 | 15-hydroxy-9,9-(propylenedioxy)-7a,7b-bishomo-19,20-dinor-prostanoic acid |
| 361 | 177 | 15-hydroxy-9,9-(propylenedioxy)-7,19,20-trinor-prostanoic acid |
| 362 | 178 | 15-hydroxy-9,9-(propylenedioxy)-7a-homo-19,20-dinor-prostanoic acid |
| 363 | 183 | 15-hydroxy-9,9-(propylenedioxy)-5,6,7- |

TABLE 10-continued

| Example | Starting prostanoate ketals of example | Product Prostanoic acid ketals |
|---|---|---|
| 364 | 184 | trinor-prostanoic acid 15-hydroxy-9,9-(propylenedioxy)-6,7-dinor-prostanoic acid |
| 365 | 185 | 15-hydroxy-9,9-(propylenedioxy)-7a,7b-bishomo-prostanoic acid |
| 366 | 186 | 15-hydroxy-9,9-(propylenedioxy)-7-nor-prostanoic acid |
| 367 | 187 | 15-hydroxy-9,9-(propylenedioxy)-7a-homo-prostanoic acid |
| 368 | 188 | 15-hydroxy-9,9-(propylenedioxy)-prostanoic acid |
| 369 | 193 | l-15(R)-hydroxy-9,9-(propylenedioxy)-prostanoic acid |
| 370 | 194 | l-15(S)-hydroxy-9,9-(propylenedioxy)-prostanoic acid |
| 371 | 195 | l-15(S)-hydroxy-16(R)-methyl-9,9-(propylenedioxy)-prostanoic acid |
| 372 | 196 | l-15(S)-hydroxy-16(S)-methyl-9,9-(propylenedioxy)-prostanoic acid |
| 373 | 197 | l-15(R)-hydroxy-16(S)-methyl-9,9-(propylenedioxy)-prostanoic acid |
| 374 | 198 | l-15(R)-hydroxy-16(R)-methyl-9,9-(propylenedioxy)-prostanoic acid |
| 375 | 199 | l-15(S)-hydroxy-16,16-dimethyl-9,9-(propylenedioxy)-prostanoic acid |
| 376 | 200 | l-20-ethyl-15(S)-hydroxy-9,9-(propylenedioxy)-prostanoic acid |
| 377 | 201 | ent-15-hydroxy-9,9-(propylenedioxy)-prostanoic acid |
| 378 | 202 | 9,9-(2,2-dimethylpropylenedioxy)-15-hydroxy-19,20-dinor-prostanoic acid |
| 379 | 203 | 9,9-(2,2-dimethylpropylenedioxy)-15-hydroxy-6,7,19,20-tetranor-prostanoic acid |
| 380 | 205 | 9,9-(2,2-dimethylpropylenedioxy)-15-hydroxy-5,6,7-trinor-prostanoic acid |
| 381 | 206 | 9,9-(2,2-dimethylpropylenedioxy)-15-hydroxy-6,7-dinor-prostanoic acid |
| 382 | 207 | 9,9-(2,2-dimethylpropylenedioxy)-15-hydroxy-7a,7b-bishomo-prostanoic acid |
| 383 | 208 | 9,9-(2,2-dimethylpropylenedioxy)-15-hydroxy-7-nor-prostanoic acid |
| 384 | 209 | 9,9-(2,2-dimethylpropylenedioxy)-15-hydroxy-7a-homo-prostanoic acid |
| 385 | 210 | 9,9-(2,2-dimethylpropylenedioxy)-15-hydroxy-prostanoic acid |
| 386 | 212 | 9,9-(2,2-dimethylpropylenedioxy)-15(S)-hydroxy-prostanoic acid |
| 387 | 213 | l-9,9-(2,2-dimethylpropylenedioxy)-15(S)-hydroxy-16(R)-methyl-prostanoic acid |
| 388 | 214 | l-9,9-(2,2-dimethylpropylenedioxy)-15(S)-hydroxy-16,16-dimethyl-prostanoic acid |
| 389 | 215 | 9,9-(ethylenedithia)-15-hydroxy-19,20-dinor prostanoic acid |
| 390 | 216 | 9,9-(ethylenedithia)-15-hydroxy-5,6,7,19,20-pentanor-prostanoic acid |
| 391 | 217 | 9,9-(ethylenedithia)-15-hydroxy-6,7,19,20-tetranor-prostanoic acid |
| 392 | 218 | 9,9-(ethylenedithia)-15-hydroxy-7a,7b-bishomo-19,20-dinor-prostanoic acid |
| 393 | 219 | 9,9-(ethylenedithia)-15-hydroxy-7,19,20-trinor-prostanoic acid |
| 394 | 220 | 9,9-(ethylenedithia)-15-hydroxy-7a-homo-19,20-dinor-prostanoic acid |
| 395 | 225 | 9,9-(ethylenedithia)-15-hydroxy-5,6,7-trinor-prostanoic acid |
| 396 | 226 | 9,9-(ethylenedithia)-15-hydroxy-6,7-dinor-prostanoic acid |
| 397 | 227 | 9,9-(ethylenedithia)-15-hydroxy-7a,7b-bishomo-prostanoic acid |
| 398 | 228 | 9,9-(ethylenedithia)-15-hydroxy-7-nor-prostanoic acid |
| 399 | 229 | 9,9-(ethylenedithia)-15-hydroxy-7a-homo-prostanoic acid |
| 400 | 230 | 9,9-(ethylenedithia)-15-hydroxy-prostanoic acid |
| 401 | 235 | l-9,9-(ethylenedithia)-15(R)-hydroxy-prostanoic acid |
| 402 | 236 | l-9,9-(ethylenedithia)-15(S)-hydroxy-prostanoic acid |
| 403 | 237 | l-9,9-(ethylenedithia)-15(S)-hydroxy-16(R)-methyl-prostanoic acid |
| 404 | 238 | l-9,9-(ethylenedithia)-15(S)-hydroxy-16(S)-methyl-prostanoic acid |
| 405 | 239 | l-9,9-(ethylenedithia)-15(R)-hydroxy-16(S)-methylprostanoic acid |
| 406 | 240 | l-9,9-(ethylenedithia)-15(R)-hydroxy-16(R)-methylprostanoic acid |
| 407 | 241 | l-9,9-(ethylenedithia)-15(S)-hydroxy-16,16-dimethylprostanoic acid |
| 408 | 242 | l-20-ethyl-9,9-(ethylenedithia)-15(S)-hydroxy-prostanoic acid |
| 409 | 243 | ent-9,9-(ethylenedithia)-15-hydroxy-prostanoic acid |
| 410 | 244 | 9,9-(ethyleneoxythia)-15-hydroxy-19,20-dinor-prostanoic acid |
| 411 | 245 | 9,9-(ethyleneoxythia)-15-hydroxy-5,6,7,19,20-pentanor-prostanoic acid |
| 412 | 246 | 9,9-(ethyleneoxythia)-15-hydroxy-6,7,19,20-tetranor-prostanoic acid |
| 413 | 247 | 9,9-(ethyleneoxythia)-15-hydroxy-7a,7b-bishomo-19,20-dinor-prostanoic acid |
| 414 | 248 | 9,9-(ethyleneoxythia)-15-hydroxy-7,19,20-trinor-prostanoic acid |

TABLE 10-continued

| Example | Starting prostanoate ketals of example | Product Prostanoic acid ketals |
|---|---|---|
| 415 | 249 | 9,9-(ethyleneoxythia)-15-hydroxy-7a-homo-19,20-dinor-prostanoic acid |
| 416 | 254 | 9,9-(ethyleneoxythia)-15-hydroxy-5,6,7-trinor-prostanoic acid |
| 417 | 255 | 9,9-(ethyleneoxythia)-15-hydroxy-6,7-dinor-prostanoic acid |
| 418 | 256 | 9,9-(ethyleneoxythia)-15-hydroxy-7a,7b-bis-homo-prostanoic acid |
| 419 | 257 | 9,9-(ethyleneoxythia)-15-hydroxy-7-nor-prostanoic acid |
| 420 | 258 | 9,9-(ethyleneoxythia)-15-hydroxy-7a-homo-prostanoic acid |
| 421 | 259 | 9,9-(ethyleneoxythia)-15-hydroxy-prostanoic acid |
| 422 | 264 | l-9,9-(ethyleneoxythia)-15(R)-hydroxy-prostanoic acid |
| 423 | 265 | l-9,9-(ethyleneoxythia)-15(S)-hydroxy-prostanoic acid |
| 424 | 266 | l-9,9-(ethyleneoxythia)-15(S)-hydroxy-16-(R)-methyl-prostanoic acid |
| 425 | 267 | l-9,9-(ethyleneoxythia)-15(S)-hydroxy-16(S)-methyl-prostanoic acid |
| 426 | 268 | l-9,9-(ethyleneoxythia)-15(R)-hydroxy-16(S)-methyl-prostanoic acid |
| 427 | 269 | l-9,9-(ethyleneoxythia)-15(R)-hydroxy-16(R)-methyl-prostanoic acid |
| 428 | 270 | l-9,9-(ethyleneoxythia)-15(S)-hydroxy-16,16-dimethyl-prostanoic acid |
| 429 | 271 | l-20-ethyl-9,9-(ethyleneoxythia)-15(S)-hydroxy-prostanoic acid |
| 430 | 272 | ent-9,9-(ethyleneoxythia)-15-hydroxy-prostanoic acid |
| 430A | 272A | dl-9,9-(ethylenedioxy)-15-hydroxyprostanoic acid |
| 430B | 272B | dl-15-hydroxy-9,9-(1-methylethylenedioxy)-prostanoic acid |
| 430C | 272C | dl-9,9-(1-chloromethylethylenedioxy)-15-hydroxyprostanoic acid |
| 430D | 272D | dl-9,9-(1,2-dimethylethylenedioxy)-15-hydroxyprostanoic acid |
| 430E | 272E | dl-15-hydroxy-9,9-(propylenedioxy)prostanoic acid |
| 430F | 272F | dl-9,9-(ethylenedioxy)-15-epi-hydroxyprostanoic acid |
| 430G | 272G | dl-15-epi-hydroxy-9,9-(1-methylenedioxy)prostanoic acid |
| 430H | 272H | dl-9,9-(1-chloromethylethylenedioxy)-15-epi-hydroxyprostanoic acid |
| 430I | 272I | dl-9,9-(1,2-dimethylethylenedioxy)-15-epi-hydroxyprostanoic acid |
| 430J | 272J | dl-15-epi-hydroxy-9,9-(propylenedioxy)-prostanoic acid |

EXAMPLES 431 – 449

Saponification of the various 15-hydroxy-15-methyl-prostanoate ketals of Table 11 below in the manner of Example 58 above is productive of the corresponding prostanoic acid ketals of the Table.

TABLE 11

| Example | Starting 15-hydroxy-15-methyl-prostanoate ketals | Product 15-Hydroxy-15-methyl-prostanoic acid ketals |
|---|---|---|
| 431 | 292 | 9,9-(ethylenedioxy)-15-hydroxy-15-methyl-19,20-dinor-prostanoic acid |
| 432 | 293 | 9,9-(ethylenedioxy)-15-hydroxy-15-methyl-5,6,7,19,20-pentanor-prostanoic acid |
| 433 | 294 | 9,9-(ethylenedioxy)-15-hydroxy-15-methyl-6,7,19,20-tetranor-prostanoic acid |
| 434 | 295 | 15-hydroxy-15-methyl-9,9-(1-methylethylenedioxy)-7a,7b-bishomo-19,20-dinor-prostanoic acid |
| 435 | 296 | 15-hydroxy-15-methyl-9,9-(1-methylethylenedioxy)-7,19,20-trinor-prostanoic acid |
| 436 | 297 | 15-hydroxy-15-methyl-9,9-(1-methylethylenedioxy)-7a-homo-19,20-dinor-prostanoic acid |
| 437 | 298 | 9,9-(1,2-dimethylethylenedioxy)-15-hydroxy-15-methyl-19,20-dinor-prostanoic acid |
| 438 | 299 | 15-hydroxy-15-methyl-9,9-(propylenedioxy)-19,20-dinor-prostanoic acid |
| 439 | 300 | 15-hydroxy-15-methyl-9,9-(propylenedioxy)-19,20-dinor-prostanoic acid |
| 440 | 301 | 15-hydroxy-15-methyl-9,9-(propylenedioxy)-19,20-dinor-prostanoic acid |
| 441 | 302 | 9,9-(2,2-dimethylpropylenedioxy)-15-hydroxy-15-methyl-5,6,7-trinor-prostanoic acid |
| 442 | 303 | 9,9-(2,2-dimethylpropylenedioxy)-15-hydroxy-15-methyl-6,7-dinor-prostanoic acid |
| 443 | 304 | 9,9-(ethylenedithia)-15-hydroxy-15-methyl-7a,7b-bishomo-prostanoic acid |
| 444 | 305 | 9,9-(ethylenedithia)-15-hydroxy-15-methyl-7-nor-prostanoic acid |
| 445 | 306 | 9,9-(ethylenedithia)-15-hydroxy-15-methyl-7a-homo-prostanoic acid |
| 446 | 307 | 9,9-(ethyleneoxythia)-15-hydroxy-15-methyl-prostanoic acid |
| 447 | 308 | 9,9-(ethyleneoxythia)-15-hydroxy-prostanoic acid |
| 448 | 309 | 9,9-(ethyleneoxythia)-15-hydroxy-15-methyl-prostanoic acid |
| 449 | 310 | 9,9-(ethyleneoxythia)-15-hydroxy-15-methyl-prostanoic acid |

EXAMPLE 450

Preparation of
1-15(S)-acetoxy-9,9-(ethylenedioxy)prostanoic acid

A solution of 1 g. of 1-9,9-(ethylenedioxy)-15(S)-hydroxy prostanoic acid (Example 324) in 10 ml. of reagent pyridine is treated with 1 ml. of acetic anhydride at ambient temperature for 15 hours. Dilution with water, followed by extraction with chloroform and evaporation to dryness of the chloroform extracts gives an oily material. Treatment of this oil with aqueous methanol at ambient temperature for 18 hours, followed by evaporation affords 950 mg. of product as an oil.

EXAMPLES 451 – 571

Treatment of the various 15-hydroxy-prostanoic acid ketals listed in Table 12 below with the indicated reagent, by the method described in Example 450 above is productive of the esters of the Table.

TABLE 12

| Example | Starting 15-ol of Example | Acylating reagent | Product |
|---|---|---|---|
| 451 | 311 | Acetic anhydride | 15-acetoxy-9,9-(ethylenedioxy)-19,20-dinor-prostanoic acid |
| 452 | 313 | Acetic anhydride | 15-acetoxy-9,9-(ethylenedioxy)-6,7,19,20-tetranor-prostanoic acid |
| 453 | 314 | Acetic anhydride | 15-acetoxy-9,9-(ethylenedioxy)-7a,7b-bishomo-19,20-dinor-prostanoic acid |
| 454 | 316 | Acetic anhydride | 15-acetoxy-9,9-(ethylenedioxy)-19,20-dinor-prostanoic acid |
| 455 | 319 | Acetic anhydride | 15-acetoxy-9,9-(ethylenedioxy)-7a,7b-bishomo-prostanoic acid |
| 456 | 320 | Acetic anhydride | 15-acetoxy-9,9-(ethylenedioxy)-7-nor-prostanoic acid |
| 457 | 321 | Acetic anhydride | 15-acetoxy-9,9-(ethylenedioxy)-7a-homo-prostanoic acid |
| 458 | 325 | Acetic anhydride | 1-15(S)-acetoxy-9,9-(ethylenedioxy)-16(R)-methyl prostanoic acid |
| 459 | 329 | Acetic anhydride | 1-15(S)-acetoxy-9,9-(ethylenedioxy)-16,16-dimethylprostanoic acid |
| 460 | 332 | Acetic anhydride | 15-acetoxy-9,9-(1-methylethylenedioxy)-19,20-dinor-prostanoic acid |
| 461 | 343 | Acetic anhydride | 15-acetoxy-9,9-(1,2-dimethylethylenedioxy)-5,6,7-trinor-prostanoic acid |
| 462 | 350 | Acetic anhydride | 15-acetoxy-9,9-(1-chloromethylethylenedioxy)-7-nor-prostanoic acid |
| 463 | 353 | Acetic anhydride | 1-15(S)-acetoxy-9,9-(1-chloromethylenedioxy)-prostanoic acid |
| 464 | 356 | Acetic anhydride | 1-15(S)-acetoxy-(1-chloromethylenedioxy)-16,16-dimethylprostanoic acid |
| 465 | 361 | Acetic anhydride | 15-acetoxy-9,9-(propylenedioxy)-7,19,20-trinor-prostanoic acid |
| 466 | 365 | Acetic anhydride | 15-acetoxy-9,9-(propylenedioxy)-7a,7b-bishomo-prostanoic acid |
| 467 | 370 | Acetic anhydride | 1-15(S)-acetoxy-9,9-(propylenedioxy)-prostanoic acid |
| 468 | 375 | Acetic anhydride | 1-15(S)-acetoxy-16,16-dimethyl-9,9-(propylenedioxy)prostanoic acid |
| 469 | 381 | Acetic anhydride | 15-acetoxy-9,9-(2,2-dimethylpropylenedioxy)-6,7-dinor-prostanoic acid |
| 470 | 391 | Acetic anhydride | 15-acetoxy-9,9-(ethylenedithia)-6,7,19,20-tetranor-prostanoic acid |
| 471 | 416 | Acetic anhydride | 15-acetoxy-9,9-(ethyleneoxythia)-5,6,7-trinor-prostanoic acid |
| 472 | 402 | Acetic anhydride | 1-15(S)-acetoxy-9,9-(ethylenedithia)-prostanoic acid |
| 473 | 403 | Acetic anhydride | 1-15(S)-acetoxy-9,9-(ethylenedithia)-16(R)-methyl-prostanoic acid |
| 474 | 407 | Acetic anhydride | 1-15(S)-acetoxy-9,9-(ethylenedithia)-16,16-dimethyl-prostanoic acid |
| 475 | 423 | Acetic anhydride | 1-15(S)-acetoxy-9,9-(ethyleneoxythia)-prostanoic acid |
| 476 | 424 | Acetic anhydride | 1-15(S)-acetoxy-9,9-(ethyleneoxythia)-16(R)-methyl-prostanoic acid |
| 477 | 428 | Acetic anhydride | 1-15(S)-acetoxy-9,9-(ethyleneoxythia)-16,16-dimethylprostanoic acid |
| 478 | 313 | Propionic anhydride | 9,9-(ethylenedioxy)-15-propionyloxy-6,7,19,20-tetranor-prostanoic acid |
| 479 | 325 | Propionic anhydride | 1-9,9-(ethylenedioxy)-16(R)-methyl-15(S)-propionyloxy-prostanoic acid |
| 480 | 333 | Propionic anhydride | 9,9-(1-methylethylenedioxy)-15-propionyloxy-5,6,7,19,20-pentanor-prostanoic acid |
| 481 | 344 | Propionic anhydride | 9,9-(1,2-dimethylethylenedioxy)-15-propionyloxy-6,7-dinor-prostanoic acid |
| 482 | 349 | Propionic anhydride | 9,9-(1-chloromethylethylenedioxy)-15-propionyloxy-7a,7b-bishomo-prostanoic acid |
| 483 | 353 | Propionic anhydride | 1-9,9-(1-chloromethylethylenedioxy)-15(S)-propionyloxy-prostanoic acid |
| 484 | 356 | Propionic anhydride | 1-(1-chloromethylenedioxy)-16,16-dimethyl-15(S)-propionyloxy- |

TABLE 12-continued

| Example | Starting 15-ol of Example | Acylating reagent | Product |
|---|---|---|---|
| | | | prostanoic acid |
| 485 | 361 | Propionic anhydride | 15-propionyloxy-9,9-(propylenedioxy)-7,19,20-trinor-prostanoic acid |
| 486 | 362 | Propionic anhydride | 15-propionyloxy-9,9-(propylenedioxy)-7a-homo-19,20-dinor-prostanoic acid |
| 487 | 363 | Propionic anhydride | 15-propionyloxy-9,9-(propylenedioxy)-5,6,7-trinor-prostanoic acid |
| 488 | 370 | Propionic anhydride | l-15(S)-propionyloxy-9,9-(propylenedioxy)-prostanoic acid |
| 489 | 375 | Propionic anhydride | l-16,16-dimethyl-15(S)-propionyloxy-9,9-(propylenedioxy)prostanoic acid |
| 490 | 381 | Propionic anhydride | 9,9-(2,2-dimethylpropylenedioxy)-15-propionyloxy-6,7-dinor-prostanoic acid |
| 491 | 397 | Propionic anhydride | 9,9-(ethylenedithia)-15-propionyloxy-7a,7b-bishomo-prostanoic acid |
| 492 | 402 | Propionic anhydride | l-9,9-(ethylenedithia)-15(S)-propionyloxy-prostanoic acid |
| 493 | 403 | Propionic anhydride | l-9,9-(ethylenedithia)-16(R)-methyl-15(S)-propionyloxy-prostanoic acid |
| 494 | 407 | Propionic anhydride | l-9,9-(ethylenedithia)-16,16-dimethyl-15(S)-propionyloxy-prostanoic acid |
| 495 | 419 | Propionic anhydride | 9,9-(ethyleneoxythia)-15-propionyloxy-7-nor-prostanoic acid |
| 496 | 420 | Propionic anhydride | 9,9-(ethyleneoxythia)-15-propionyloxy-7a-homo-prostanoic acid |
| 497 | 423 | Propionic anhydride | l-9,9-(ethyleneoxythia)-15(S)-propionyloxy-prostanoic acid |
| 498 | 424 | Propionic anhydride | l-9,9-(ethyleneoxythia)-16(R)-methyl-15(S)-propionyloxy-prostanoic acid |
| 499 | 428 | Propionic anhydride | l-9,9-(ethyleneoxythia)-16,16-dimethyl-15(S)-propionyloxy-prostanoic acid |
| 500 | 311 | Butyric anhydride | 15-butyryloxy-9,9-(ethylenedioxy)-19,20-dinor-prostanoic acid |
| 501 | 325 | Butyric anhydride | l-15(S)-butyryloxy-9,9-(ethylenedioxy-16(R)-methyl prostanoic acid |
| 502 | 329 | Butyric anhydride | l-15(S)-butyryloxy-9,9-(ethylenedioxy)-16,16-dimethylprostanoic acid |
| 503 | 334 | Butyric anhydride | 15-butyryloxy-9,9-(1-methylethylenedioxy)-6,7,19,20-tetranor-prostanoic acid |
| 504 | 342 | Butyric anhydride | 15-butyryloxy-9,9-(1,2-dimethylethylenedioxy)-19,20-dinor-prostanoic acid |
| 505 | 353 | Butyric anhydride | l-15(S)-butyryloxy-9,9-(1-chloromethylethylenedioxy)-prostanoic acid |
| 506 | 356 | Butyric anhydride | l-15(S)-butyryloxy-(1-chloromethylethylenedioxy)-16,16-dimethylprostanoic acid |
| 507 | 364 | Butyric anhydride | 15-butyryloxy-9,9-(propylenedioxy)-6,7-dinor-prostanoic acid |
| 508 | 370 | Butyric anhydride | l-15(S)-butyryloxy-9,9-(propylenedioxy)-prostanoic acid |
| 509 | 375 | Butyric anhydride | l-15(S)-butyryloxy-16,16-dimethyl-9,9-(propylenedioxy)-prostanoic acid |
| 510 | 382 | Butyric anhydride | 15-butyryloxy-9,9-(2,2-dimethylpropylenedioxy)-7a,7b-bishomo-prostanoic acid |
| 511 | 394 | Butyric anhydride | 15-butyryloxy-9,9-(ethylenedithia)-7a-homo-19,20-dinor-prostanoic acid |
| 512 | 402 | Butyric anhydride | l-15(S)-butyryloxy-9,9-(ethylenedithia)-prostanoic acid |
| 513 | 403 | Butyric anhydride | l-15(S)-butyryloxy-9,9-(ethylenedithia)-16(R)-methyl-prostanoic acid |
| 514 | 407 | Butyric anhydride | l-15(S)-butyryloxy-9,9-(ethylenedithia)-16,16-dimethyl-prostanoic acid |
| 515 | 419 | Butyric anhydride | 15-butyryloxy-9,9-(ethyleneoxythia)-7-nor-prostanoic acid |
| 516 | 423 | Butyric anhydride | l-15(S)-butyryloxy-9,9-(ethyleneoxythia)-prostanoic acid |
| 517 | 424 | Butyric anhydride | l-15(S)-butyryloxy-9,9-(ethyleneoxythia)-16(R)-methyl-prostanoic acid |
| 518 | 428 | Butyric anhydride | l-15(S)-butyryloxy-9,9-(ethyleneoxythia)-16,16-dimethyl-prostanoic acid |
| 519 | 315 | Valeric anhydride | 9,9-(ethylenedioxy)-15-valeryloxy-7,19,20-trinor-prostanoic acid |
| 520 | 325 | Valeric anhydride | l-9,9-(ethylenedioxy)-16(R)-methyl-15(S)-valeryloxy-prostanoic acid |
| 521 | 329 | Valeric anhy- | l-9,9-(ethylenedioxy)-16,16-di- |

TABLE 12-continued

| Example | Starting 15-ol of Example | Acylating reagent | Product |
|---|---|---|---|
| | | dride | methyl-15(S)-valeryloxy-prostanoic acid |
| 522 | 351 | Valeric anhydride | 9,9-(1-chloromethylethylenedioxy)-15-valeryloxy-7a-homo-prostanoic acid |
| 523 | 353 | Valeric anhydride | l-9,9-(1-chloromethylethylenedioxy)-15(S)-valeryloxy-prostanoic acid |
| 524 | 356 | Valeric anhydride | l-(1-chloromethylethylenedioxy)-16,16-dimethyl-15(S)-valeryloxy-prostanoic acid |
| 525 | 366 | Valeric anhydride | 9,9-(Propylenedioxy)-15-valeryloxy-7-nor-prostanoic acid |
| 526 | 370 | Valeric anhydride | l-9,9-(propylenedioxy)-15(S)-valeryloxy-prostanoic acid |
| 527 | 375 | Valeric anhydride | l-16,16-dimethyl-9,9-(propylenedioxy)-15(S)-valeryloxy-prostanoic acid |
| 528 | 390 | Valeric anhydride | 9,9-(Ethylenedithia)-15-valeryloxy-5,6,7,19,20-pentanor-prostanoic acid |
| 529 | 402 | Valeric anhydride | l-9,9-(ethylenedithia)-15(S)-valeryloxy-prostanoic acid |
| 530 | 403 | Valeric anhydride | l-9,9-(ethylenedithia)-16(R)-methyl-15(S)-valeryloxy-prostanoic acid |
| 531 | 407 | Valeric anhydride | l-9,9-(ethylenedithia)-16,16-dimethyl-15(S)-valeryloxy-prostanoic acid |
| 532 | 414 | Valeric anhydride | 9,9-(ethyleneoxythia)-15-valeryloxy-7,19,20-trinor-prostanoic acid |
| 533 | 423 | Valeric anhydride | l-9,9-(ethyleneoxythia)-15(S)-valeryloxy-prostanoic acid |
| 534 | 424 | Valeric anhydride | l-9,9-(ethyleneoxythia)-16(R)-methyl-15(S)-valeryloxy-prostanoic acid |
| 535 | 428 | Valeric anhydride | l-9,9-(ethyleneoxythia)-16,16-dimethyl-15(S)-valeryloxy-prostanoic acid |
| 536 | 316 | Octanoic anhydride | 9,9-(ethylenedioxy)-15-octanoyloxy-7a-homo-19,20-dinor-prostanoic acid |
| 537 | 325 | Octanoic anhydride | l-9,9-(ethylenedioxy)-16(R)-methyl-15(S)-octanoyloxy-prostanoic acid |
| 538 | 329 | Octanoic anhydride | l-9,9-(ethylenedioxy)-16,16-dimethyl-15(S)-octanoyloxy-prostanoic acid |
| 539 | 335 | Octanoic anhydride | 9,9-(1-methylethylenedioxy)-15-octanoyloxy-7a,7b-bishomo-19,20-dinor-prostanoic acid |
| 540 | 343 | Octanoic anhydride | 9,9-(1,2-dimethylethylenedioxy)-15-octanoyloxy-5,6,7-trinor-prostanoic acid |
| 541 | 352 | Octanoic anhydride | 9,9-(1-chloromethylethylenedioxy)-15-octanoyloxy-prostanoic acid |
| 542 | 353 | Octanoic anhydride | l-9,9-(1-chloromethylethylenedioxy)-15(S)-octanoyloxy-prostanoic acid |
| 543 | 356 | Octanoic anhydride | l-(1-chloromethylethylenedioxy)-16,16-dimethyl-15(S)-octanoyloxy-prostanoic acid |
| 544 | 367 | Octanoic anhydride | 15-octanoyloxy-9,9-(propylenedioxy)-7a-homo-prostanoic acid |
| 545 | 370 | Octanoic anhydride | l-15(S)-octanoyloxy-9,9-(propylenedioxy)-prostanoic acid |
| 546 | 375 | Octanoic anhydride | l-16,16-dimethyl-15(S)-octanoyloxy-9,9-(propylenedioxy)-prostanoic acid |
| 547 | 393 | Octanoic anhydride | 9,9-(ethylenedithia)-15-octanoyloxy-7,19,20-trinor-prostanoic acid |
| 548 | 402 | Octanoic anhydride | l-15(S)-acetoxy-9,9-(ethylenedithia)-prostanoic acid |
| 549 | 403 | Octanoic anhydride | l-9,9-(ethylenedithia)-16(R)-methyl-15(S)-octanoyloxy-prostanoic acid |
| 550 | 407 | Octanoic anhydride | l-9,9-(ethylenedithia)-16,16-dimethyl-15(S)-octanoyloxy-prostanoic acid |
| 551 | 417 | Octanoic anhydride | 9,9-(ethyleneoxythia)-15-octanoyloxy-6,7-dinor-prostanoic acid |
| 552 | 423 | Octanoic anhydride | l-9,9-(ethyleneoxythia)-15(S)-octanoyloxy-prostanoic acid |
| 553 | 424 | Octanoic anhydride | l-9,9-(ethyleneoxythia)-16(R)-methyl-15(S)-octanoyloxy-prostanoic acid |
| 554 | 428 | Octanoic anhydride | l-9,9-(ethyleneoxythia)-16,16-dimethyl-15(S)-octanoyloxy-prostanoic acid |
| 555 | 314 | Decanoic anhydride | 15-decanoyloxy-9,9-(ethylenedioxy)-7a,7b-bishomo-19,20-dinor-prostanoic acid |
| 556 | 325 | Decanoic anhy- | l-15(S)-decanoyloxy-9,9-(ethylene- |

TABLE 12-continued

| Example | Starting 15-ol of Example | Acylating reagent | Product |
|---|---|---|---|
| | | dride | dioxy)-16(R)-methyl-prostanoic acid |
| 557 | 329 | Decanoic anhydride | l-15(S)-decanoyloxy-9,9-(ethylenedioxy)-16,16-dimethylprostanoic acid |
| 558 | 350 | Decanoic anhydride | 9,9-(1-chloromethylethylenedioxy)-15-decanoyloxy-7-nor-prostanoic acid |
| 559 | 353 | Decanoic anhydride | l-9,9-(1-chloromethylethylenedioxy)-15(S)-decanoyloxy-prostanoic acid |
| 560 | 356 | Decanoic anhydride | l-(1-chloromethylethylenedioxy)-15(S)-16,16-dimethylprostanoic acid |
| 561 | 365 | Decanoic anhydride | 15-decanoyloxy-9,9-(propylenedioxy)-7a,7b-bishomo-prostanoic acid |
| 562 | 370 | Decanoic anhydride | l-15(S)-decanoyloxy-9,9-(propylenedioxy)-prostanoic acid |
| 563 | 375 | Decanoic anhydride | l-15(S)-decanoyloxy-16,16-dimethyl-9,9-(propylenedioxy)prostanoic acid |
| 564 | 395 | Decanoic anhydride | 15-decanoyloxy-9,9-(ethylenedithia)-5,6,7-trinor-prostanoic acid |
| 565 | 402 | Decanoic anhydride | l-15(S)-decanoyloxy-9,9-(ethylenedithia)-prostanoic acid |
| 566 | 403 | Decanoic anhydride | l-15(S)-decanoyloxy-9,9-(ethylenedithia)-16(R)-methyl-prostanoic acid |
| 567 | 407 | Decanoic anhydride | l-15(S)-decanoyloxy-9,9-(ethylenedithia)-16,16-dimethylprostanoic acid |
| 568 | 415 | Decanoic anhydride | 15-decanoyloxy-9,9-(ethyleneoxythia)-7a-homo-19,20-dinor-prostanoic acid |
| 569 | 423 | Decanoic anhydride | l-15(S)-decanoyloxy-9,9-(ethyleneoxythia)-prostanoic acid |
| 570 | 424 | Decanoic anhydride | l-15(S)-decanoyloxy-9,9-(ethyleneoxythia)-16(R)-methyl-prostanoic acid |
| 571 | 428 | Decanoic anhydride | l-15(S)-decanoyloxy-9,9-(ethyleneoxythia)-16,16-dimethylprostanoic acid |

EXAMPLES 572 – 734

Treatment of the various prostanoic acid ketals listed in Table 13 below with the indicated diazoalkanes in the manner described in Example 99 is productive of the esters of the Table.

TABLE 13

| Example | Starting acid ketal of Example | Diazoalkane | Product |
|---|---|---|---|
| 572 | 311 | Diazomethane | Methyl 9,9-(ethylenedioxy)-15-hydrox-19,20-dinor-prostanoate |
| 573 | 333 | Diazomethane | Methyl 15-hydroxy-9,9-(1-methyl-ethylenedioxy)-5,6,7,19,20-pentanor-prostanoate |
| 574 | 343 | Diazomethane | Methyl 9,9-(1,2-dimethylethylenedioxy)-15-hydroxy-5,6,7-trinor-prostanoate |
| 575 | 349 | Diazomethane | Methyl 9,9-(1-chloromethylethylenedioxy)-15-hydroxy-7a,7b-bishomo-prostanoate |
| 576 | 360 | Diazomethane | Methyl 15-hydroxy-9,9-(propylenedioxy)-7a,7b-bishomo-19,20-dinor-prostanoate |
| 577 | 394 | Diazomethane | Methyl 9,9-(ethylenedithia)-15-hydroxy-7a-homo-19,20-dinor-prostanoate |
| 578 | 419 | Diazomethane | Methyl 9,9-(ethyleneoxythia)-15-hydroxy-7-nor-prostanoate |
| 579 | 323 | Diazoethane | Ethyl l-9,9-(ethylenedioxy)-15(R)-hydroxy-prostanoate |
| 580 | 324 | Diazoethane | Ethyl l-9,9-(ethylenedioxy)-15(S)-hydroxy-prostanoate |
| 581 | 326 | Diazoethane | Ethyl l-9,9-(ethylenedioxy)-15(S)-hydroxy-16(S)-methyl-prostanoate |
| 582 | 329 | Diazoethane | Ethyl l-9,9-(ethylenedioxy)-15(S)-hydroxy-16,16-dimethyl-prostanoate |
| 583 | 330 | Diazoethane | Ethyl l-20-ethyl-9,9-(ethylenedioxy)-15(S)-hydroxy-prostanoate |
| 584 | 338 | Diazoethane | Ethyl l-15(S)-hydroxy-9,9-(1-methylethylenedioxy)-prostanoate |
| 585 | 339 | Diazoethane | Ethyl l-15(S)-hydroxy-16(R)-methyl-9,9-(1-methylethylenedioxy)-prostanoate |
| 586 | 341 | Diazoethane | Ethyl l-15(S)-hydroxy-16,16-dimethyl-9,9-(1-methylethylenedioxy)-prostanoate |

TABLE 13-continued

| Example | Starting acid ketal of Example | Diazoalkane | Product |
|---|---|---|---|
| 587 | 345 | Diazoethane | Ethyl l-9,9-(1,2-dimethylethylenedioxy)-15(S)-hydroxy-prostanoate |
| 588 | 346 | Diazoethane | Ethyl l-9,9-(1,2-dimethylethyleneoxy)-15(S)-hydroxy-16(R)-methyl-prostanoate |
| 589 | 348 | Diazoethane | Ethyl l-9,9-(1,2-dimethylethylenedioxy)-15(S)-hydroxy-16,16-dimethyl-prostanoate |
| 590 | 353 | Diazoethane | Ethyl l-9,9-(1-chloromethylethylenedioxy)-15(S)-hydroxy-prostanoate |
| 591 | 354 | Diazoethane | Ethyl l-9,9-(1-chloromethylethylenedioxy)-15(S)-hydroxy-16(R)-methyl-prostanoate |
| 592 | 356 | Diazoethane | Ethyl l-9,9-(1-chloromethylethylenedioxy)-15(S)-hydroxy-16,16-dimethyl-prostanoate |
| 593 | 370 | Diazoethane | Ethyl l-15(S)-hydroxy-9,9-(propylenedioxy)-prostanoate |
| 594 | 371 | Diazoethane | Ethyl l-15(S)-hydroxy-16(R)-methyl-9,9-(propylenedioxy)-prostanoate |
| 595 | 375 | Diazoethane | Ethyl l-15(S)-hydroxy-16,16-dimethyl-9,9-(propylenedioxy)-prostanoate |
| 596 | 402 | Diazoethane | Ethyl l-9,9-(ethylenedithia)-15(S)-hydroxy-prostanoate |
| 597 | 403 | Diazoethane | Ethyl l-9,9-(ethylenedithia)-15(S)-hydroxy-16(R)-methyl-prostanoate |
| 598 | 407 | Diazoethane | Ethyl l-9,9-(ethylenedithia)-15(S)-hydroxy-16,16-dimethyl-prostanoate |
| 599 | 423 | Diazoethane | Ethyl l-9,9-(ethyleneoxythia)-15(S)-hydroxy-prostanoate |
| 600 | 424 | Diazoethane | Ethyl l-9,9-(ethyleneoxythia)-15(S)-hydroxy-16(R)-methyl-prostanoate |
| 601 | 428 | Diazoethane | Ethyl l-9,9-(ethyleneoxythia)-15(S)-hydroxy-16,16-dimethyl-prostanoate |
| 602 | 316 | Diazobutane | Butyl 9,9-(ethylenedioxy)-15-hydroxy-7a-homo-19,20-dinor-prostanoate |
| 603 | 323 | Diazobutane | Butyl l-9,9-(ethylenedioxy)-15-(R)-hydroxy-prostanoate |
| 604 | 324 | Diazobutane | Butyl l-9,9-(ethylenedioxy)-15(S)-hydroxy-prostanoate |
| 605 | 326 | Diazobutane | Butyl l-9,9-(ethylenedioxy)-15(S)-hydroxy-16(S)-methyl-prostanoate |
| 606 | 329 | Diazobutane | Butyl l-9,9-(ethylenedioxy)-15(S)-hydroxy-16,16-dimethyl-prostanoate |
| 607 | 330 | Diazobutane | Butyl l-20-ethyl-9,9-(ethylenedioxy)-15(S)-hydroxy-prostanoate |
| 608 | 338 | Diazobutane | Butyl l-15(S)-hydroxy-9,9-(1-methylethylenedioxy)-prostanoate |
| 609 | 339 | Diazobutane | Butyl l-15(S)-hydroxy-16(R)-methyl-9,9-(1-methylethylenedioxy)-prostanoate |
| 610 | 341 | Diazobutane | Butyl l-15(S)-hydroxy-16,16-dimethyl-9,9-(1-methylethylenedioxy)-prostanoate |
| 611 | 345 | Diazobutane | Butyl l-9,9-(1,2-dimethylethylenedioxy)-15(S)-hydroxy-prostanoate |
| 612 | 346 | Diazobutane | Butyl l-9,9-(1,2-dimethylethylenedioxy)-15(S)-hydroxy-16(R)-methyl-prostanoate |
| 613 | 348 | Diazobutane | Butyl l-9,9-(1,2-dimethylethylenedioxy)-15(S)-hydroxy-16,16-dimethyl-prostanoate |
| 614 | 352 | Diazobutane | Butyl 9,9-(1-chloromethylethylenedioxy)-15-hydroxy-prostanoate |
| 615 | 353 | Diazobutane | Butyl l-9,9-(1-chloromethylethylenedioxy)-15(S)-hydroxy-prostanoate |
| 616 | 354 | Diazobutane | Butyl l-9,9-(1-chloromethylethylenedioxy)-15(S)-hydroxy-16(R)-methyl-prostanoate |
| 617 | 356 | Diazobutane | Butyl l-9,9-(1-chloromethylethylenedioxy)-15(S)-hydroxy-16,16-dimethyl-prostanoate |
| 618 | 363 | Diazobutane | Butyl 15-hydroxy-9,9-(propylenedioxy)-5,6,7-trinor-prostanoate |
| 619 | 364 | Diazobutane | Butyl 15-hydroxy-9,9-(propylenedioxy)-6,7-dinor-prostanoate |
| 620 | 370 | Diazobutane | Butyl l-15(S)-hydroxy-9,9- |

TABLE 13-continued

| Example | Starting acid ketal of Example | Diazoalkane | Product |
|---|---|---|---|
| 621 | 371 | Diazobutane | propylenedioxy)-prostanoate Butyl l-15(S)-hydroxy-16(R)-methyl-9,9-(propylenedioxy)-prostanoate |
| 622 | 375 | Diazobutane | Butyl l-15(S)-hydroxy-16,16-dimethyl-9,9-(propylenedioxy)-prostanoate |
| 623 | 382 | Diazobutane | Butyl 9,9-(2,2-dimethyl-(propylenedioxy)-15-hydroxy-7a,7b-bishomo-prostanoate |
| 624 | 390 | Diazobutane | Butyl 9,9-(ethylenedithia)-15-hydroxy-5,6,7,19,20-pentanor-prostanoate |
| 625 | 397 | Diazobutane | Butyl 9,9-(ethylenedithia)-15-hydroxy-7a,7b-bishomo-prostanoate |
| 626 | 402 | Diazobutane | Butyl l-9,9-(ethylenedithia)-15(S)-hydroxy-prostanoate |
| 627 | 403 | Diazobutane | Butyl l-9,9-(ethylenedithia)-15(S)-hydroxy-16(R)-methyl-prostanoate |
| 628 | 407 | Diazobutane | Butyl l-9,9-(ethylenedithia)-15(S)-hydroxy-16,16-dimethyl-prostanoate |
| 629 | 415 | Diazobutane | Butyl 9,9-(ethyleneoxythia)-15-hydroxy-7a-homo-19,20-dinor-prostanoate |
| 630 | 420 | Diazobutane | Butyl 9,9-(ethyleneoxythia)-15-hydroxy-7a-homo-prostanoate |
| 631 | 423 | Diazobutane | Butyl l-9,9-(ethyleneoxythia)-15(S)-hydroxy-prostanoate |
| 632 | 424 | Diazobutane | Butyl l-9,9-(ethyleneoxythia)-15(S)-hydroxy-16(R)-methyl-prostanoate |
| 633 | 428 | Diazobutane | Butyl l-9,9-(ethyleneoxythia)-15(S)-hydroxy-16,16-dimethyl-prostanoate |
| 634 | 320 | Diazohexane | Hexyl 9,9-(ethylenedioxy)-15-hydroxy-7-nor-prostanoate |
| 635 | 323 | Diazohexane | Hexyl l-9,9-(ethylenedioxy)-15-(R)-hydroxy-prostanoate |
| 636 | 324 | Diazohexane | Hexyl l-9,9-(ethylenedioxy)-15-(S)-hydroxy-prostanoate |
| 637 | 326 | Diazohexane | Hexyl l-9,9-(ethylenedioxy)-15-(S)-hydroxy-16(S)-methyl-prostanoate |
| 638 | 329 | Diazohexane | Hexyl l-9,9-(ethylenedioxy)-15-(S)-hydroxy-16,16-dimethyl-prostanoate |
| 639 | 330 | Diazohexane | Hexyl l-20-ethyl-9,9-(ethylenedioxy)-15(S)-hydroxy-prostanoate |
| 640 | 337 | Diazohexane | Hexyl 15-hydroxy-9,9-(1-methylethylenedioxy)-7a-homo-19,20-dinor-prostanoate |
| 641 | 338 | Diazohexane | Hexyl l-15(S)-hydroxy-9,9-(1-methylethylenedioxy)-prostanoate |
| 642 | 339 | Diazohexane | Hexyl 1-15(S)-hydroxy-16(R)-methyl-9,9-(1-methylethylenedioxy)-prostanoate |
| 643 | 341 | Diazohexane | Hexyl l-15(S)-hydroxy-16,16-dimethyl-9,9-(1-methylethylenedioxy)-prostanoate |
| 644 | 344 | Diazohexane | Hexyl 9,9-(1,2-dimethylethylenedioxy)-15-hydroxy-6,7-dinor-prostanoate |
| 645 | 345 | Diazohexane | Hexyl l-9,9-(1,2-dimethylethylenedioxy)-15(S)-hydroxy-prostanoate |
| 646 | 346 | Diazohexane | Hexyl l-9,9-(1,2-dimethylethylenedioxy)-15(S)-hydroxy-16(R)-methyl-prostanoate |
| 647 | 348 | Diazohexane | Hexyl l-9,9-(1,2-dimethylethylenedioxy)-15(S)-hydroxy-16,16-dimethyl-prostanoate |
| 648 | 351 | Diazohexane | Hexyl 9,9-(1-chloromethylethylenedioxy)-15-hydroxy-7a-homo-prostanoate |
| 649 | 353 | Diazohexane | Hexyl l-9,9-(1-chloromethylethylenedioxy)-15(S)-hydroxy-prostanoate |
| 650 | 354 | Diazohexane | Hexyl l-9,9-(1-chloromethylethylenedioxy)-15(S)-hydroxy-16(R)-methyl-prostanoate |
| 651 | 356 | Diazohexane | Hexyl l-9,9-(1-chloromethylethylenedioxy)-15(S)-hydroxy-16,16-dimethyl-prostanoate |
| 652 | 361 | Diazohexane | Hexyl 15-hydroxy-9,9-(propylenedioxy)-7,19,20-trinor-prostanoate |
| 653 | 370 | Diazohexane | Hexyl l-15(S)-hydroxy-9,9-(pro- |

TABLE 13-continued

| Example | Starting acid ketal of Example | Diazoalkane | Product |
|---|---|---|---|
| | | | pylenedioxy)-prostanoate |
| 654 | 371 | Diazohexane | Hexyl l-15(S)-hydroxy-16(R)-methyl-9,9-(propylenedioxy)-prostanoate |
| 655 | 375 | Diazohexane | Hexyl l-15(S)-hydroxy-16,16-dimethyl-9,9-(propylenedioxy)-prostanoate |
| 656 | 389 | Diazohexane | Hexyl 9,9-(ethylenedithia)-15-hydroxy-19,20-dinor-prostanoate |
| 657 | 402 | Diazohexane | Hexyl l-9,9-(ethylenedithia)-15(S)-hydroxy-prostanoate |
| 658 | 403 | Diazohexane | Hexyl 9,9-(ethylenedithia)-15(S)-hydroxy-16(R)-methyl-prostanoate |
| 659 | 407 | Diazohexane | Hexyl l-9,9-(ethylenedithia)-15(S)-hydroxy-16,16-dimethyl-prostanoate |
| 660 | 418 | Diazohexane | Hexyl 9,9-(ethyleneoxythia)-15-hydroxy-7a,7b-bishomo-prostanoate |
| 661 | 423 | Diazohexane | Hexyl l-9,9-(ethyleneoxythia)-15(S)-hydroxy-prostanoate |
| 662 | 424 | Diazohexane | Hexyl l-9,9-(ethyleneoxythia)-15(S)-hydroxy-16(R)-methyl-prostanoate |
| 663 | 428 | Diazohexane | Hexyl l-9,9-(ethyleneoxythia)-15(S)-hydroxy-16,16-dimethyl-prostanoate |
| 664 | 311 | Diazooctane | Octyl 9,9-(ethylenedioxy)-15-hydroxy-19,20-dinor-prostanoate |
| 665 | 313 | Diazooctane | Octyl 9,9-(ethylenedioxy)-15-hydroxy-6,7,19,20-tetranor-prostanoate |
| 666 | 316 | Diazooctane | Octyl 9,9-(ethylenedioxy)-15-hydroxy-7a-homo-19,20-dinor-prostanoate |
| 667 | 319 | Diazooctane | Octyl 9,9-(ethylenedioxy)-7a,-7b-bishomo-prostanoate |
| 668 | 323 | Diazooctane | Octyl l-9,9-(ethylenedioxy)-15-(R)-hydroxy-prostanoate |
| 669 | 324 | Diazooctane | Octyl l-9,9-(ethylenedioxy)-15(S)-hydroxy-prostanoate |
| 670 | 326 | Diazooctane | Octyl l-9,9-(ethylenedioxy)-15(S)-hydroxy-16(S)-methyl-prostanoate |
| 671 | 329 | Diazooctane | Octyl l-9,9-(ethylenedioxy)-15(S)-hydroxy-16,16-dimethyl-prostanoate |
| 672 | 330 | Diazooctane | Octyl l-20-ethyl-9,9-(ethylenedioxy)-15(S)-hydroxy-prostanoate |
| 673 | 338 | Diazooctane | Octyl l-15(S)-hydroxy-9,9-(1-methylethylenedioxy)prostanoate |
| 674 | 339 | Diazooctane | Octyl l-15(S)-hydroxy-16(R)-methyl-9,9-(1-methylethylenedioxy)-prostanoate |
| 675 | 341 | Diazooctane | Octyl l-15(S)-hydroxy-16,16-dimethyl-9,9-(1-methylethylenedioxy)-prostanoate |
| 676 | 345 | Diazooctane | Octyl l-9,9-(1,2-dimethylethylenedioxy)-15(S)-hydroxy-prostanoate |
| 677 | 346 | Diazooctane | Octyl l-9,9-(1,2-dimethylethylenedioxy)-15(S)-hydroxy-16(R)-methyl-prostanoate |
| 678 | 348 | Diazooctane | Octyl l-9,9-(1,2-dimethylethylenedioxy)-15(S)-hydroxy-16,16-dimethyl-prostanoate |
| 679 | 350 | Diazooctane | Octyl 9,9-(1-chloromethyl-ethylenedioxy)-15-hydroxy-7-nor-prostanoate |
| 680 | 353 | Diazooctane | Octyl l-9,9-(1-chloromethyl-ethylenedioxy)-15(S)-hydroxy-prostanoate |
| 681 | 354 | Diazooctane | Octyl l-9,9-(1-chloromethyl-ethylenedioxy)-15(S)-hydroxy-16(R)-methyl-prostanoate |
| 682 | 356 | Diazooctane | Octyl l-9,9-(1-chloromethyl-ethylenedioxy)-15(S)-hydroxy-16,16-dimethyl-prostanoate |
| 683 | 361 | Diazooctane | Octyl 15-hydroxy-9,9-(propylenedioxy)-7,19,20-trinor-prostanoate |
| 684 | 365 | Diazooctane | Octyl 15-hydroxy-9,9-(propylenedioxy)-7a,7b-bishomo-prostanoate |
| 685 | 370 | Diazooctane | Octyl l-15(S)-hydroxy-9,9-(propylenedioxy)-prostanoate |
| 686 | 371 | Diazooctane | Octyl l-15(S)-hydroxy-16(R)-methyl-9,9-(propylenedioxy)-prostanoate |
| 687 | 375 | Diazooctane | Octyl l-15(S)-hydroxy-16,16-dimethyl-9,9-(propylenedioxy)-prostanoate |
| 688 | 394 | Diazooctane | Octyl 9,9-(ethylenedithia)-15- |

TABLE 13-continued

| Example | Starting acid ketal of Example | Diazoalkane | Product |
|---|---|---|---|
| | | | hydroxy-7a-homo-19,20-dinor-prostanoate |
| 689 | 397 | Diazooctane | Octyl 9,9-(ethylenedithia)-15-hydroxy-7a,7b-bishomo-prostanoate |
| 690 | 402 | Diazooctane | Octyl l-9,9-(ethylenedithia)-15-(S)-hydroxy-prostanoate |
| 691 | 404 | Diazooctane | Octyl l-9,9-(ethylenedithia)-15-(S)-hydroxy-16(S)-methyl-prostanoate |
| 692 | 407 | Diazooctane | Octyl l-9,9-(ethylenedithia)-15(S)-hydroxy-16,16-dimethyl-prostanoate |
| 693 | 412 | Diazooctane | Octyl 9,9-(ethyleneoxythia)-15-hydroxy-6,7,19,20-tetra-nor-prostanoate |
| 694 | 419 | Diazooctane | Octyl 9,9-(ethyleneoxythia)-7-nor-prostanoate |
| 695 | 423 | Diazooctane | Octyl l-9,9-(ethyleneoxythia)-15(S)-hydroxy-prostanoate |
| 696 | 424 | Diazooctane | Octyl 9,9-(ethyleneoxythia)-15(S)-hydroxy-16(R)-methyl-prostanoate |
| 697 | 428 | Diazooctane | Octyl l-9,9-(ethyleneoxythia)-15(S)-hydroxy-16,16-dimethyl-prostanoate |
| 698 | 313 | Diazodecane | Decyl 9,9-(ethylenedioxy)-15-hydroxy-6,7,19,20-tetranor-prostanoate |
| 699 | 316 | Diazodecane | Decyl 9,9-(ethylenedioxy)-15-hydroxy-7a-homo-19,20-dinor-prostanoate |
| 700 | 319 | Diazodecane | Decyl 9,9-(ethylenedioxy)-15-hydroxy-7a,7b-bishomo-prostanoate |
| 701 | 323 | Diazodecane | Decyl l-9,9-(ethylenedioxy)-15(R)-hydroxy-prostanoate |
| 702 | 324 | Diazodecane | Decyl l-9,9-(ethylenedioxy)-15(S)-hydroxy-prostanoate |
| 703 | 326 | Diazodecane | Decyl l-9,9-(ethylenedioxy)-15-(S)-hydroxy-16(S)-methyl-prostanoate |
| 704 | 329 | Diazodecane | Decyl l-9,9-(ethylenedioxy)-15(S)-hydroxy-16,16-di-methyl-prostanoate |
| 705 | 330 | Diazodecane | Decyl l-20-ethyl-9,9-(ethyl-enedioxy)-15(S)-hydroxy-prostanoate |
| 706 | 338 | Diazodecane | Decyl l-15(S)-hydroxy-9,9-(1-methylethylenedioxy)-prostanoate |
| 707 | 339 | Diazodecane | Decyl l-15(S)-hydroxy-16(R)-methyl-9,9-(1-methylethyl-enedioxy)-prostanoate |
| 708 | 341 | Diazodecane | Decyl l-15(S)-hydroxy-16,16-dimethyl-9,9-(1-methylethyl-enedioxy)-prostanoate |
| 709 | 345 | Diazodecane | Decyl l-9,9-(1,2-dimethyl-ethylenedioxy)-15(S)-hydroxy-prostanoate |
| 710 | 346 | Diazodecane | Decyl l-9,9-(1,2-dimethyl-ethylenedioxy)-15(S)-hydroxy-16(R)-methyl-prostanoate |
| 711 | 348 | Diazodecane | Decyl l-9,9-(1,2-dimethyl-ethylenedioxy)-15(S)-hydroxy-16,16-dimethyl-prostanoate |
| 712 | 353 | Diazodecane | Decyl l-9,9-(1-chloromethyl-ethylenedioxy)-15(S)-hydroxy-prostanoate |
| 713 | 354 | Diazodecane | Decyl l-9,9-(1-chloromethyl-ethylenedioxy)-15(S)-hydroxy-16(R)-methyl-prostanoate |
| 714 | 356 | Diazodecane | Decyl l-9,9-(1-chloromethyl-ethylenedioxy)-15(S)-hydroxy-16,16-dimethyl-prostanoate |
| 715 | 359 | Diazodecane | Decyl 15-hydroxy-9,9-(propyl-enedioxy)-6,7,19,20-tetranor-prostanoate |
| 716 | 366 | Diazodecane | Decyl 15-hydroxy-9,9-(propyl-enedioxy)-7-nor-prostanoate |
| 717 | 367 | Diazodecane | Decyl 15-hydroxy-9,9-(propyl-enedioxy)-7a-homo-prostanoate |
| 718 | 370 | Diazodecane | Decyl l-15(S)-hydroxy-(9,9-propylenedioxy)-prostanoate |
| 719 | 371 | Diazodecane | Decyl l-15(S)-hydroxy-16(R)-methyl-9,9-(propylenedioxy)-prostanoate |
| 720 | 375 | Diazodecane | Decyl l-15(S)-hydroxy-16,16-dimethyl-9,9-(propylenedioxy)-prostanoate |
| 721 | 381 | Diazodecane | Decyl 9,9-(2,2-dimethylpropyl- |

TABLE 13-continued

| Example | Starting acid ketal of Example | Diazoalkane | Product |
|---|---|---|---|
| | | | enedioxy)-15-hydroxy-6,7-dinor-prostanoate |
| 722 | 390 | Diazodecane | Decyl 9,9-(ethylenedithia)-15-hydroxy-5,6,7,19,20-pentanor-prostanoate |
| 723 | 393 | Diazodecane | Decyl 9,9-(ethylenedithia)-15-hydroxy-7,19,20-trinor-prostanoate |
| 724 | 396 | Diazodecane | Decyl 9,9-(ethylenedithia)-15-hydroxy-6,7-dinor-prostanoate |
| 725 | 399 | Diazodecane | Decyl 9,9-(ethylenedithia)-15-hydroxy-7a-homo-prostanoate |
| 726 | 402 | Diazodecane | Decyl l-9,9-(ethylenedithia)-15(S)-hydroxy-prostanoate |
| 727 | 403 | Diazodecane | Decyl l-9,9-(ethylenedithia)-15(S)-hydroxy-16(R)-methyl-prostanoate |
| 728 | 407 | Diazodecane | Decyl l-9,9-(ethylenedithia)-15(S)-hydroxy-16,16-dimethyl-prostanoate |
| 729 | 410 | Diazodecane | Decyl 9,9-(ethyleneoxythia)-15-hydroxy-19,20-dinor-prostanoate |
| 730 | 413 | Diazodecane | Decyl 9,9-(ethyleneoxythia)-15-hydroxy-7a,7b-bis-homo-19,20-dinor-prostanoate |
| 731 | 418 | Diazodecane | Decyl 9,9-(ethyleneoxythia)-15-hydroxy-7a,7b-bishomo-prostanoate |
| 732 | 423 | Diazodecane | Decyl l-9,9-(ethyleneoxythia)-15(S)-hydroxy-prostanoate |
| 733 | 424 | Diazodecane | Decyl l-9,9-(ethyleneoxythia)-15(S)-hydroxy-16(R)-methyl-prostanoate |
| 734 | 428 | Diazodecane | Decyl l-9,9-(ethyleneoxythia)-15(S)-hydroxy-16,16-dimethyl-prostanoate |

EXAMPLE 735

Preparation of 1-methyl 9,9-(ethylenedioxy)-15-oxo-prostanoate

To a mixture of 14.5 g. of chromium trioxide-pyridine complex in 110 ml. of dry methylene chloride is added with stirring 4.82 g. of 1-methyl 9,9-(ethylenedioxy)-15(S)-hydroxy-prostanoate (Example 134) in 17 ml. of methylene chloride. The resulting dark brown mixture is stirred at ambient temperature for 18 hours. The mixture is filtered and the mother liquor is taken to dryness. The residue is taken up in ether and washed successively with ice cold 5% sodium hydroxide, saturated sodium chloride solution, 30% sodium phosphate monobasic solution and water dried with anhydrous sodium sulfate and evaporated to dryness under reduced pressure to afford 4.17 g. (98%) of product as an oil; λ max 5.71, 5.82μ (carbonyl groups).

EXAMPLE 736

Preparation of 1-methyl-9,9-(ethylenedioxy)-15-hydroxy-15-methyl-prostanoate

To a Grignard solution prepared from 363 mg. (2 equivalents) of magnesium and 2.16 g. (2 equivalents) of methyl iodide in 10 ml. of ether under argon atmosphere is added dropwise a solution of 3 g. of 1-methyl 9,9-(ethylenedioxy)-15-oxo-prostanoate (Example 735) in 15 ml. of ether and the resulting mixture is stirred at ambient temperature for 18 hours. Saturated ammonium chloride (20 ml.) is added followed by 15 ml. of water and 50 ml. of ether. The ethereal solution is washed with saturated sodium chloride solution, dried with anhydrous sodium sulfate and taken to dryness to give 3.04 g. of viscous oil. This material is chromatographed on 75 g. of Florisil. The product is eluted with benzene to give 880 mg. of product. Further elution of the column with 10% ether in benzene gives 1.3 g. of 1-1,1-dimethyl-15-methyl-15-hydroxy-9,9-ethylenedioxy-prostanyl alcohol.

EXAMPLE 737

Preparation of 1-9,9-(ethylenedioxy)-15-hydroxy-15-methyl-prostanoic acid

Treatment of 1-methyl 9,9-(ethylenedioxy)-15-hydroxy-15-methyl-prostanoate (Example 736) with potassium hydroxide in the manner of Example 58 is productive of the subject compound.

EXAMPLES 738 – 744

Treatment of the various hydroxyprostanoate ketals of Table 14 below with chromium trioxide-pyridine complex in the manner of Example 735 above is productive of the corresponding 15-oxoprostanoate ketals of the Table.

TABLE 14

| Example | Starting 15-hydroxyprostanoate ketals of Example | Product 15-oxoprostanoate ketals |
|---|---|---|
| 738 | 140 | methyl l-20-ethyl-9,9-(ethylenedioxy)-15-oxoprostanoate |
| 739 | 141 | ent-methyl 9,9-(ethylenedioxy)-15-oxoprostanoate |
| 740 | 148 | methyl l-9,9-(1-methyl-ethylenedioxy)-15-oxoprostanoate |
| 741 | 194 | methyl l-15-oxo-9,9-(propylenedioxy)- |

TABLE 14-continued

| Example | Starting 15-hydroxyprostanoate ketals of Example | Product 15-oxoprostanoate ketals |
|---|---|---|
| 742 | 200 | prostanoate methyl l-20-ethyl-15-oxo-9,9-(propylenedioxy)-prostanoate |
| 743 | 201 | ent-methyl 15-oxo-9,9-(propylenedioxy)-prostanoate |
| 744 | 212 | methyl l-9,9-(2,2-dimethylpropylenedioxy)-15-oxoprostanoate |

EXAMPLES 745–751

Treatment of the various 15-oxoprostanoate ketals of Table 15 below with methyl magnesium iodide in the manner of Example 736 is productive of the corresponding 15-hydroxy-15-methyl prostanoate ketals of the table. The products are obtained as a mixture of the 15(S) and 15(R) components.

TABLE 15

| Example | Starting 15-oxo-prostanoate ketals of Example | Product 15-hydroxy-15-methyl-prostanoate ketals |
|---|---|---|
| 745 | 738 | methyl l-20-ethyl-9,9-(ethylenedioxy)-15-hydroxy-15-methyl-prostanoate |
| 746 | 739 | ent-methyl 9,9-(ethylenedioxy)-15-hydroxy-15-methylprostanoate |
| 747 | 740 | methyl l-15-hydroxy-15-methyl-9,9-(1-methylethylenedioxy)-prostanoate |
| 748 | 741 | methyl l-15-hydroxy-15-methyl-9,9-(propylenedioxy)prostanoate |
| 749 | 742 | methyl l-20-ethyl-15-hydroxy-15-methyl-9,9-(propylenedioxy)-prostanoate |
| 750 | 743 | ent-methyl 15-hydroxy-15-methyl-9,9-(propylenedioxy)prostanoate |
| 751 | 744 | methyl l-9,9-(2,2-dimethylpropylenedioxy)-15-hydroxy-15-methyl-prostanoate |

EXAMPLES 752–759

Saponification of the various 15-hydroxy-15-methyl-prostanoate ketals of Table 16 below in the manner of Example 58 is productive of the corresponding 15-hydroxy-15-methyl-prostanoic acid ketals of the Table.

TABLE 16

| Example | Starting 15-hydroxy-15-methyl-prostanoate ketals of Example | Product 15-hydroxy-15-methyl-prostanoic acid ketal |
|---|---|---|
| 752 | 736 | l-9,9-(ethylenedioxy)-15-hydroxy-15-methyl-prostanoic acid |
| 753 | 745 | l-20-ethyl-9,9-(ethylenedioxy)-15-hydroxy-15-methylprostanoic acid |
| 754 | 746 | ent-9,9-(ethylenedioxy)-15-hydroxy-15-methylprostanoic acid |
| 755 | 747 | l-15-hydroxy-15-methyl-9,9-(1-methylethylenedioxy)prostanoic acid |
| 756 | 748 | l-15-hydroxy-15-methyl-9,9-(propylenedioxy)-prostanoic acid |
| 757 | 749 | l-20-ethyl-15-hydroxy-15-methyl-9,9-(propylenedioxy)prostanoic acid |
| 758 | 750 | ent-15-hydroxy-15-methyl-9,9-(propylenedioxy)prostanoic acid |
| 759 | 751 | l-9,9-(2,2-dimethylpropylenedioxy)-15-hydroxy-15-methylprostanoic acid |

EXAMPLES 760–763

In the manner described in Example 99, treatment of the various prostatrienoic acids listed in Table 17 below with ethereal diazomethane is productive of the corresponding methyl prostatrienoates of the Table.

TABLE 17

| Example | Starting prostatrienoic acids | Product Methyl prostatrienoates |
|---|---|---|
| 760 | l-16-fluoro-15(S)-hydroxy-9-oxo-5-cis,10,13-trans-prostatrienoic acid[1] | l-methyl 16-fluoro-15(S)-hydroxy-9-oxo-5-cis,10,13-trans-prostatrienoate |
| 761 | l-16-fluoro-15(R)-hydroxy-9-oxo-5-cis,10,13-trans-prostatrienoic acid[1] | l-methyl 16-fluoro-15(R)-hydroxy-9-oxo-5-cis,10,13-trans-prostatrienoate |
| 762 | l-16,16-difluoro-15(S)-hydroxy-9-oxo-5-cis,10,13-trans-prostatrienoic acid[1] | l-methyl 16,16-difluoro-15(S)-hydroxy-9-oxo-5-cis,10,13-trans-prostatrienoate |
| 763 | l-16,16-difluoro-15(R)-hydroxy-9-oxo-5-cis,10,13-trans-prostatrienoic acid[1] | l-methyl 16,16-difluoro-15(R)-hydroxy-9-oxo-5-cis,10,13-trans-prostatrienoate |

[1] Netherlands Patent No. 7,305,817.

EXAMPLES 764–767

Hydrogenation of the various prostatrienoic acid methyl esters in Table 18 below using 5% rhodium-on-carbon catalyst in ethyl acetate all in the manner described in Example 52 above is productive of the prostanoic acid methyl esters of the Table.

TABLE 18

| Example | Starting prostatrienoic acid methyl esters of Example | Product Prostanoic acid methyl esters |
|---|---|---|
| 764 | 760 | l-methyl 16-fluoro-15(S)-hydroxy-9-oxo-prostanoate |
| 765 | 761 | l-methyl 16-fluoro-15(R)-hydroxy-9-oxo-prostanoate |
| 766 | 762 | l-methyl 16,16-difluoro- |

TABLE 18-continued

| Example | Starting prosta-trienoic acid methyl esters of Example | Product Prostanoic acid methyl esters |
|---|---|---|
| | | 15(S)-hydroxy-9-oxo-prostanoate |
| 767 | 763 | 1-methyl 16,16-difluoro-15(R)-hydroxy-9-oxo-prostanoate |

EXAMPLES 768–787

Treatment of the various 9-oxoprostanoates listed in Table 19 below with the indicated reagent, by the method described in Example 55 above, is productive of the ketals of the Table.

TABLE 19

| Example | Starting 9-oxo-prostanoates of Example | Ketalizing reagent | Product Prostanoate ketals |
|---|---|---|---|
| 768 | 764 | ethylene glycol | l-methyl 9,9-(ethylenedioxy)-16-fluoro-15(S)-hydroxyprostanoate |
| 769 | 764 | 1,2-propanediol | l-methyl 16-fluoro-15(S)-hydroxy-9,9-(1-methylethylenedioxy)prostanoate |
| 770 | 764 | 1-chloro-2,3-propanediol | l-methyl 9,9-(1-chloromethylethylenedioxy)-16-fluoro-15(S)-hydroxyprostanoate |
| 771 | 764 | 2,3-butanediol | l-methyl 9,9-(1,2-dimethylethylenedioxy)-16-fluoro-15(S)-hydroxyprostanoate |
| 772 | 764 | 1,3-propanediol | l-methyl 16-fluoro-15(S)-hydroxy-9,9-(propylenedioxy)prostanoate |
| 773 | 765 | ethylene glycol | l-methyl 9,9-(ethylenedioxy)-16-fluoro-15(R)-hydroxyprostanoate |
| 774 | 765 | 1,2-propanediol | l-methyl 16-fluoro-15(R)-hydroxy-9,9-(1-methylethylenedioxy)prostanoate |
| 775 | 765 | 1-chloro-2,3-propanediol | l-methyl 9,9-(1-chloromethylethylenedioxy)-16-fluoro-15(R)-hydroxyprostanoate |
| 776 | 765 | 2,3-butanediol | l-methyl 9,9-(1,2-dimethylethylenedioxy)-16-fluoro-15(R)-hydroxyprostanoate |
| 777 | 765 | 1,3-propanediol | l-methyl 16-fluoro-15(R)-hydroxy-9,9-(propylenedioxy)prostanoate |
| 778 | 766 | ethylene glycol | l-methyl 9,9-(ethylenedioxy)-16,16-difluoro-15(S)-hydroxyprostanoate |
| 779 | 766 | 1,2-propanediol | l-methyl 16,16-difluoro-15(S)-hydroxy-9,9-(1-methylethylenedioxy)prostanoate |
| 780 | 766 | 1-chloro-2,3-propanediol | l-methyl 9,9-(1-chloromethylethylenedioxy)-16,16-difluoro-15(S)-hydroxyprostanoate |
| 781 | 766 | 2,3-butanediol | l-methyl 9,9-(1,2-dimethylethylenedioxy)-16,16-difluoro-15(S)-hydroxyprostanoate |
| 782 | 766 | 1,3-propanediol | l-methyl 16,16-difluoro-15(S)-hydroxy-9,9-(propylenedioxy)prostanoate |
| 783 | 767 | ethylene glycol | l-methyl 9,9-(ethylenedioxy)-16,16-difluoro-15(R)-hydroxyprostanoate |
| 784 | 767 | 1,2-propanediol | l-methyl 16,16-difluoro-15(R)-hydroxy-9,9-(1-methylethylenedioxy)prostanoate |
| 785 | 767 | 1-chloropropanediol | l-methyl-9,9-(1-chloromethylethylenedioxy)-16,16-difluoro-15(R)-hydroxyprostanoate |
| 786 | 767 | 2,3-butanediol | l-methyl 9,9-(1,2-dimethylethylenedioxy)-16,16-difluoro-15(R)-hydroxyprostanoate |
| 787 | 767 | 1,3-propanediol | l-methyl 16,16-difluoro-15(R)-hydroxy-9,9-(propylenedioxy)prostanoate |

EXAMPLES 788–807

Saponification of the various prostanoate ketals of Table 20 below in the manner of Example 58 above is productive of the prostanoic acid ketals of the Table.

TABLE 20

| Example | Starting Prostanoate ketals of Example | Product Prostanoic Acid Ketals |
|---|---|---|
| 788 | 768 | l-9,9-(ethylenedioxy)-16-fluoro-15(S)-hydroxy prostanoic acid |
| 789 | 769 | l-16-fluoro-15(S)-hydroxy-9,9-(1-methylethylenedioxy)-prostanoic acid |
| 790 | 770 | l-9,9-(1-chloromethylethylenedioxy)-16-fluoro-15-(S)-hydroxy-prostanoic acid |
| 791 | 771 | l-9,9-(1,2-dimethylethylenedioxy)-16-fluoro-15(S)-hydroxy prostanoic acid |
| 792 | 772 | l-16-fluoro-15(S)-hydroxy-9,9-(propylenedioxy)prostanoic acid |
| 793 | 773 | l-9,9-(ethylenedioxy)-16-fluoro-15(R)-hydroxy prostanoic acid |
| 794 | 774 | l-16-fluoro-15(R)-hydroxy-9,9-(1-methylethylenedioxy)-prostanoic acid |
| 795 | 775 | l-9,9-(1-chloromethylethylenedioxy)-16-fluoro-15(R)-hydroxy prostanoic acid |
| 796 | 776 | l-9,9-(1,2-dimethylethylenedioxy-16-fluoro-15(R)-hydroxy-prostanoic acid |
| 797 | 777 | l-16-fluoro-15(R)-hydroxy-9,9-(propylenedioxy)prostanoic acid |
| 798 | 778 | l-9,9-(ethylenedioxy)-16,16-difluoro-15(S)-hydroxy prostanoic acid |
| 799 | 779 | l-16,16-difluoro-15(S)-hydroxy-9,9-(1-methylethylenedioxy)-prostanoic acid |
| 800 | 780 | l-9,9-(1-chloromethylethylenedioxy)-16,16-difluoro-15(S)-hydroxy prostanoic acid |

TABLE 20-continued

| Example | Starting Prostanoate ketals of Example | Product Prostanoic Acid Ketals |
|---|---|---|
| 801 | 781 | l-9,9-(1,2-dimethylethylenedioxy)-16,16-difluoro-15(S)-hydroxy prostanoic acid |
| 802 | 782 | l-16,16-difluoro-15(S)-hydroxy-9,9-(propylenedioxy)prostanoic acid |
| 803 | 783 | l-9,9-(ethylenedioxy)-16,16-difluoro-15(R)-hydroxy prostanoic acid |
| 804 | 784 | l-16,16-difluoro-15(R)-hydroxy-9,9-(1-methylethylenedioxy)-prostanoic acid |
| 805 | 785 | l-9,9-(1-chloromethylethylenedioxy)-16,16-difluoro-15(R)-hydroxy prostanoic acid |
| 806 | 786 | l-9,9-(1,2-dimethylethylenedioxy)-16,16-difluoro-15(R)-hydroxy prostanoic acid |
| 807 | 787 | l-16,16-difluoro-15(R)-hydroxy-9,9-(propylenedioxy)prostanoic acid |

EXAMPLES 808–814

Treatment of the various prostatrienoic acids listed in Table 21 below with the indicated diazoalkanes, in the manner described in Example 99 above is productive of the esters of the Table.

TABLE 21

| Example | Starting Prostatrienoic Acid | Diazoalkane | Product |
|---|---|---|---|
| 808 | l-16-fluoro-15(S)-hydroxy-9-oxo-5-cis,10,13-trans-prostatrienoic acid[1] | diazobutane | l-butyl 16-fluoro-15(S)-hydroxy-9-oxo-5-cis,10,13-trans-prostatrienoate |
| 809 | l-16-fluoro-15(S)-hydroxy-9-oxo-5-cis,10,13-trans-prostatrienoic acid | diazodecane | l-decyl 16-fluoro-15(S)-hydroxy-9-oxo-5-cis,10,13-trans-prostatrienoate |
| 810 | l-16-fluoro-15(R)-hydroxy-9-oxo-5-cis,10,13-trans-prostatrienoic acid[1] | diazopentane | l-pentyl 16-fluoro-15(R)-hydroxy-9-oxo-5-cis,10,13-trans-prostatrienoate |
| 811 | l-16-fluoro-15(R)-hydroxy-9-oxo-5-cis,10,13-trans-prostatrienoic acid[1] | diazononane | l-nonyl 16-fluoro-15(R)-hydroxy-9-oxo-5-cis,10,13-trans-prostatrienoate |
| 812 | l-16,16-difluoro-15(S)-hydroxy-9-oxo-5-cis,10,13-trans-prostatrienoic acid[1] | diazohexane | l-hexyl 16,16-difluoro-15(S)-hydroxy-9-oxo-5-cis,10,13-trans-prostatrienoate |
| 813 | l-16,16-difluoro-15(S)-hydroxy-9-oxo-5-cis,10,13-trans-prostatrienoic acid | diazooctane | l-octyl 16,16-difluoro-15(S)-hydroxy-9-oxo-5-cis,10,13-trans-prostatrienoate |
| 814 | l-16,16-difluoro-15(R)-hydroxy-9-oxo-5-cis,10,13-trans-prostatrienoic acid | diazoheptane | l-heptyl 16,16-difluoro-15(R)-hydroxy-9-oxo-5-cis,10,13-trans-prostatrienoate |

[1]Netherlands Patent No. 7,305,817

EXAMPLES 815–821

Hydrogenation of the various prostatrienoic acid esters in Table 22 below in the manner described in Example 52 above is productive of the prostanoic acid esters of the Table.

TABLE 22

| Example | Starting Prostatrienoic Acid Esters of Example | Product Prostanoic Acid Esters |
|---|---|---|
| 815 | 808 | l-butyl 16-fluoro-15(S)-hydroxy-9-oxo prostanoate |
| 816 | 809 | l-decyl 16-fluoro-15(S)-hydroxy 9-oxo prostanoate |
| 817 | 810 | l-pentyl 16-fluoro-15(R)-hydroxy-9-oxo prostanoate |
| 818 | 811 | l-nonyl 16-fluoro-15(R)-hydroxy-9-oxo prostanoate |
| 819 | 812 | l-hexyl 16,16-difluoro-15(S)-hydroxy-9-oxo prostanoate |
| 820 | 813 | l-octyl 16,16-difluoro-15(S)-hydroxy-9-oxo prostanoate |
| 821 | 814 | l-heptyl 16,16-difluoro-15(R)-hydroxy-9-oxo prostanoate |

EXAMPLES 822–825

Saponification of the various prostanoate methyl esters of Table 23 below in the manner of Example 58 above is productive of the prostanoic acids of the Table.

TABLE 22

| Example | Starting Prostanoic Acid Ester of Example | Product Prostanoic Acids |
|---|---|---|
| 822 | 764 | l-16-fluoro-15(S)-hydroxy-9-oxoprostanoic acid |

TABLE 22-continued

| Example | Starting Prostanoic Acid Ester of Example | Product Prostanoic Acids |
|---|---|---|
| 823 | 765 | 1-16-fluoro-15(R)-hydroxy-9-oxoprostanoic acid |
| 824 | 766 | 1-16,16-difluoro-15(S)-hydroxy-9-oxoprostanoic acid |
| 825 | 767 | 1-16,16-difluoro-15(R)-hydroxy-9-oxoprostanoic acid |

EXAMPLE 826

Preparation of 1-9α,15(S)-dihydroxy-16-fluoro-prostanoic acid

To a solution of 435 mg. of 1-16-fluoro-15(S)-hydroxy-9-oxoprostanoic acid (Example 822) in 4.5 ml. of tetrahydrofuran, stirred in an ice bath under argon atmosphere, is added dropwise 3.7 ml. of 0.76 M lithium perhydro-9b-boraphenalyl hydride. After 40 minutes at 0° C. there is added 1.62 ml. of 3N sodium hydroxide followed by 1.62 ml. of 30% hydrogen peroxide. Ether is added and the resulting solution is acidified with 2N hydrochloric acid. The ether layer is washed several times with saturated sodium chloride solution, dried with anhydrous magnesium sulfate and taken to dryness to give the subject product as an oil.

EXAMPLES 827–829

Treatment of the 9-oxo-derivative designated in Table 23 below with lithium perhydro-9b-boraphenalyl hydride by the procedure described in Example 826 provides the 9α, 15-dihydroxy derivatives of the Table.

TABLE 23

| Example | Starting 9-oxo prostanoic acid of Example | Product 9α, 15-dihydroxy Derivative |
|---|---|---|
| 827 | 823 | 1-9α,15(R)-dihydroxy-16-fluoroprostanoic acid |
| 828 | 824 | 1-9α,15(S)-dihydroxy-16,16-difluoroprostanoic acid |
| 829 | 825 | 1-9α,15(R)-dihydroxy-16,16-difluoroprostanoic acid |

EXAMPLES 830–836

Treatment of the various prostanoic acids listed in Table 24 below with the indicated diazoalkanes in the manner described in Example 99 above is productive of the esters of the Table.

TABLE 24

| Example | Starting prostanoic acid of Example | Diazoalkane | Product Prostanoic Acid Ester |
|---|---|---|---|
| 830 | 826 | diazomethane | 1-methyl 9α,15(S)-dihydroxy-16-fluoroprostanoate |
| 831 | 826 | diazobutane | 1-butyl 9α,15(S)-dihydroxy-15-fluoroprostanoate |
| 832 | 826 | diazooctane | 1-octyl 9α,15(S)-dihydroxy-16-fluoroprostanoate |
| 833 | 827 | diazopentane | 1-pentyl 9α,15(R)-dihydroxy-16-fluoroprostanoate |
| 834 | 828 | diazohexane | 1-hexyl 9α,15(S)-dihydroxy-16,16-difluoroprostanoate |
| 835 | 829 | diazoheptane | 1-heptyl 9α,15(R)-dihydroxy-16,16-difluoroprostanoate |
| 836 | 829 | diazodecane | 1-decyl 9α,15(R)-dihydroxy-16,16-difluoroprostanoate |

EXAMPLE 837

Preparation of 1-9α,15(S)-dihydroxy-16-fluoro prostanoic acid and 1 9β, 15(S)-dihydroxy-16-fluoroprostanoic acid To a stirred ice cold solution of 360 mg. of 1-16-fluoro-15(S)-hydroxy-9-oxoprostanoic acid (Example 822) in 50 ml. of ethanol is added 409 mg. of sodium borohydride in small portions during 1 minute. The mixture is protected from moisture and is stirred at 0° C. for 5 minutes and at ambient temperature for 6 hours. The bulk of the ethanol is evaporated at room temperature and the residue is treated with ether followed by dilute hydrochloric acid while cooling in an ice bath. The organic phase is separated and washed with water and saturated sodium chloride solution. The solution is dried over anhydrous magnesium sulfate and taken to dryness to give a mixture of the 9α- and 9β-hydroxy compounds which are separated by means of chromatography over acid-washed silica gel.

EXAMPLES 838–840

Treatment of the 9-oxo derivatives listed in Table 25 below with sodium borohydride in accordance with the procedure described in Example 837 is productive of the 9-hydroxy derivatives of the table. Each of these derivatives represents a mixture of 9α- and 9β-hydroxy compounds which are separated by chromatography on acid-washed silica gel.

TABLE 25

| Example | Starting 9-oxo- prostanoic acid of Example | Product 9α/β,15-dihydroxy derivative |
|---|---|---|
| 838 | 823 | 1-9α/β,15(R)-dihydroxy-16-fluoroprostanoic acid |
| 839 | 824 | 1-9α/β,15(S)-dihydroxy-16,16-difluoroprostanoic acid |
| 840 | 825 | 1-9α/β,15(R)-dihydroxy-16,16-difluoropro- |

TABLE 25-continued

| Example | Starting 9-oxo-prostanoic acid of Example | Product 9α/β,15-dihydroxy derivative |
|---|---|---|
| | | stanoic acid. |

EXAMPLE 841

Preparation of l-methyl 15(S)-acetoxy-9,9-diethoxy prostanoate

A solution of 3 g. of l-methyl 15(S)-acetoxy-9-oxo prostanoate (Example 52) in 20 ml. of absolute ethanol containing 3 ml. of triethylorthoformate and 30 mg. of p-toluene-sulfonic acid is kept at ambient temperature for 18 hours. After flooding with ether the solution is washed with 5% sodium carbonate solution, saturated sodium chloride solution, dried dried with anhydrous sodium sulfate and taken to dryness to furnish 3.5 g. of product.

EXAMPLE 842

Preparation of l-methyl 15(S)-acetoxy-9,9-bis(benzyloxy)-prostanoate

A solution of 2 g. of l-methyl 15(S)-acetoxy-9-oxo prostanoate (Example 52) and 25 mg. of p-toluene sulfonic acid in 65 ml. of benzylalcohol is stirred at 100° C. for 6 hours. The solution is concentrated to near dryness under reduced pressure. The residue is diluted with ether and the resulting solution is washed with 5% sodium carbonate solution, saturated sodium chloride solution, dried with anhydrous sodium sulfate and taken to dryness to afford 2.5 g. of product.

EXAMPLE 843

Preparation of l-9,9-bis(benzyloxy)-15(S)-hydroxy prostanoic acid

In the manner described in Example 58, treatment of l-methyl 15(S)-acetoxy-9,9-bis(benzyloxy)prostanoate (Example 842) with potassium hyroxide in aqueous methanol gives the subject product as an oil.

I claim:

1. A compound selected from the group consisting of an optically active compound of the formula:

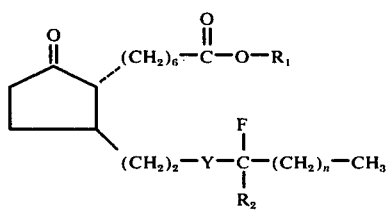

and a racemic compound of that formula and the mirror image thereof wherein Y is a divalent moiety of the formulae:

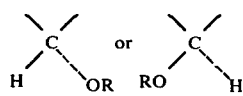

wherein R is hydrogen or lower alkanoyl; $n$ is an integer from 2 to 5, inclusive; $R_1$ is hydrogen or alkyl having from one to 12 carbon atoms; $R_2$ is hydrogen or fluorine; and the pharmacologically acceptable cationic salts thereof when $R_1$ is hydrogen.

2. The enantiomer according to claim 1, wherein Y is

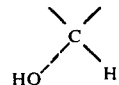

$R_1$ is hydrogen, $n$ is 3, and $R_2$ is hydrogen; l-9-oxo-15(S)-hydroxy-16-fluoro-prostanoic acid.

3. The enantiomer according to claim 1, wherein Y is

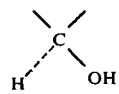

$R_1$ is hydrogen, $n$ is 3, and $R_2$ is hydrogen; l-9-oxo-15(R)-hydroxy-16-fluoro-prostanoic acid.

4. The enantiomer according to claim 1 wherein Y is

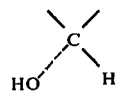

$R_1$ hydrogen, $n$ is 3, and $R_2$ is fluorine; l-9-oxo-15(S)-hydroxy-16,16-difluoro-prostanoic acid.

5. The enantiomer according to claim 1 wherein Y is

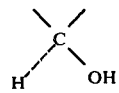

$R_1$ is hydrogen, $n$ is 3, and $R_2$ is fluorine; l-9-oxo-15(R)-hydroxy-16,16-difluoro-prostanoic acid.

6. The enantiomer according to claim 1 wherein Y is

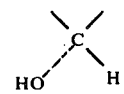

$R_1$ is n-butyl, $n$ is 3, and $R_2$ is hydrogen; n-butyl l-9-oxo-15(S)-hydroxy-16-fluoro-prostanoate.

7. The enantiomer according to claim 1 wherein Y is

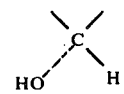

$R_1$ is n-hexyl, $n$ is 3, and $R_2$ is fluorine; n-hexyl l-9-oxo-15(S)-hydroxy-16,16-difluoro-prostanoate.

8. The racemate according to claim 1 wherein Y is

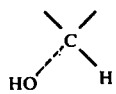

$R_1$ is hydrogen, $n$ is 3, and $R_2$ is hydrogen; dl-9-oxo-15(S)-hydroxy-16-fluoro-prostanoic acid.

9. The racemate according to claim 1 wherein Y is

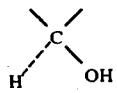

$R_1$ is hydrogen, $n$ is 3, and $R_2$ is hydrogen; dl-9-oxo-15(R)-hydroxy-16-fluoro-prostanoic acid.

10. The racemate according to claim 1 wherein Y is

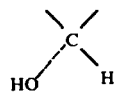

$R_1$ is hydrogen, $n$ is 3, and $R_2$ is fluorine; dl-9-oxo-15(S)-hydroxy-16,16-difluoro-prostanoic acid.

11. The racemate according to claim 1 wherein Y is

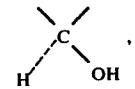

$R_1$ is hydrogen, $n$ is 3, and $R_2$ is fluorine; dl-9-oxo-15(R)-hydroxy-16,16-difluoro-prostanoic acid.

12. The racemate according to claim 1 wherein Y is

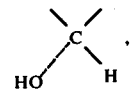

$R_1$ is n-butyl, $n$ is 3, and $R_2$ is hydrogen; n-butyl dl-9-oxo-15(S)-hydroxy-16-fluoro-prostanoate.

13. The racemate according to claim 1 wherein Y is

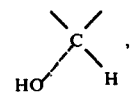

$R_1$ is n-hexyl, $n$ is 3, and $R_2$ is fluorine; n-hexyl dl-9-oxo-15(S)-hydroxy-16,16-difluoro-prostanoate.

* * * * *